United States Patent
Paulson et al.

(10) Patent No.: US 10,994,006 B2
(45) Date of Patent: May 4, 2021

(54) DESENSITIZING MAST CELLS BY CO-PRESENTATION OF ANTIGENS WITH HIGH AFFINITY MAST CELL SIGLEC LIGANDS

(71) Applicant: The Scripps Research Institute, La Jolla, CA (US)

(72) Inventors: James C. Paulson, Del Mar, CA (US); Shiteng Duan, San Diego, CA (US); Matthew MacAuley, San Diego, CA (US); Corwin Nycholat, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/315,796

(22) PCT Filed: Jul. 7, 2017

(86) PCT No.: PCT/US2017/041138
§ 371 (c)(1),
(2) Date: Jan. 7, 2019

(87) PCT Pub. No.: WO2018/009825
PCT Pub. Date: Jan. 11, 2018

(65) Prior Publication Data
US 2019/0151444 A1    May 23, 2019

Related U.S. Application Data

(60) Provisional application No. 62/359,762, filed on Jul. 8, 2016.

(51) Int. Cl.
| | | |
|---|---|---|
| *A61K 39/385* | (2006.01) | |
| *A61K 49/00* | (2006.01) | |
| *A61K 9/127* | (2006.01) | |
| *A61K 45/06* | (2006.01) | |
| *A61K 31/7028* | (2006.01) | |
| *A61K 31/7056* | (2006.01) | |
| *A61K 47/69* | (2017.01) | |
| *A61K 31/702* | (2006.01) | |
| *A61K 39/395* | (2006.01) | |
| *A61K 39/00* | (2006.01) | |

(52) U.S. Cl.
CPC .......... *A61K 39/385* (2013.01); *A61K 9/1271* (2013.01); *A61K 31/702* (2013.01); *A61K 31/7028* (2013.01); *A61K 31/7056* (2013.01); *A61K 39/39566* (2013.01); *A61K 45/06* (2013.01); *A61K 47/6911* (2017.08); *A61K 49/0084* (2013.01); *A61K 2039/55555* (2013.01)

(58) Field of Classification Search
CPC ................ A61K 9/1271; A61K 31/702; A61K 31/7028; A61K 31/7056; A61K 39/385; A61K 39/39566; A61K 45/06; A61K 47/6911; A61K 49/0084
See application file for complete search history.

(56) References Cited

U.S. PATENT DOCUMENTS

2004/0176309 A1    9/2004    Kelm et al.

FOREIGN PATENT DOCUMENTS

| WO | WO-2007056525 A2 | 5/2007 |
| WO | WO-2012018377 A2 | 2/2012 |
| WO | WO-2014188423 A1 | 11/2014 |
| WO | WO-2018009825 A1 | 1/2018 |

OTHER PUBLICATIONS

Dhanapala et al., Molecular Immunology, 2015, 66, p. 375-383, Available online May 18, 2015. (Year: 2015).*
Orgel et al., Journal of Allergy and Clinical Immunology vol. 137, Issue 2, Supplement, Feb. 2016, p. AB89 (presentation abstract), Available online Feb. 10, 2016. (Year: 2016).*
"European Application Serial No. 17743429.7, Response filed Sep. 11, 2019 to Office Action dated Mar. 1, 2019", 24 pgs.
"International Application Serial No. PCT US2017 041138, International Preliminary Report on Patentability dated Jan. 17, 2019", 8 pgs.
"International Application Serial No. PCT/US2017/041138, International Search Report dated Sep. 19, 2017", 5 pgs.
"International Application Serial No. PCT/US2017/041138, Written Opinion dated Sep. 19, 2017", 9 pgs.
Chen, Weihsu C, et al., "Antigen Delivery to Macrophages Using Liposomal Nanoparticles Targeting Sialoadhesin/CD169", PLoS ONE, 7(6), e39039, (2012), 1-9.
Kiwamoto, Takumi, et al., "Siglec-8 as a drugable target to treat eosinophil and mast cel l-associated conditions", Pharmacology and Therapeutics, vol. 135, No. 3, (Sep. 1, 2012), 327-336.
MacAuley, Matthew S., et al., "Antigenic liposomes displaying CD22 ligands induce antigen-specific B cell apoptosis", Journal of Clinical Investigations, 123(7), (2013), 3074-3083. Rillahan, Cory D., "Click and Pick: Identification of Sialoside Analogues for Siglec-Based Cell Targeting", Angew. Chem. Int. Ed., 51, Schwartz., (2012), 11014-11018.
Rillahan, Cory D., et al., "Disubstituted sialic acid ligands targeting siglecs CD33 and CD22 associated with myeloid leukaemias and B cell lymphomas", Chem. Sci., 2014, 5, 2398-2406, (Mar. 28, 2014), 2398-2406.
Rillahan, Cory D., et al., "On-Chip Synthesis and Screening of a Sialoside Library Yields a High Affinity Ligand for Siglec-7", ACS Chemical Biology, 8, (2013), 1417-1422.

* cited by examiner

*Primary Examiner* — Jonathan S Lau
(74) *Attorney, Agent, or Firm* — Schwegman Lundberg & Woessner, P.A.

(57) ABSTRACT

Compositions and methods are described herein that are useful for treating and inhibiting allergic conditions, including reducing the incidence of mast cell mediated anaphylaxis in subjects. The compositions include a carrier that displays an antigen and a Siglec ligand that binds to a Siglec on a mast cell.

14 Claims, 35 Drawing Sheets

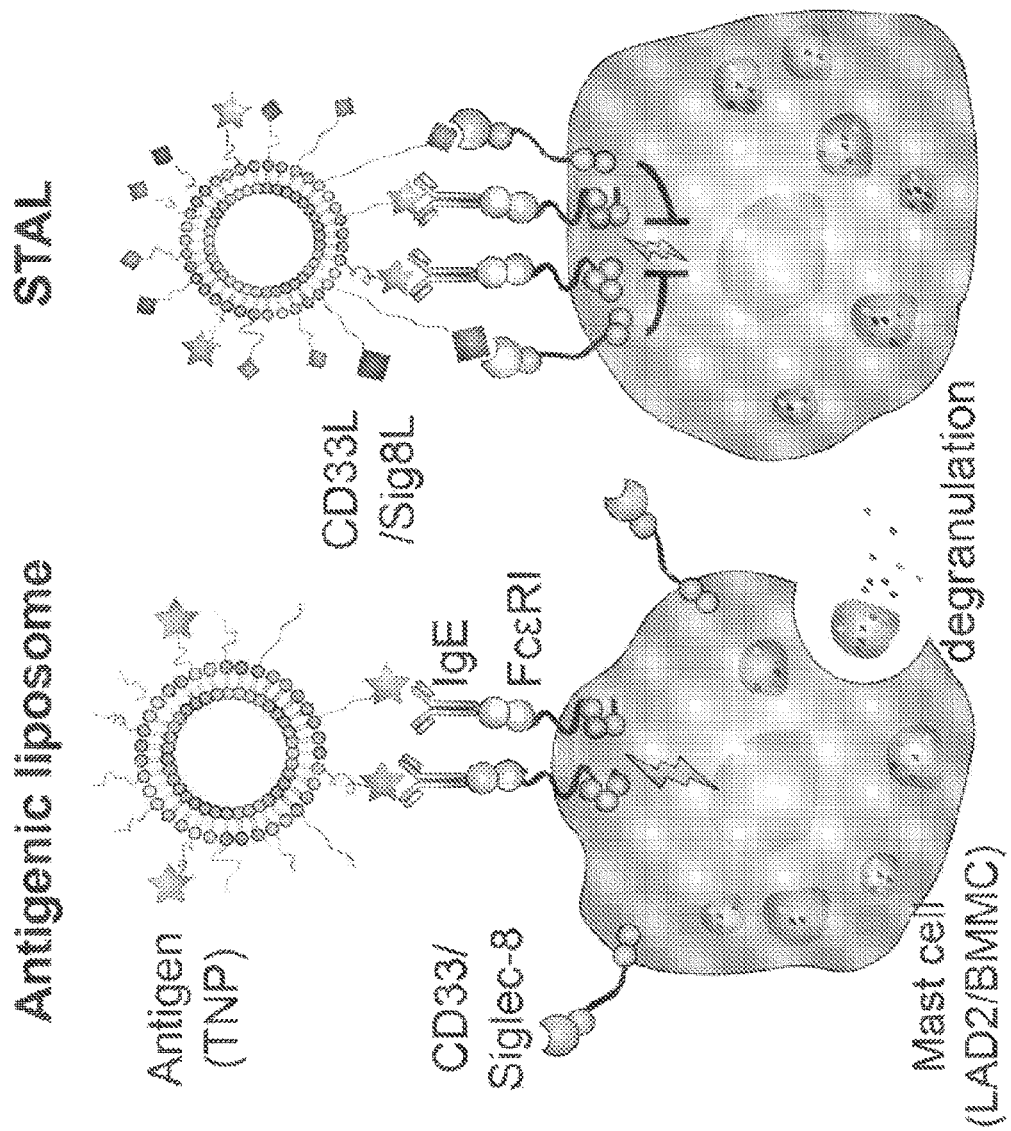

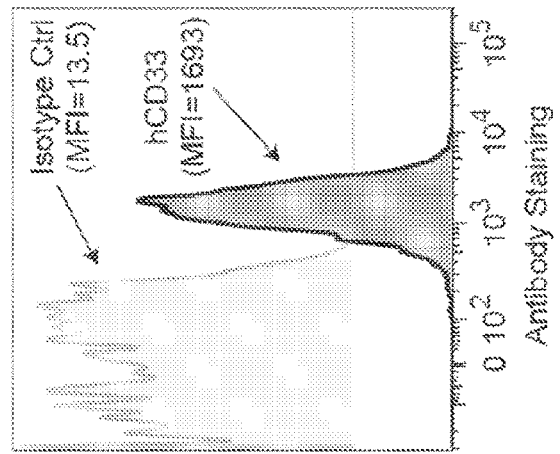
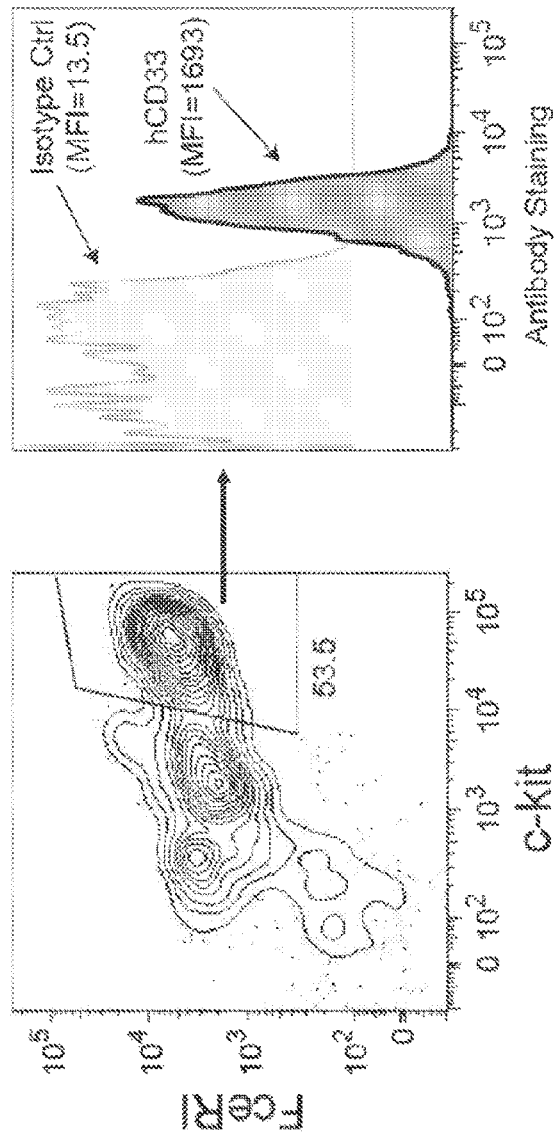

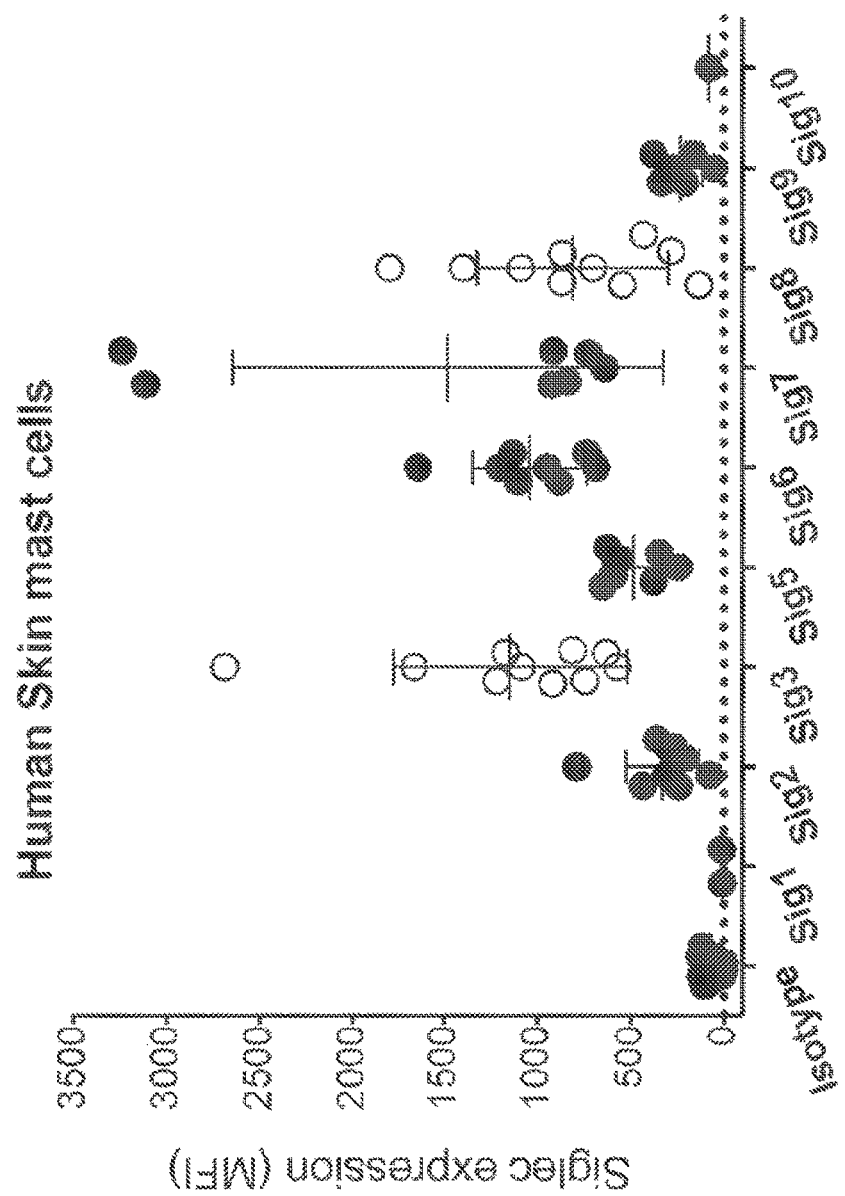

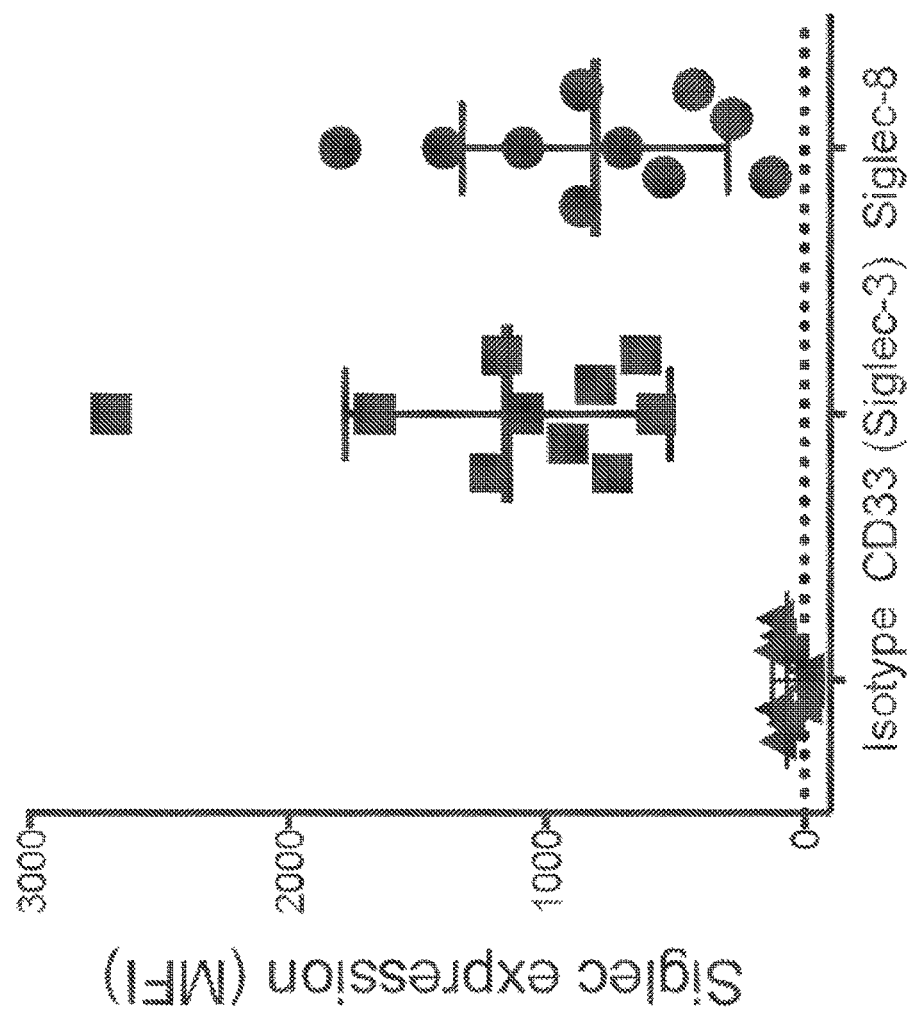

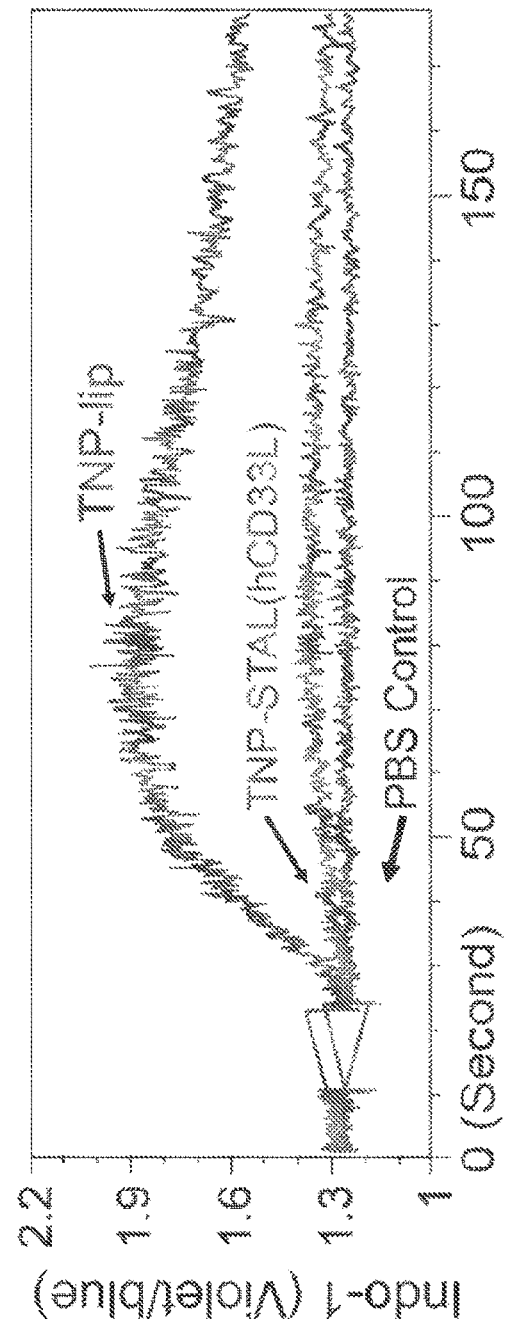

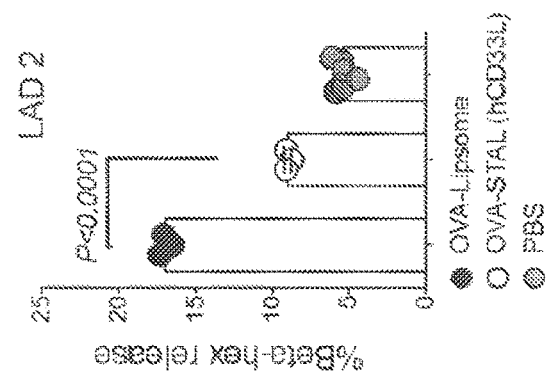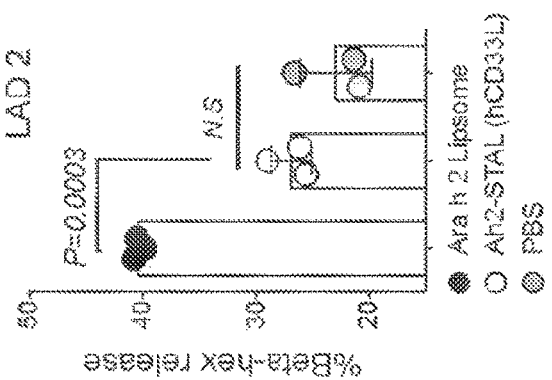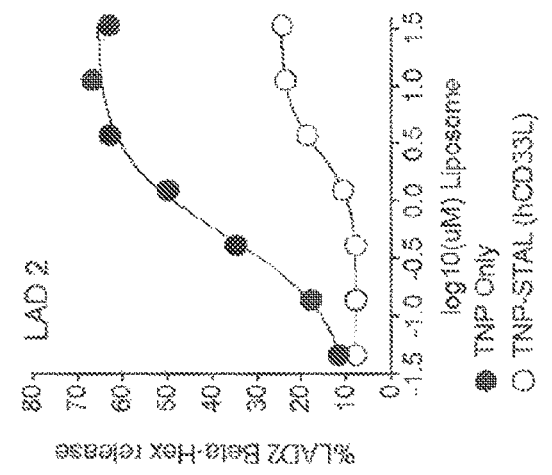

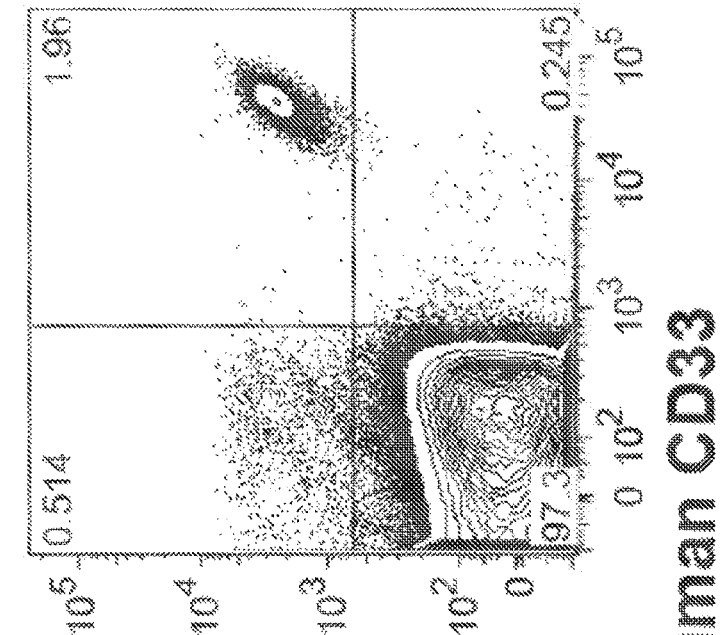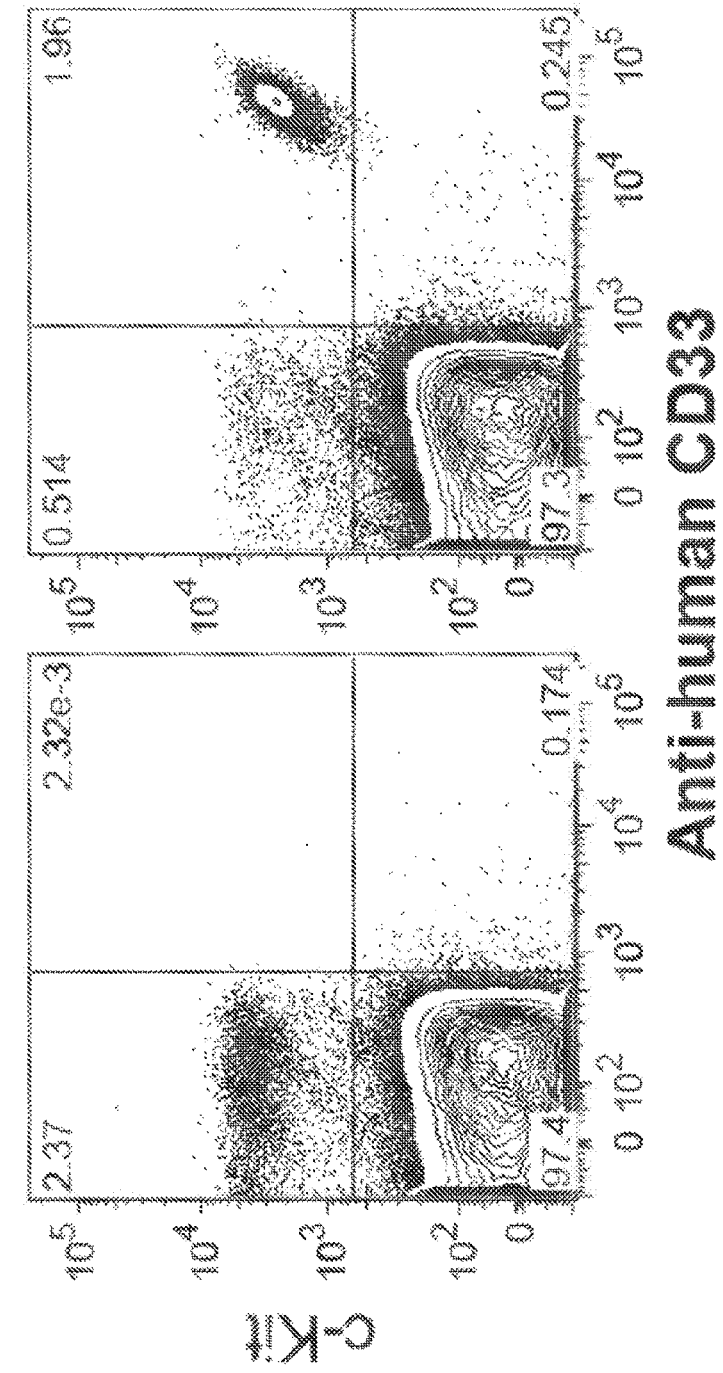

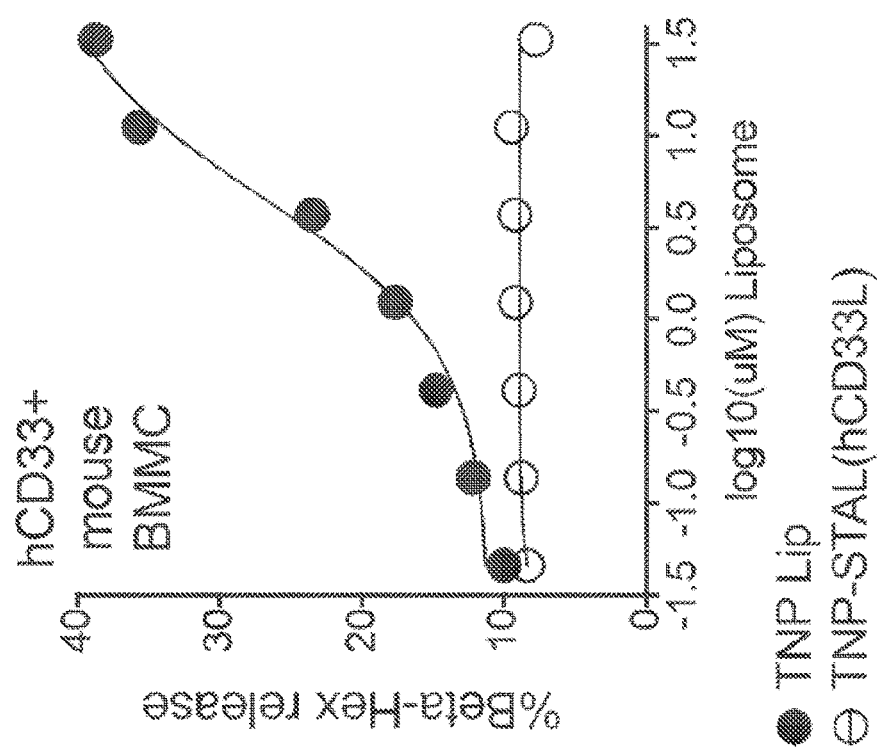

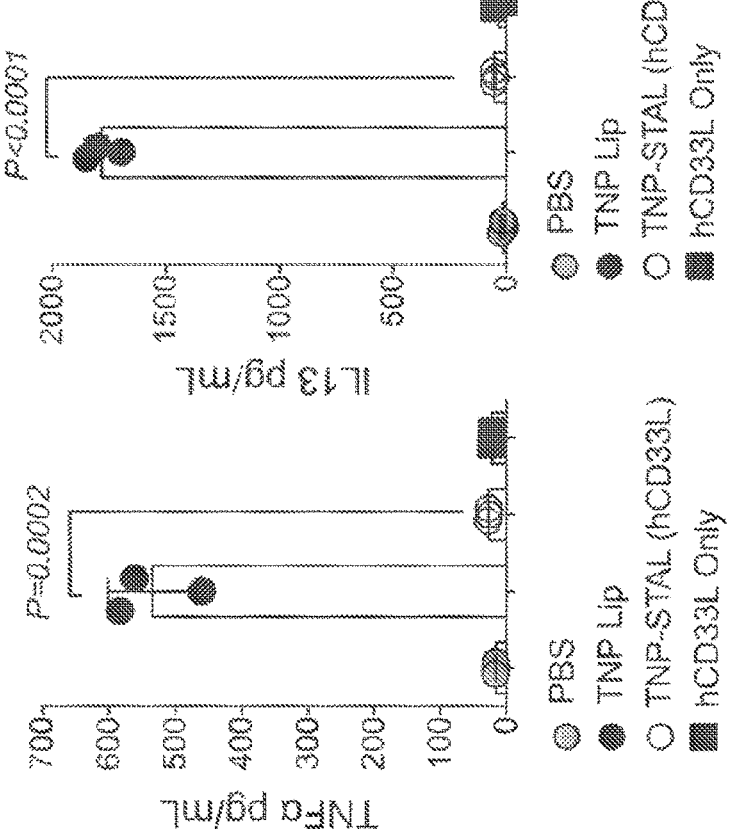
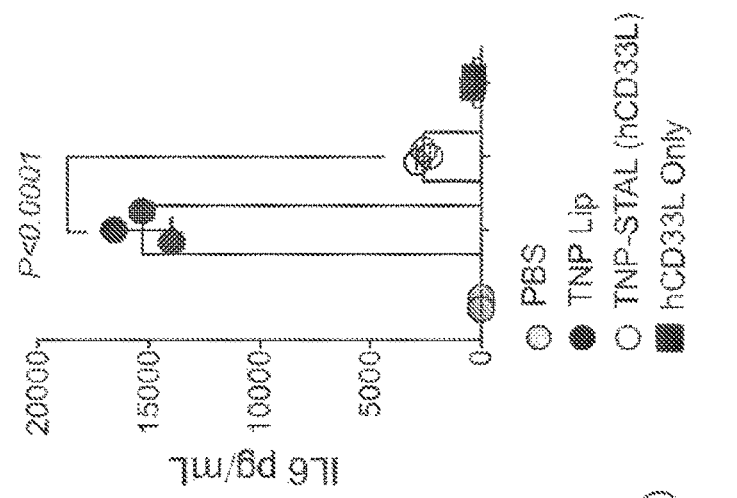

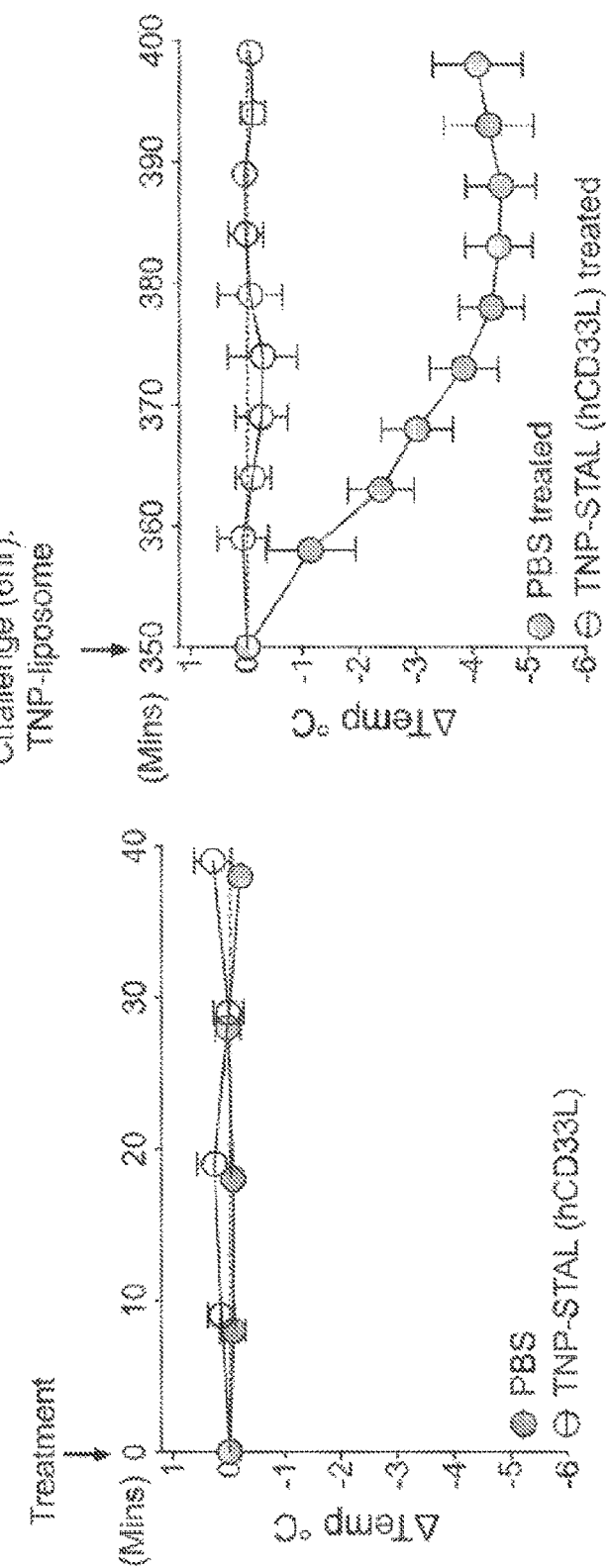

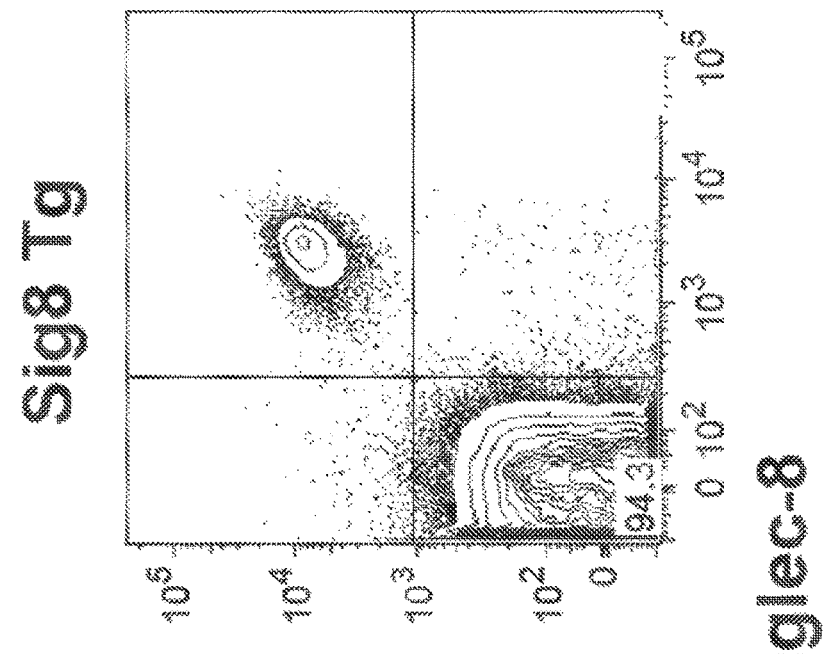
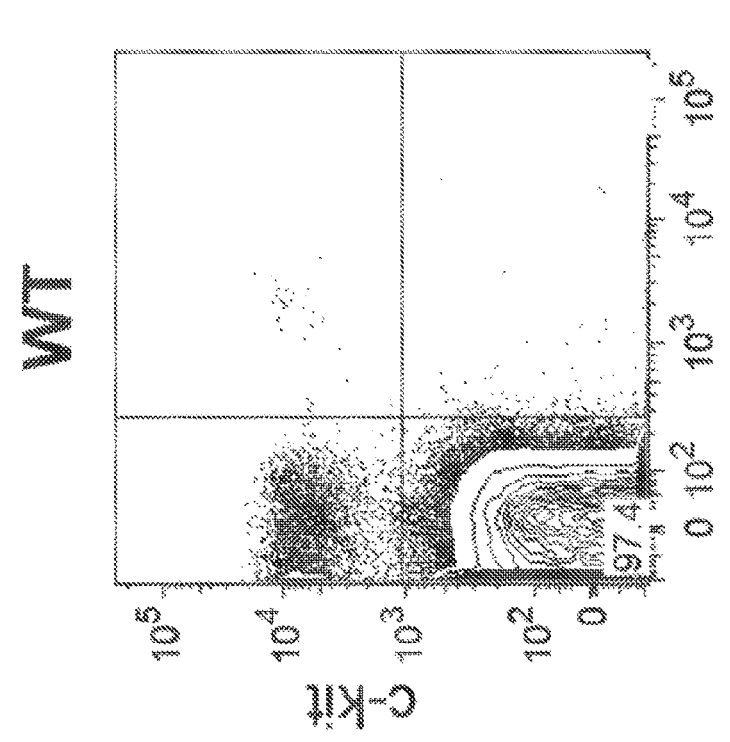

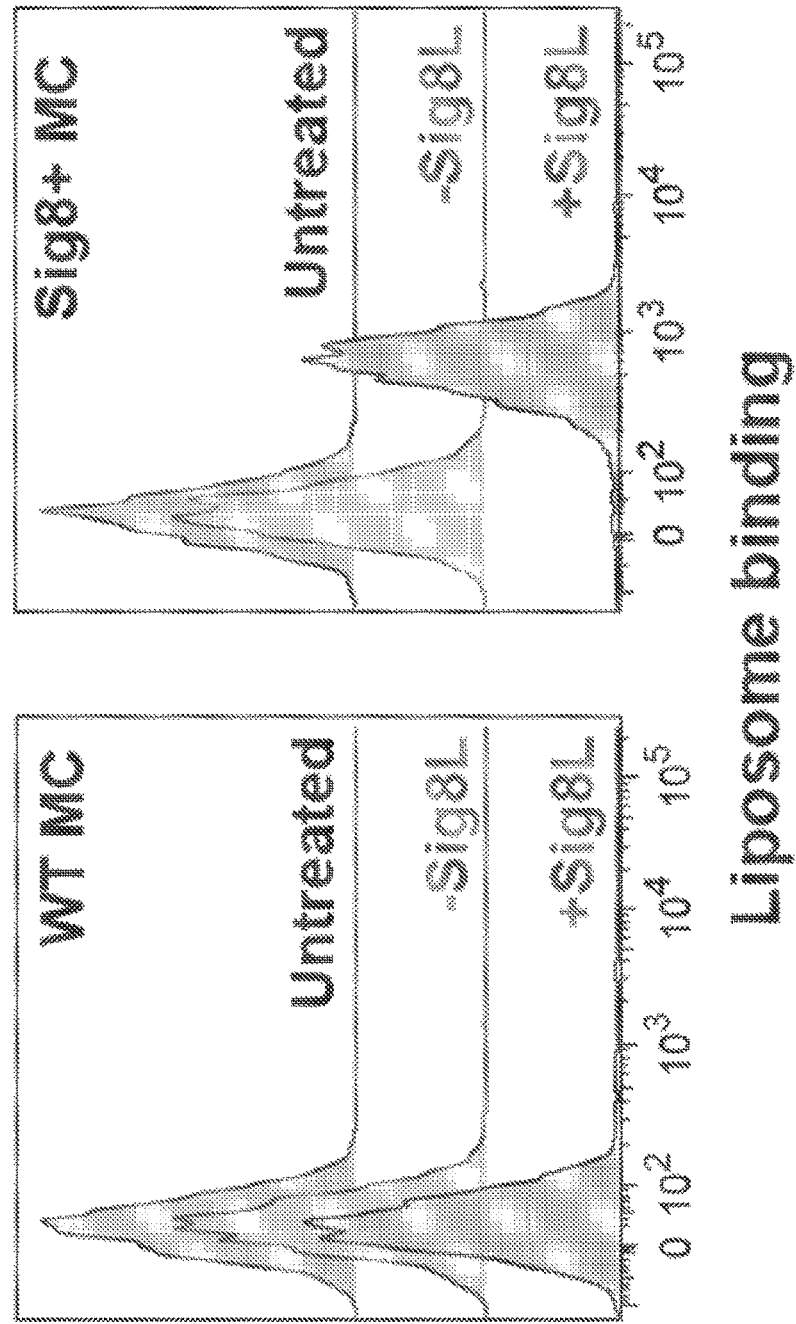

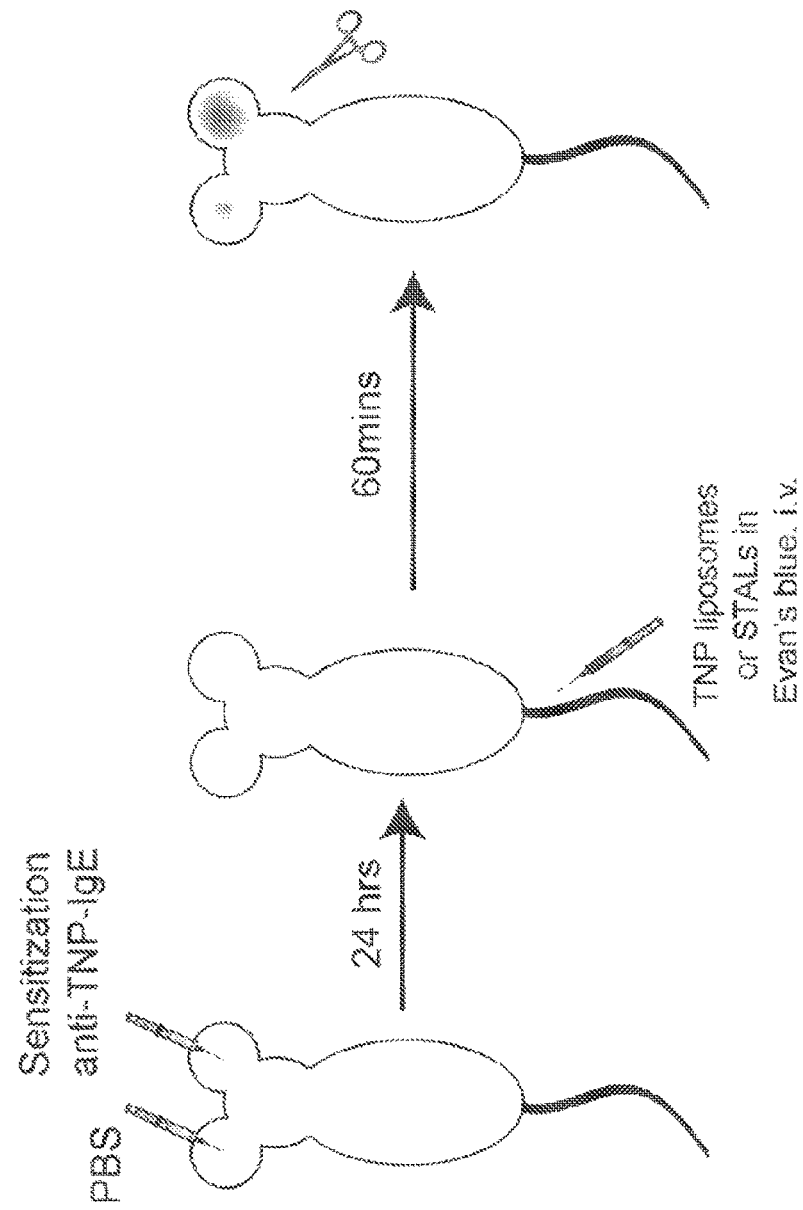

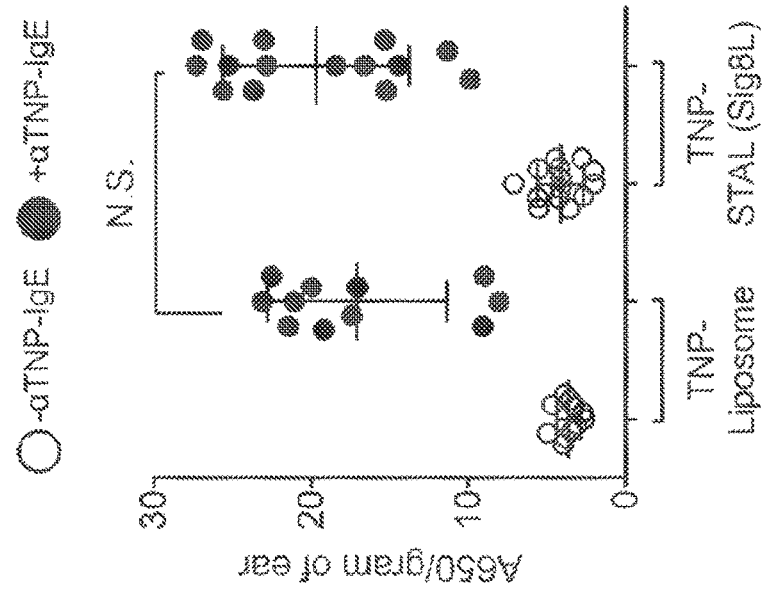
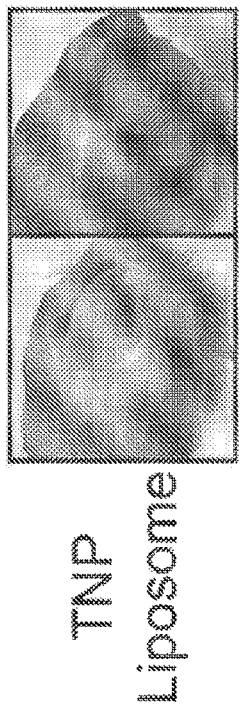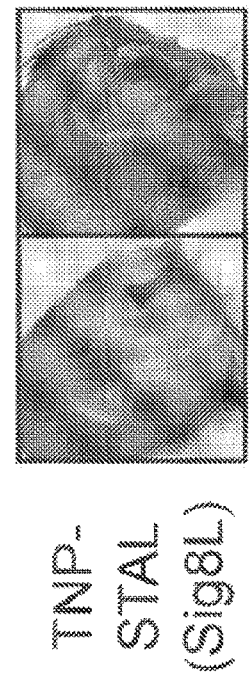

X = -OH (1-2)

or

| Compound Number | R₁ | R₂ | R₃ | R₄ | R₅ |
|---|---|---|---|---|---|
| 3 | H | H | H | H | H |
| 4 | H | H | Ph | H | H |
| 5 | H | H | H | CCH | H |
| 6 | H | H | CCH | H | H |
| 7 | H | H | H | CH₃ | H |
| 8 | H | H | H | CF₃ | H |
| 9 | H | H | H | CN | H |
| 10 | H | H | H | CH₂Cl | H |
| 11 | H | H | H | OMe | H |
| 12 | H | H | H | Ph | H |
| 13 | H | CH₃ | H | CH₃ | H |
| 14 | H | H | H | CH₃ | CH₃ |
| 15 | F | H | H | CH₃ | F |
| 16 | H | H | F | CH₃ | H |
| 17, 22 | H | CH₃ | OH | CH₃ | H |
| 18 | H | CH₃ | NH₂ | CH₃ | H |
| 19 | H | CH₃ | OMe | CH₃ | H |
| 20 | H | CH₃ | NO₂ | CH₃ | H |
| 21 | H | CH₃ | F | CH₃ | H |

R = C9-Neu5Acα2-3LacNAc-ethyl amine

DESENSITIZING MAST CELLS BY CO-PRESENTATION OF ANTIGENS WITH HIGH AFFINITY MAST CELL SIGLEC LIGANDS

This application is a national stage application filed under 35 U.S.C. § 371 from International Application Serial No, PCT/US2017/041138, filed on Jul. 7, 2017, and published as WO 2018/009825 on Jan. 11, 2018, which claims the benefit of priority to the filing date of U.S. Provisional Application Ser. No. 62/359,762, filed on Jul. 8, 2016. The contents of the above applications are incorporated herein by reference in their entireties.

GOVERNMENT SUPPORT

This invention was made with government support under P01 HL107151 and R01 AI099141 awarded by the National Institutes of Health. The government has certain rights in the invention.

BACKGROUND

The global prevalence of allergies and asthma continue to increase, affecting millions of peoples' daily lives, but treatment is far from ideal. Clinical responses to current therapies, such as inhaled corticosteroids and leukotriene modifiers, are heterogeneous and even with optimal treatment there is a substantial burden of unaddressed disease. Therefore, a need also exists for agents that can control mast cells, basophils, and eosinophils, which are the primary immune cell types that cause pathology in allergies and asthma.

Immunoglobulin E (IgE)-primed mast cells release granules and powerful chemical mediators, such as histamine, cytokines, granulocyte macrophage colony-stimulating factor (GM-CSF), leukotrienes, heparin, and many proteases into the environment. These chemical mediators directly cause the characteristic acute symptoms of allergies and recruit eosinophils that exacerbate the longer-term symptoms of diseases such as asthma.

Conventional allergen-specific immunotherapy involves inducing tolerance to antigen, which is time consuming and risky due to the risk of antigen induced anaphylaxis mediated by mast cells. Drugs such as omalizumab (Xolair) block circulating IgE from binding to FcεRI on mast cells, but its clinical efficacy remain questionable, and has been demonstrated to be non-efficacious in a significant percentage of patients. Omalizumab does not actively crosslink IgE and does not neutralize antigen-specific IgE.

SUMMARY

An alternative to currently available methods of treating allergies and anaphylaxis is described herein. Compositions and methods are described that include use of an antigen/allergen and a Siglec ligand that binds to a Siglec on a mast cell. The antigen/allergen and the Siglec ligand can be displayed on a carrier. These compositions and method enforce ligation of an inhibitory Siglec to FcεRI the antibody receptor that immobilizes IgE—which prevents degranulation of mast cells and reduces the risk of allergic reactions and anaphylaxis.

The composition and methods described herein are useful for treating IgE-mediated diseases such as allergy and anaphylaxis. The compositions target mast cells and silently desensitize the mast cells that have previously been sensitized with an antigen-specific IgE. The compositions can inhibit or reduce the incidence of antigen-mediated anaphylaxis and inhibit the degranulation of mast cells by at least 20%, at least 50%, at least 70%, at least 80%, at least 90%, at least 95%, at least 97%, at least 98%, at least 99%, or by as much as 100%.

As illustrated herein the degree to which the compositions and methods modulate mast cell and/or basophil activation can be evaluated in transgenic (Tg) mice that express human siglecs on mouse (murine) mast cells. Since mouse mast cells express no murine siglecs, mast cells from wild type mice that contain no human (or murine) Siglec serve as a control.

DESCRIPTION OF THE FIGURES

FIG. 9A schematically illustrates induction of passive systemic anaphylaxis by injection. Mice are sensitized to anti-TNP-IgE, then administered with either liposomes displaying TNP-Only (TNP-Lip, closed symbols) or with liposomes co-displaying TNP and hCD33L (TNP-STAL/hCD33L (open symbols). The rectal temperature of the mice is monitored thereafter. FIG. 9D shows results of sensitizing human CD33 transgenic mice with anti-TNP-mouse IgE followed by treatment with PBS (grey circles) or liposomes co-displaying TNP and hCD33 ligand (TNP-STAL/hCD33L; open circles). TNP-STAL did not induce any systemic anaphylaxis compared to PBS control-treated mice as quantified by drop of rectal temperature. However, the PBS-treated mice developed severe anaphylaxis when challenged with liposomes displaying TNP six hours after the original treatment (FIG. 9D), as quantified by drop of rectal temperature. FIG. 9E shows that TNP-STAL (hCD33L)-treated mice were completely protected from systemic anaphylaxis.

FIG. 10A illustrates that liposomes bearing Sig8L (CN146) do not bind to un-transfected wild type RBL cells. FIG. 10B graphically illustrates that liposomes displaying the TNP antigen and a Siglec-8 ligand (+CN146) (TNP/Sig8L-STALs) inhibit degranulation of αTNP-IgE pre-sensitized RBL cells that express Siglec-8. No such inhibition is observed in RBL cells that do not express Siglec-8 (FIG. 10A). Differences determined by unpaired t tests. FIG. 10C graphically illustrates inhibition of transgenic Siglec-8 expressing-rat basophilic leukemia cell degranulation of by different concentrations of liposomes displaying the TNP antigen and a Siglec-8 ligand (TNP+CN146, closed symbols) (TNP/Sig8L-STALs) after pre-sensitization with αTNP-IgE. FIG. 10D illustrates that wild type basophilic leukemia cells undergo degranulation in response to exposure to the antigen (TNP) and that liposomes displaying the TNP antigen and a Siglec-8 ligand (TNP+CN146, closed symbols) (TNP/Sig8L-STALs) do not inhibit such degranulation in these wild type cells.

FIG. 11A-11D illustrate expression of Siglec-8 on peritoneal mast cells harvested from wild type (WT) versus Siglec-8 transgenic mice, and the binding of liposomes displaying a Siglec-8 ligand (CN146, Sig8L) to Siglec-8 expressing mast cells. FIG. 11A illustrates flow cytometry analysis of peritoneal cells harvested from WT mice, where the cells were stained with anti-Siglec-8 antibody. FIG. 11B illustrates flow cytometry analysis of peritoneal cells harvested from Siglec-8-expressing transgenic mice, where the cells were stained with anti-Siglec-8 antibody. Peritoneal mast cells express c-Kit, and are defined as c-Kit+. WT murine peritoneal mast cells do not express human Siglec-8 (FIG. 11A), but peritoneal mast cells from Siglec-8 transgenic stain positive for Siglec-8 (FIG. 11B). FIG. 11C illustrates that liposomes do not bind to wild type peritoneal mast cells that do not express Siglec-8. FIG. 11D illustrates liposome binding to peritoneal mast cells harvested from Siglec-8-expressing transgenic mice. Fluorescent naked (−Sig8L) liposomes or liposomes bearing Siglec-8 ligand (+Sig8L) do not bind to WT mast cells compared to untreated control (FIG. 11C). In contrast, liposomes bearing the Siglec-8 ligand binds to Siglec-8+ mast cells harvested from Siglec-8-expressing transgenic mice (FIG. 11D).

FIG. 12A graphically illustrates that liposomes displaying the TNP antigen and a Siglec-8 ligand (TNP-STAL/Sig8L) inhibit degranulation of mast cells expressing Siglec-8. Mast cells that express Siglec-8 and that are exposed to liposomes displaying the TNP antigen alone (TNP-Lip; closed circles) exhibit significant degranulation as detected by β-hexosaminidase release. FIG. 12B graphically illustrates that liposomes displaying the TNP antigen and a Siglec-8 ligand (TNP-STAL/Sig8L; open symbols) inhibit production of the pro-inflammatory cytokine TNFα by mast cells expressing Siglec-8 compared to liposomes displaying TNP alone. FIG. 12C graphically illustrates that liposomes displaying the TNP antigen and a Siglec-8 ligand (TNP-STAL/Sig8L) inhibit production of the pro-inflammatory cytokine IL-13 by mast cells expressing Siglec-8 compared to liposomes displaying TNP alone. The Siglec-8 transgenic bone marrow-derived mast cells (BMMC) were pre-sensitized with αTNP-IgE.

FIGS. 13A-13E illustrate that liposomes co-displaying the TNP hapten and the Siglec-8 ligand do not stimulate TNP-induced local vascular leakage in Siglec-8 Tg mice, but TNP-induced local vascular leakage is observed in wild type (WT) mice. FIG. 13A schematically illustrates the passive cutaneous anaphylaxis (PCA) model used. This PCA model involves sensitization of the right ears of mice by injection of anti-TNP-IgE (αTNP-IgE), and injection of left ears with PBS as an injection control. The next day, the mice intravenously receive liposomes displaying TNP-only (TNP-liposomes) or liposomes co-displaying TNP and Siglec-8 ligand (TNP-STAL/Sig8L) in Evan's blue dye. Vascular leakage is detected later (e.g., 1 hour later) by leakage of Evan's blue dye, as an indicator of cutaneous anaphylaxis. FIG. 13B illustrates that in WT mice, TNP-liposomes induce local mast cell activation and turn the sensitized ears blue. Since WT mice do not express Siglec-8, liposomes co-displaying TNP and Siglec-8 ligand (TNP-STAL/Sig8L) also, to a degree, turn the sensitized ears blue. FIG. 13C quantitatively illustrates the amount of Evan's blue dye released into wild type sensitized (closed symbol) and non-sensitized (open symbols) mouse ears. FIG. 13D illustrates that TNP-liposomes induced local vascular leakage in Siglec-8 transgenic mice, but in contrast, liposomes co-displaying TNP and Siglec-8 ligand do not induce local vascular leakage. As shown in FIG. 13D, the sensitized ear retains its normal skin color as if the car had not been sensitized with anti-TNP-IgE. FIG. 13E quantitatively illustrates the amount of Evan's blue dye released into Siglec-8 transgenic sensitized (closed symbol) and non-sensitized (open symbols) mouse ears after administration of TNP-liposomes or liposomes co-displaying TNP and Siglec-8 ligand (TNP-STAL/Sig8L). As shown, the TNP-STALs prevent vascular leakage in mice that express Siglec-8.

FIG. 14A illustrates that WT mice that do not express Siglec-8 develop anaphylaxis when treated with liposomes displaying TNP antigen whether or not the Siglec-8 ligand is also displayed by the liposomes. FIG. 14B graphically illustrates the degree of anaphylaxis in transgenic mice that have mast cells expressing Siglec-8, after the mice were sensitized with αTNP-IgE, and then challenged with liposomes displaying the TNP antigen only (black circles), or with liposomes co-displaying the TNP antigen with the Siglec-8 ligand (TNP-STAL/Sig8L; open circles). The degree of anaphylaxis was detected by the rectal temperature of the mice. Siglec-8 transgenic mice develop severe anaphylaxis when given liposome bearing the TNP antigen only. In contrast, Siglec-8 transgenic mice are protected from anaphylaxis when given liposomes co-displaying TNP and Siglec-8 ligand. FIG. 14C-14E graphically illustrate the degree of anaphylaxis in Siglec-8 transgenic mice treated initially with PBS (saline control) or liposomes co-displaying TNP antigen Siglec-8 ligand (TNP-STAL/Sig8L) and then subsequently challenged one hour later with liposomes displaying TNP only. Siglec-8 mice did not develop anaphylaxis when treated with 225 ug of TNP-STAL(Sig8L) at time 0 (FIG. 14C) and time 2.5 hour (FIG. 14D) compared to PBS control. At 5 hours, when all mice were challenged with 45 ug of TNP-liposomes, mice that previously received PBS developed severe anaphylaxis (FIG. 14E). In contrast, mice received TNP-STAL(Sig8L) were resistant to anaphylaxis development (FIG. 14E).

FIG. 15A illustrates structures of Siglec-3 ligands. FIG. 15B graphically illustrates binding affinities of compounds 1-22 (shown in FIG. 15A) for Siglec-3, where human Siglec-3 (hCD33) was employed in the assays at concentrations of 2 µg/ml. FIG. 15C graphically illustrates binding affinities of compounds 1-22 (shown in FIG. 15A) for Siglec-3, where human Siglec-3 (hCD33) was employed in the assays at concentrations of 0.2 µg/ml (bottom graph). FIG. 15D graphically illustrates binding affinities of compounds 1-22 (shown in FIG. 15A) for human Siglec-2 (hCD22), where the human Siglec-2 (hCD22) was present in the assays at concentrations of 3 µg/ml (open bars) or 100 µg/ml (black bars). FIG. 15E graphically illustrates binding affinities of compounds 1-22 (shown in FIG. 15A) for mouse Siglec-1 (sialoadhesin), where the mouse Siglec-1 (sialoadhesin) was present in the assays at concentrations of 3 µg/ml (open bars) or 100 µg/ml (black bars).

FIG. 16A graphically illustrates binding affinities of potential Siglec-8 ligands 1-69 in an assay containing Siglec-8 (10 µg/ml) pre-complexed with anti-human IG-RPE (5 µg/ml). The glycans were printed on the glycan microarray by serial dilution from 100 to 0.16 µM. The binding of controls A-D is also shown. FIG. 10B shows structures of Siglec-8 ligands 9, 12, 13, 14, 18, 61, 62, and 63 that bound Siglec-8 with affinity. The ligands were linked to the C9 position of the sialic acid in R group Neu5Acα2-3LacNAc-ethylamine.

DETAILED DESCRIPTION

Figure 3:
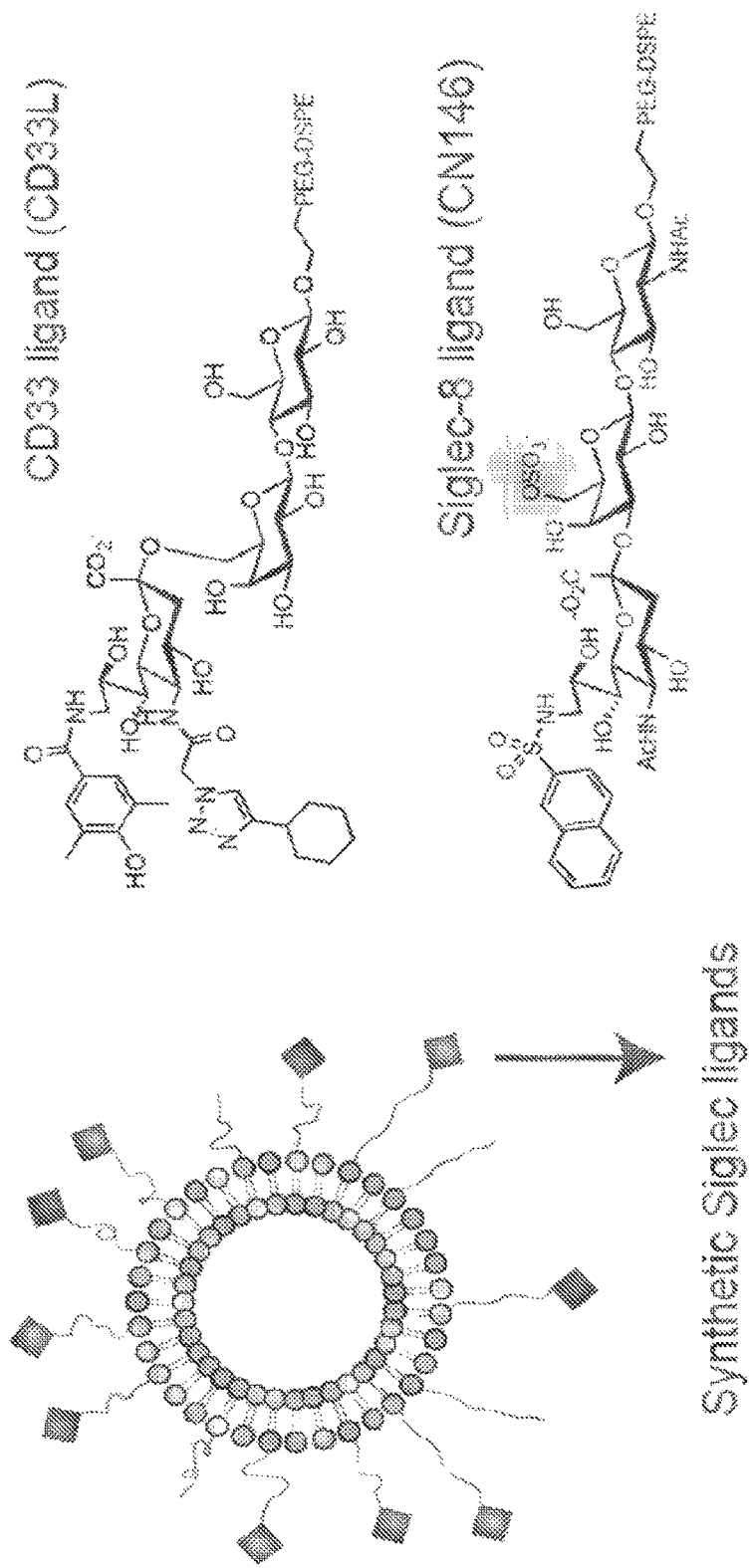

Compositions and methods are described herein that include an antigen/allergen and a Siglec-3 (CD33) ligand, Siglec-8 ligand, a Siglec-2 (CD22) ligand, a Siglec-5 ligand, a Siglec-6 ligand, a Siglec-7 ligand, or a combination thereof. As illustrated herein, when an antigen/allergen is co-presented with such Siglec ligands on a carrier to mast cells or basophils pre-sensitized with anti-antigen-IgE immunoglobulins, the antigen-IgE mediated mast cell/basophil activation and degranulation is inhibited. Significantly, these mast cells/basophils are desensitized and do not undergo degranulation even from subsequent challenges by the antigen/allergen.

Siglecs

There are fourteen human Siglecs, most of which are expressed in one or more cell types of the human immune system. Siglecs can regulate signaling of immune cells mediated by functional domains on the outside of the cell and the inside of the cell. The extra cellular portion of the Siglecs contains an iv-terminal immunoglobulin (Ig) domain that binds to sialic acid bearing ligands and that influences the organization of the Siglec on the surface of the cell. The cytoplasmic domains of Siglecs contain regulatory motifs that can regulate cell signaling receptors. Siglecs that have one or more Immunoreceptor Tyrosine Inhibitory Motif (ITIM) or ITIM-like motifs called inhibitory Siglecs, which can mediate suppression of the activation of activitory receptors on immune cells. Such inhibitory Siglecs each have the following structural ITIM domain: (Ile/Val/Leu/Ser)-X-Tyr-X-X-(Leu/Val), where X is any amino acid. Examples of inhibitory Siglec receptors found on mast cells include Siglec-2 (CD22), Siglec-3 (CD33) Siglec-5, Siglec-6, Siglec-7 and Siglec-8.

Siglec Ligands

Ligands to Sialic acid-binding Ig-like lectins (Siglecs) help to target and mediate the desensitization of mast cells and basophils to antigens. For example, as illustrated herein, ligands of mast cell inhibitory Siglecs (e.g., Siglec-2, Siglec-3 and/or Siglec-8) co-presented with antigens that bind to IgE, on sensitized mast cells can inhibit mast cell activation and degranulation.

Siglec-2 (also known as CD22) is expressed on B cells and functions as a negative regulator of B-cell receptor signaling. Upon antigen binding to the B-cell receptor, the tyrosine residues in the immuno-receptor tyrosine-based inhibitory motifs (ITIMs) of CD22 are quickly phosphorylated and recruit protein tyrosine phosphatase SHP-1, which dephosphorylates the B-cell receptor and dampens the B cell response (Nitschke & Tsubata, 2004; Tedder et al., 2005). Thus, CD22 is important for setting the threshold of B-cell receptor signaling. As illustrated herein CD22 may also be expressed at low levels of mast cells.

Siglec-3 (also known as CD33) is expressed on myeloid precursors in the bone marrow mostly in the more mature stages of the granulocytic lineage. Siglec-3 (CD33) typically binds to alpha-2-6-linked sialic acids.

Siglec-8 is a protein that in humans is encoded by the SIGLEC8 gene. Siglec-8 is expressed by human eosinophils, mast cells, and basophils—immune effector cell types that are involved in asthma, allergy, and anaphylaxis. Siglec-8 is a useful target for treatment of allergic diseases. For example, degranulation of mast cells causes bronchio-constriction, anaphylaxis, and recruitment of eosinophils, which is a hallmark of active asthma. As illustrated herein, Siglec-8 ligands that are covalently or non-covalently associated with at least one antigen/allergen have utility for the treatment of allergies and anaphylaxis, and for conditions such as asthma.

Siglec ligands can have several structural features. In some cases the ligands can have one or more substitutions (replacements) of the substituents that are present in natural sialic acids.

The most common sialic acids naturally found in humans are N-acetylneuraminic acid (Neu5Ac) and 9-O-acetyl-N-acetylneuraminic acid (9-O-Ac-Neu5Ac). In most other animals (with the notable exception of chickens) Neu5Ac co-exists with N-glycolylneuraminic acid (Neu5Gc), which has a hydroxyl group at the terminus of the N-acyl group. Structures of N-acetylneuraminic acid (Neu5Ac) and N glycolylneuraminic acid (Neu5Gc) are shown below.

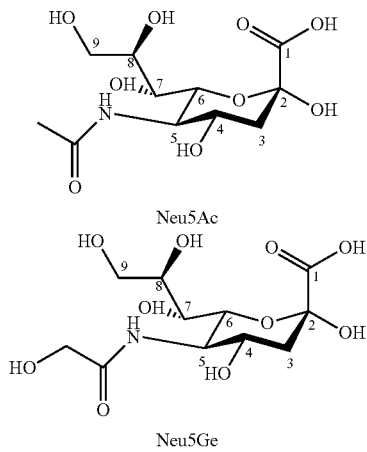

The sialic acid siglec ligands can have substituents at one or more of positions 1-9. For example, in some cases the sialic acid siglec ligands can be a compound of Formula I.

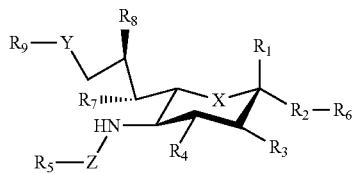

where:
X can be a methylene ($CH_2$) or a heteroatom e.g., O, N, or S);
$R_1$ can be hydrogen, carboxylase, aldehyde (CHO), phosphate or sulfate;
$R_2$ can be a hydrogen, a bond, a heteroatom, an alkyl, a hydroxy, a heterocycle, a second sugar, or a carrier;
$R_3$, $R_4$, $R_7$ and $R_8$ can each independently be hydrogen, amino, or hydroxyl;

$R_5$ can be a hydrogen, alkyl, aryl, alkylaryl, heteroaryl, or alkylheteroaryl, wherein the alkyl, aryl, alkylaryl, heteroaryl, or alkylheteroaryl group(s) can be substituted with one or more substituents selected from hydroxy, amino, azido, cyano, nitro, halo, alkyl, $CF_3$, alkoxy, carboxy late, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group;

$R_6$, can be a hydrogen, a heteroatom, a hydroxy, an alkyl, an alkylamine, an aryl, a heteroaryl, a second sugar, or a carrier;

Y can be a heteroatom, carboxyl, carboxylate, methylene, amide, —$CH_2$-amide, sulfonyl, —$CH_2$-sulfonyl, sulfonamide, —$CH_2$-sulfonamide, urea, $CH_2$-urea, thiourea, or —$CH_2$-thiourea;

Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, —$CH_2$-thiourea;

$R_9$ can be a hydrogen, hydroxyl, alkyl, alkoxy, alkylamino, amide, carbonyl, sulfonyl, urea, thiourea, aryl, arylalkoxy, alkoxyaryl, heteroaryl, or heterocycle,
where the $R_9$ alkyl, alkoxy, alkylamino, aryl, arylalkoxy, alkoxyaryl, heteroaryl, or heterocycle group(s) can be substituted with one or more substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group.

Various Siglec ligands may not have one or more of the groups listed for the $R_1$-$R_9$ substituents. Different Siglec ligands can have different structures.

In some cases the $R_5$ alkyl, aryl, alkylaryl, heteroaryl, or alkylheteroaryl groups can have 1 to 2, or 1 to 3, or 1 to 4 substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide groups. In some cases the $R_5$ alkyl, aryl, alkylaryl, heteroaryl, or alkylheteroaryl groups can have L 2, 3, 4, or 5 substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide groups.

In some cases, the $R_9$ alkyl, alkoxy, alkylamino, aryl, arylalkoxy, alkoxyaryl, heteroaryl, or heterocycle group(s) can have 1 to 2, or 1 to 3, or 1 to 4 substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkyhalide group(s). In some cases, the $R_9$ alkyl, alkoxy, alkylamino, aryl, arylalkoxy, alkoxyaryl, heteroaryl, or heterocycle group(s) can have 1, 2, 3, 4, or 5 substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group(s).

In some cases, the Siglec ligands can include two or three sugar moieties. For example, the siglec ligands can include a first, a second, and/or a third sugar, as illustrated below. The first, second, and/or third sugars can be linked either via O-glycosyl linkages, N-glycosyl linkages, or via a crosslinker covalently bound to sugar moiety heteroatom on two sugar moieties. For example, the structural diagram below illustrates a type of siglec ligand with a first, second, and an optional third sugar (where the sugars are shown as rings), where the sugars can have a linkage between them (represented by the squiggly lines in the structural diagram shown below).

In some cases, the first sugar can be a sialic acid, or a derivative thereof as shown by Formula I described above.

An optional second sugar can have the structure of Formula II.

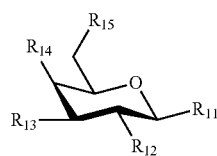

where:
$R_{11}$ is a heteroatom, hydroxy, a covalent bond, third sugar, or carrier;
$R_{12}$ is a hydrogen, or a hydroxyl;
$R_{13}$ is a hydrogen, a hydroxyl, a heteroatom, or the first sugar;
$R_{14}$ is a hydrogen, or a hydroxyl;
$R_{15}$ is a hydrogen, a hydroxyl, a heteroatom, a sulfate, or the first sugar.

In some cases, Siglec ligands can include a first sugar where the $R_2$ or the $R_6$ group is the second sugar. Linkages between the first and second sugars can be 2-3 or 2-6. In other words, the second ring atom of the first sugar can be linked to the third or to the sixth ring atom of the second sugar. For example, $R_{13}$ or $R_{15}$ of Formula II can be the first sugar, when the second sugar is present in the siglec ligand.

An optional third sugar can have the structure of Formula III.

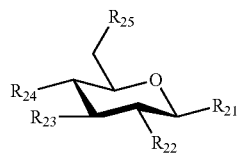

where:
$R_{21}$ is a heteroatom, an alkoxy, an ether, an alkylamine, a carrier, a crosslinker, a pegylated-lipid, a lipid, a polyacrylamide, or an O-linked alkylamine, where the heteroatom, alkoxy, ether, alkylamine, or O-linked alkylamine can be linked to, or substituted with, a crosslinker, or a carrier;
$R_{22}$ is hydrogen, heteroatom, hydroxyl, N-acetylamine, amide, sulfonamide, urea, or thiourea, where the heteroatom, hydroxyl, N-acetylamine, amide, sulfonamide, urea, or thiourea can be substituted with an alkyl, aryl or heteroaryl, and where the alkyl, aryl, or heteroaryl can be substituted with one to five hydroxy, amino, azido, cyano, nitro, halo, alkyl, $CF_3$, alkoxy, carboxylate, ether, lower alkenyl, lower alkynyl, phenyl, heteroaryl or alkylhalide group;
$R_{23}$ is a hydrogen, a hydroxyl, an acetylamine, or a fucose moiety;
$R_{24}$ is a heteroatom, a covalent bond, or the second sugar; and
$R_{25}$ is a hydrogen, hydroxyl, sulfate, carboxylate, or phosphate.

In some cases, Siglec ligands can include a second sugar and a third sugar where $R_{11}$ can be third sugar, and/or where $R_{24}$ can be a second sugar. Linkages between a second and a third sugars can be 1-4 linkages. In other words, the first ring atom of the second sugar can be linked to the fourth ring atom of the third sugar.

In some cases, when the second sugar is present in the siglec ligand, the second sugar can be galactose or a galactose substituted at the 6-position with a heteroatom, a sulfate, or the sialic acid. In other words, the second sugar can be galactose where $R_{15}$ can be a hydrogen, a hydroxyl, a heteroatom, a sulfate, or the first sugar. In some cases, the second sugar can be galactose where $R_{15}$ is a hydroxyl, or a sulfate.

Ligands for Siglec-2 (CD22) can, for example, include derivatives of N-acetylneuraminic acid sialic acid. The Siglec-2 ligands can also include the three-sugar siglec ligand described above, with a first, a second, and/or a third sugar. For example, the Siglec-2 ligands can include a substituted derivative of N-acetylneuraminic acid sialic acid where the substituents on the structure of Formula I, can be as indicated below.

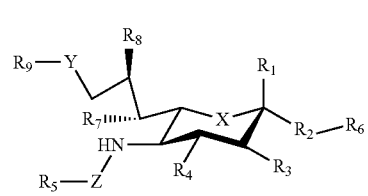

where:
X can be an oxygen heteroatom;
Z can be a carbonyl;
$R_1$ can be a carboxylate;
$R_2$ can be a hydrogen, a bond, a heteroatom, a hydroxy, a second sugar, or a carrier;
$R_3$ can be a hydroxyl;
$R_4$ can be a hydroxyl;
$R_5$ can be a lower alkyl, or a lower alkyl substituted with a halide;
$R_6$ can be a hydrogen, a heteroatom, a hydroxy, an alkyl, an alkylamine, a second sugar, or a carrier;
$R_8$ can be a hydroxyl;
Y can be —$CH_2$-amide;
$R_9$ can be aryl, heteroaryl, or heterocycle, where the aryl, heteroaryl, or heterocycle can be substituted with one to five hydroxy, amino, cyano, nitro, halo, alkyl, $CF_3$, alkoxy, carboxylate, ether, lower alkenyl, lower alkynyl, phenyl, phenoxy, or alkylhalide groups.

Examples of ligands for Siglec-2 include the following:
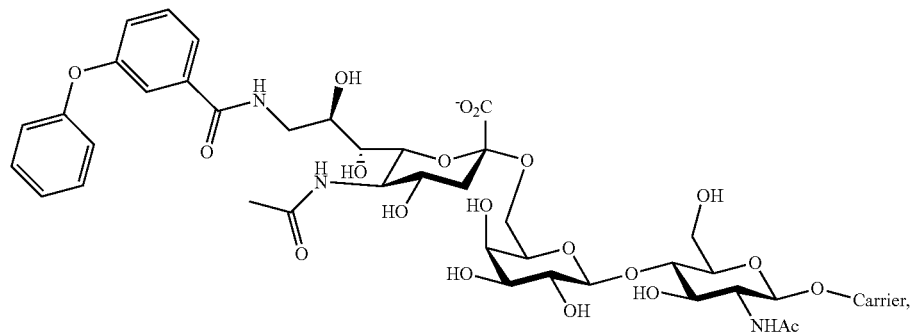
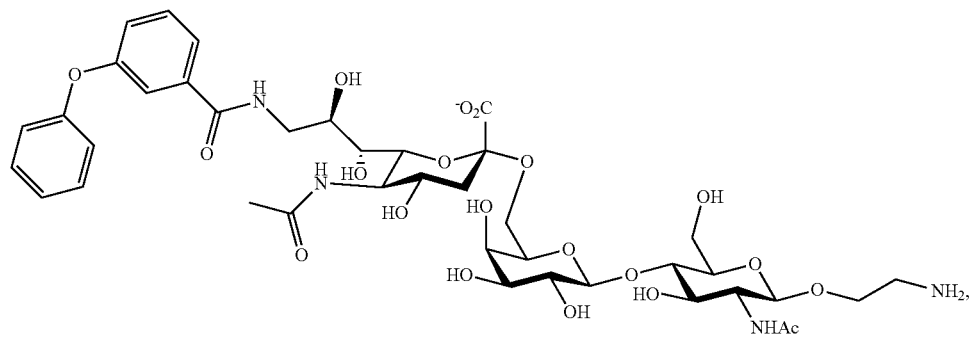
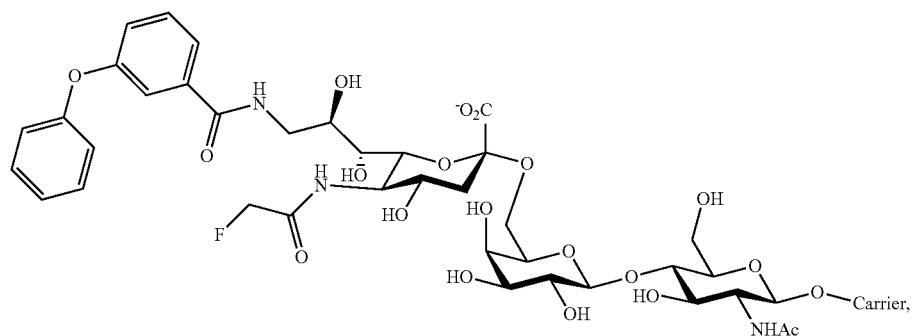
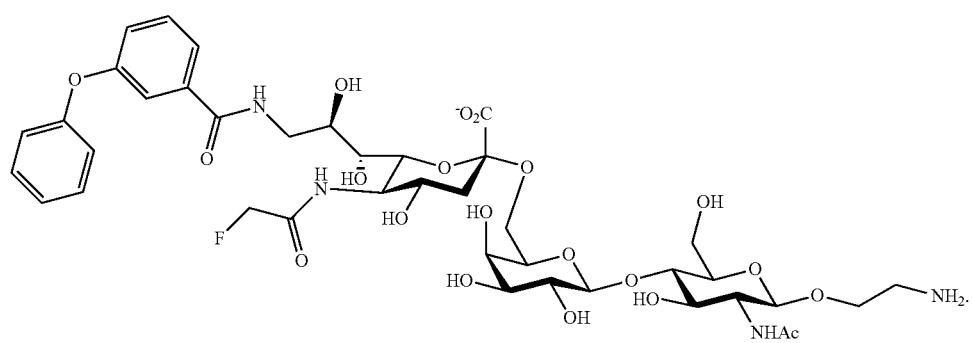

Ligands for Siglec-3 (CD33) can, for example, include derivatives of N-acetylneuraminic acid sialic acid. The Siglec-3 ligand can also include the three-sugar siglec ligand described above, with a first, a second, and/or a third sugar. For example, the Siglec-3 ligands can include a substituted derivative of N-acetylneuraminic acid sialic acid where the substituents on the structure of Formula I, can be as indicated below.

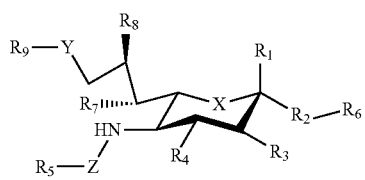

I where:

X can be an oxygen heteroatom;

Z can be a carbonyl;

$R_1$ can be a carboxylate;

$R_2$ can be a hydrogen, a bond, a heteroatom, a hydroxy, a second sugar, or a carrier;

$R_3$ can be a hydrogen, or a hydroxyl;

$R_4$ can be a hydroxyl;

$R_5$ can be a lower alkyl, or heteroaryl such as the following:

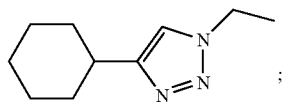

$R_6$ can be a hydrogen, a heteroatom, a hydroxy, an alkyl, an alkylamine, a second sugar, or a carrier, $R_8$ can be a hydroxyl;

Y can be —$CH_2$-amide;

$R_9$ can be aryl, heteroaryl, or heterocycle, where the aryl, heteroaryl, or heterocycle can be substituted with one to five hydroxy, amino, cyano, nitro, halo, alkyl, $CF_3$, alkoxy, carboxylate, ether, lower alkenyl, lower alkynyl, phenyl, or alkylhalide groups.

For example, the $R_9$ group of a Siglec-3 ligand can be a phenyl that can be substituted at the meta positions by a lower alkyl. Such a phenyl $R_9$ group can also be substituted at the para position with a hydroxy, amino, alkoxy, nitro, or halide.

When the Siglec-3 ligand has a second sugar, in some cases the second sugar can be linked to the 2 position of N-acetylneuraminic acid sialic acid (first sugar). For example, the $R_{15}$ can be a first sugar (a substituted derivative of N-acetylneuraminic acid sialic acid) when the Siglec-3 ligand has a second sugar.

Examples of Siglec-3 ligands include the following compounds:

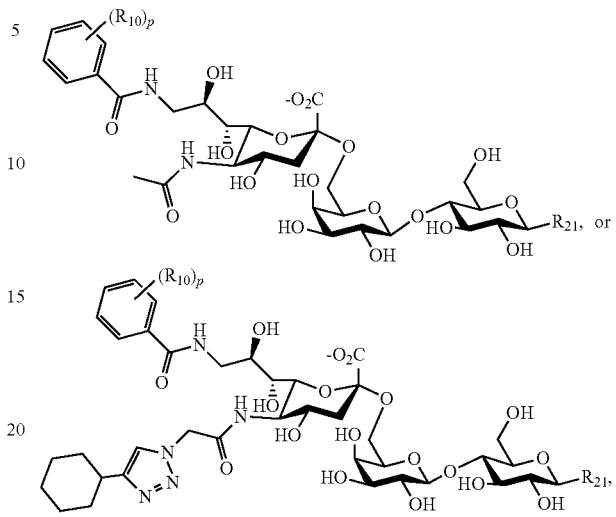

where $R_{21}$ is as described above, p is an integer of from 1-5, and each $R_{10}$ is separately selected from hydroxy, amino, cyano, nitro, halo, alkyl, $CF_3$, alkoxy, carboxylate, ether, lower alkenyl, lower alkynyl, phenyl, or alkylhalide.

Hence, a variety of Siglec-3 ligands can be used in the compositions and methods described herein.

Ligands for Siglec-5 can, for example, include derivatives of N-acetylneuraminic acid sialic acid. The Siglec-5 ligand can also include the three-sugar siglec ligand described above, with a first, a second, and/or a third sugar. For example, the Siglec-5 ligands can include a substituted derivative of N-acetylneuraminic acid sialic acid where the substituents on the structure of Formula I, can be as indicated below.

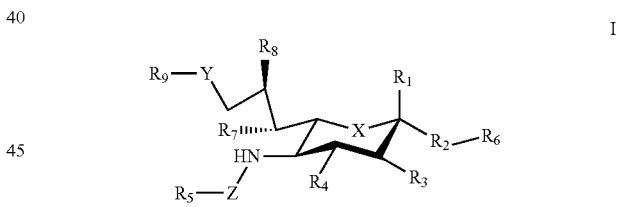

I where:

X can be an oxygen heteroatom;

Z can be a carbonyl;

$R_1$ can be a carboxy late;

$R_2$ can be a hydrogen, a bond, a heteroatom, a hydroxy, a second sugar, or a carrier;

$R_3$ can be a hydrogen, or a hydroxyl;

$R_4$ can be a hydroxyl;

$R_5$ can be an alkyl heteroaryl substituted with a heteroaryl carbamate such as the following:

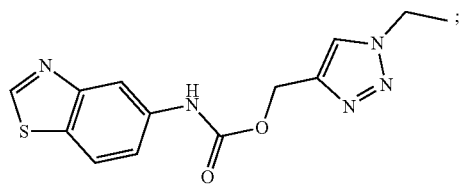 [SMILES: CCn1cc(COC(=O)Nc2ccc3scnc3c2)nn1]

R₆ can be a hydrogen, a heteroatom, a hydroxy, an alkyl, an alkylamine, a second sugar, or a carrier;

R₈ can be a hydroxyl;

Y can be an oxygen;

R₉ can be a hydrogen.

An example of a ligand for Siglec-5 is the following:

Ligands for Siglec-6 can, for example, include derivatives of N-acetylneuraminic acid sialic acid. The Siglec-6 ligand can also include the three-sugar siglec ligand described above, with a first, a second, and/or a third sugar. For example, the Siglec-6 ligands can include a substituted derivative of N-acetylneuraminic acid sialic acid where the substituents on the structure of Formula I, can be as indicated below.

I where:
X can be an oxygen heteroatom;
Z can be a carbonyl;
R₁ can be a carboxylate;
R₂ can be a hydrogen, a bond, a heteroatom, a hydroxy, a second sugar, or a carrier;
R₃ can be a hydrogen, or a hydroxyl;
R₄ can be a hydroxyl;
R₅ can be an alkyl heteroaryl substituted with a heteroarylamide such as the following:

An example of a ligand for Siglec-6 is the following:

Ligands for Siglec-7 can, for example, include derivatives of N-acetylneuraminic acid sialic acid. The Siglec-7 ligand can also include the three-sugar siglec ligand described above, with a first, a second, and/or a third sugar. For example, the Siglec-7 ligands can include a substituted derivative of N-acetylneuraminic acid sialic acid where the substituents on the structure of Formula I, can be as indicated below.

I where:
X can be an oxygen heteroatom;
Z can be a carbonyl;
R₁ can be a carboxylate;
R₂ can be a hydrogen, a bond, a heteroatom, a hydroxy, a second sugar, or a carrier;
R₃ can be a hydrogen, or a hydroxyl;
R₄ can be a hydroxyl;
R₅ can be an alkyl;
R₆ can be a hydrogen, a heteroatom, a hydroxy, an alkyl, an alkylamine, a second sugar, or a carrier;
R₈ can be a hydroxyl;
Y can be an amide, and
R₉ can be a heteroaryl carbamate where the heteroaryl can be substituted with one to two alkylheteroaryl, heteroarylalkyl groups.

An example of a ligand for Siglec-7 is the following:

Ligands for Siglec-8 can, for example, include derivatives of N-acetylneuraminic acid sialic acid such as any of the compounds of Formula 1. The Siglec-8 ligand can also include the three-sugar siglec ligand described above, with a first, a second, and/or a third sugar. For example, the Siglec-8 ligands can include a substituted N-acetylneuraminic acid sialic acid (first sugar), a second sugar, and an N-acetylated sugar (third sugar), with the structures shown above.

For example, Siglec-8 ligands can in some cases be any the compounds of Formula I, with the following substituents.

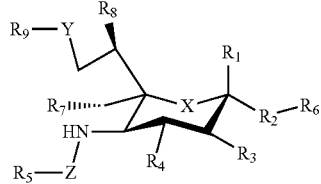

I where:
X can be an oxygen heteroatom;
$R_1$ can be a carboxylate;
$R_2$ can be a hydrogen, a bond, a heteroatom, an alkyl, a hydroxy, a second sugar, or a carrier;
$R_3$ can be a hydrogen;
$R_4$ can a hydroxyl;
$R_5$ can be alkyl, aryl, alkylaryl, heteroaryl, or alkylheteroaryl, wherein the alkyl, aryl, alkylaryl, heteroaryl, or alkylheteroaryl can be substituted with one to two substituents selected from alkyl, phenyl, or cycloalkyl group(s);

$R_6$ can be a hydrogen, a heteroatom, a hydroxy, an alkyl, an alkylamine, a second sugar, or a carrier;
$R_7$ and $R_8$ can each independently be a hydrogen, or a hydroxyl;
Y can be sulfonamide, —$CH_2$-sulfonamide, amide, urea, or thiourea;
$R_9$ can be aryl, heteroaryl, or heterocycle, where the aryl, heteroaryl, or heterocycle group can be substituted with one to five hydroxy, amino, cyano, nitro, halo, alkyl, $CF_3$, alkoxy, carboxylate, ether, lower alkenyl, lower alkynyl, phenyl, or alkylhalide groups and
Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, —$CH_2$-thiourea.

When the Siglec-8 ligand has a second sugar, in some cases the second sugar can be linked to the 2 position of N-acetylneuraminic acid sialic acid (first sugar), to some cases, the $R_{15}$ on a second sugar of a Siglec-8 ligand can be a sulfate, which can increase the affinity of a ligand for Siglec-8, In some cases, the $R_{15}$ can be a first sugar (a substituted derivative of N-acetylneuraminic acid sialic acid) when the Siglec-8 ligand has a second sugar. Some examples of Siglec-8 ligands that can be employed in the compositions described herein include the following.

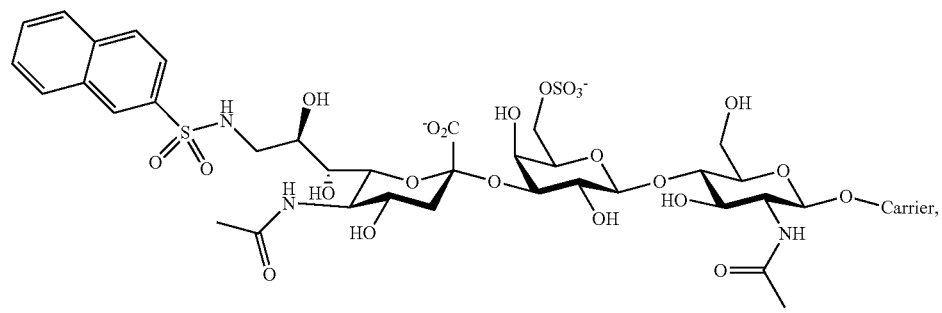

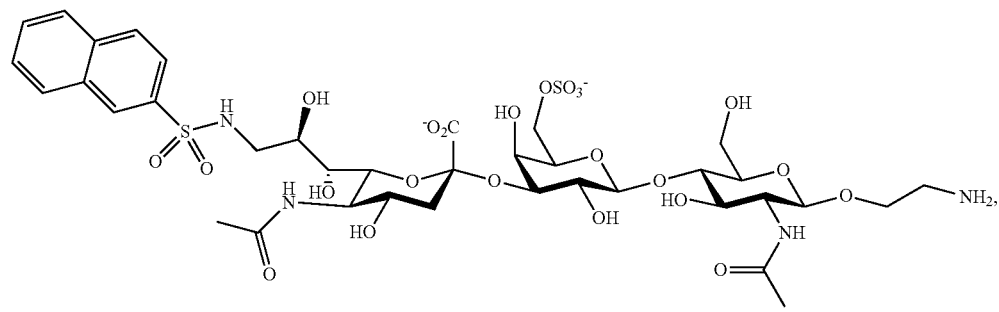

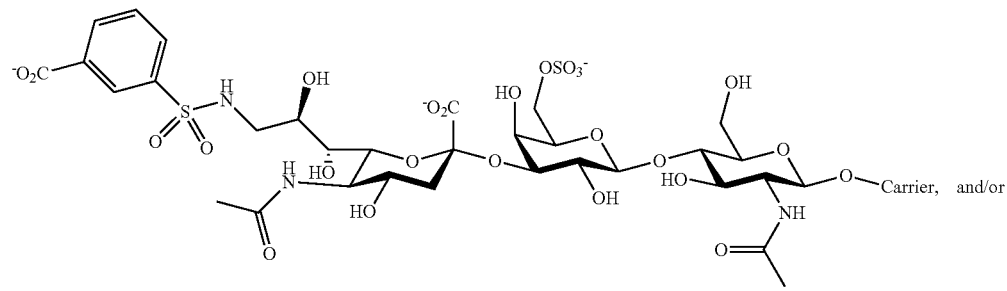

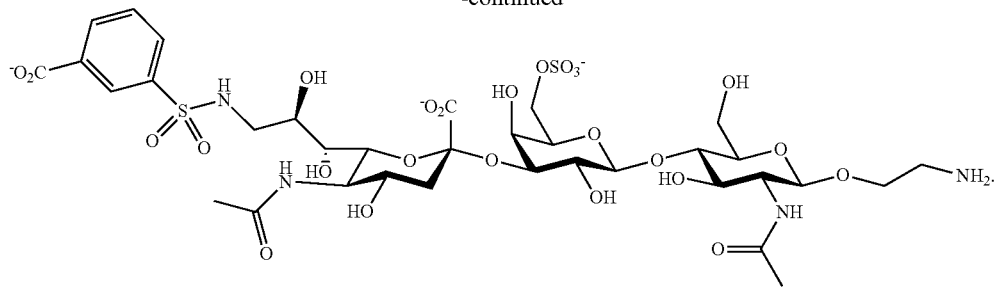

For example, Siglec-8 binds to 6'-sulfo-sLe$^x$(Neu5Acα2-3[6-SO$_4$]Galβ1-4[Fucα1-3]GlcNAc) (Buchner et al. J. Biol. Chem. 280: 4307-12 (2005); Floyd et al., J. Biol. Chem. 275: 861-66 (2000)). Natural Siglec8 ligands are shown below, where the N-acetylneuraminic acid is on the left.

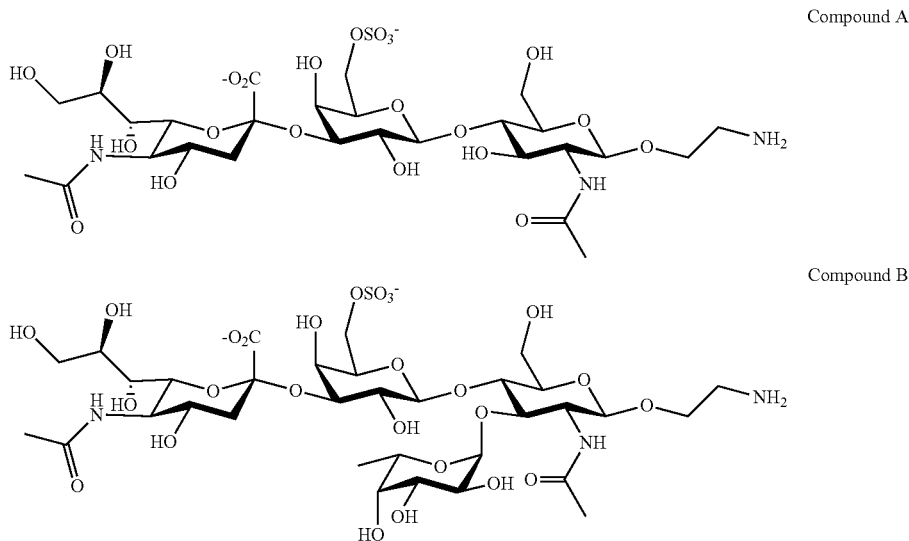

Compound A

Compound B

Such natural ligands of Siglec-8 can also be used in the compositions described herein. For example, a carrier can be linked to a natural Siglec-8 ligand and such a siglec ligand-carrier can be used in the compositions described herein.

Examples of methods used for identifying ligands for CD33 and Siglec-8 are described in Examples 15 and 16. The same or similar methods have been used to identify ligands for other Siglecs including ligands for other mast cell inhibitory Siglecs such as CD22, Siglec-5. Siglec-6 and Siglec-7.

Antigens

The compositions described herein can include one or more antigens, for example, one or more types of antigens that activate an IgE-specific response including a hapten or small molecular weight antigen, such as trinitrophenol (TNP) or a protein antigen such as the dominant peanut antigen, Ah2, or an antibody that binds to the IgE-FcεRI receptor complex, such an antibody to the FcεRI receptor, an antibody to IgE or a fragment thereof. The high-affinity IgE receptor, also known as FcεRI, or Fc epsilon RI, is the high-affinity receptor for the Fc region of immunoglobulin E (IgE). Antigens employed herein can include an antibody that binds to the FcεRI-IgE complex, or fragments thereof.

Examples of antigens that can be included in the compositions include the following: haptens, antibiotics, food allergens, environmental allergens, antibodies (including therapeutic antibodies and antibody fragments), and combinations thereof. For example, the compositions can reduce immune responses including mast degranulation when a subject is exposed to haptens such as 2,4,6-trinitrophenol; antibiotics such as β-lactam antibiotics (including penicillins and cephalosporin), monobactam (e.g., aztreonam), carbapenems (imipenem, meropenem), clavams (clavulanic acid), carbacephems (loracarbef), sulfonamides (e.g., sulfamethoxazole, sulfamerazine and sulfamethazine), antibacterial trimethoprim; neuromuscular blocking drugs such as promethazine, neostigmine, and morphine; food allergens such as egg (ovalbumin), cow (e.g., Bos d 11, Bos d 4, Bos d5, Bos d 6, Bos d 8, etc), peanuts (e.g., Ara h 2, Ara h 1, Ara h 3, Ara h 6, etc), hazelnut (e.g., Cor a 9, Car a 11, Cor a 14, etc), walnuts, casein, soy (e.g., GLy m 5, Gly m 6, etc), malt, or shellfish; environmental allergens relating to mouse (e.g., Mus m 1), rat (e.g., Rat n 1), cats (e.g., Fel d 1), dogs (e.g., Can f 1), bees, wasps, house dust mites (e.g., Der p 1), short ragweed pollen (e.g., Amb a 1), Birch pollen (e.g. Bet v 1), aspergillus (e.g., Asp r I, etc), cockroach (e.g., Bla g 2, etc), trees (pine pollen, Latex, rubber, *Hevea brasiliensis*); therapeutics (e.g., factor VIII, interferons, erythropoietin); antibodies (e.g., anti-human IgE, anti-human IgE receptor, human IgE, infliximab, adalimumab, trastuzumab, bevacizumab, rituximab, cetuximab, and fragments thereof), and combinations thereof. In some cases, more than one antigen can be displayed on the carrier or included in compositions containing a carrier-antigen-Siglec ligand complex.

Carriers

The Siglec ligands and antigens can be displayed on a carrier. In some embodiments, the carrier is a microparticle, nanoparticle, or picoparticle. In some embodiments, the microparticle, nanoparticle, or picoparticle is self-assembled. Such self-assembly can occur in vitro or in vivo. The carrier can have one or more types of Siglec ligands directly or indirectly linked to or associated with the carrier. Siglec ligands and antigens can be attached to carriers via linkers. Similarly, the carrier can have one or more types of antigens directly or indirectly linked to or associated with the carrier.

The carriers can, for example, include particles, nanoparticles, liposomes, beads, proteins, polysaccharides, lipids, and combinations thereof. The carrier scaffold can be lipid-based, protein-based, nucleic acid based, or carbohydrate-based. The carriers can be composed of polymer and/or non-polymer molecules. The carrier scaffold can be macromolecular. In some embodiments, the scaffold is composed of crosslinking chains of molecules, such as nucleic acids. In some embodiments, the scaffold is polyamino-based.

Carriers can be, but are not limited to, one or a plurality of lipid-based nanoparticles, polymeric nanoparticles, metallic nanoparticles, surfactant-based emulsions, dendrimers, and/or nanoparticles that are developed using a combination of nanomaterials such as lipid-polymer nanoparticles.

In some embodiments, the carrier can be formed by self-assembly, Self-assembly refers to the process of the formation of a carrier using components that will orient themselves in a predictable manner forming carriers predictably and reproducibly. In some embodiments, the carriers are formed using amphiphilic biomaterials which orient themselves with respect to one another to form carriers of predictable dimension, constituents, and placement of constituents.

The carriers of the compositions provided herein can have a mean geometric diameter that is less than 500 nm. In some embodiments, the carriers can have mean geometric diameter that is greater than 50 nm but less than 500 nm. For example, the mean geometric diameter of a population of carriers can be about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some examples, the mean geometric diameter is between 100-400 nm, 100-300 nm, 100-250 nm, or 100-200 nm. For example, the mean geometric diameter can be between 60-400 nm, 60-350 nm, 60-300 nm, 60-250 nm, 60-200 nm, or 75-250 nm. In some embodiments, 30%, 40%, 50%, 60%, 70%, 80%, 90%, or more of the carriers in a population of carriers have a diameter that is less than 500 nm. In some cases, 10%, 20%, 30%, 40%, 50%, 60%, 70%, 80%, 90%, or more of the carriers of a population of carriers have a diameter that is greater than 50 nm but less than 500 nm. For example, 10%, 20%. 30%, 40%, 50%, 60%, 70%, 80%, 90%, or more of the carriers of a population of carriers can have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of a population of carriers have a diameter that is between 100-400 nm, 100-300 nm, 100-250 nm, or 100-200 nm. In some embodiments, 10%, 20%, 30%, 40%, 50%, 60%, 70%, 80%, 90%, or more of the carriers of a population of carriers have a diameter that is between 60-400 nm, 60-350 nm, 60-300 nm, 60-250 nm, or 60-200 nm. In some of the foregoing embodiments, the carriers are nanoparticles.

In some embodiments, the carrier includes lipids. For example, the carrier for a combination of a Siglec ligand and an antigen can be a liposome. Liposomes normally are comprised of a lipid bilayer with an aqueous interior. The lipid bilayer can be composed of long-chain lipids, Such long-chain lipids may be any amphiphilic lipids, preferably lipids naturally prone to form so-called inverted structures. For example, the lipids may be e.g. glycerol based (e.g. phospholipids), or a sphingolipid (e.g. ceramides). Examples of lipids that can be employed include those provided in Tables 1 and 2.

TABLE 1

Symmetric Phospholipids

| Carbon number | Trivial Name | IUPAC |
|---|---|---|
| 18:1 | Petroselinoyl | 6-cis-octadecenoic |
| 18:1 | Oleoyl | 9-cis-octadecenoic |
| 18:1 | Elaidoyl | 9-trans-octadecenoic |
| 18:2 | Linoleoyl | 9-cis-12-cis-octadecadienoic |
| 18:3 | Linolenoyl | 9-cis-12-cis-15-cisoctadecatrienoic |
| 20:1 | Eicosenoyl | 11-cis-eicosenoic |
| 20:4 | Arachidonoyl | 5,8,11,14(all-cis) eicosatetraenoic |
| 22:1 | Erucoyl | 13-cis-docosenoic |
| 22:6 | DHA | 4,7,10,13,16,19 (all-cis) docosahexaenoic |
| 24:1 | Nervonoyl | 15-cis-tetracosenoic |

TABLE 2

Asymmetric Phospholipids

| Carbon Number | 1-Acyl | 2-Acyl |
|---|---|---|
| 18:0-18:1 | Stearoyl | Oleoyl |
| 18:0-18:2 | Stearoyl | Linoleoyl |
| 18:0-20:4 | Stearoyl | Arachidonoyl |
| 18:0-22:6 | Stearoyl | Docosahexaenoyl |

One or more antigens and one or more siglec ligands can be displayed on the surface of a liposome carrier.

In some embodiments, the carrier is composed of one or more polymers. For example, the one or more polymers can be water soluble, non-adhesive polymers. The polymers can, for example, be polyethylene glycol (PEG) or polyethylene oxide (PEO). In some embodiments, the polymer can include polyalkylene glycol or polyalkylene oxide. The one or more polymers can be biodegradable polymers. In some embodiments, the one or more polymers is a biocompatible polymer that is a conjugate of a water soluble, non-adhesive polymer and a biodegradable polymer. For example, the biodegradable polymer can include polylactic acid (PLA), poly(glycolic acid) (PGA), or poly(lactic acid/glycolic acid) (PLGA). In some embodiments, the carrier can be composed of PEG-PLGA polymers. In another embodiment the carrier can be hybrid particle comprised of a PLGA core surrounded by lipids.

The materials that make up the carriers can have antigens and Siglec ligands covalently or non-covalently attached to them. A linker can also be used to attach antigens and/or Siglec ligands to carriers. The carriers can also optionally include immunomodulatory agents, immunostimulatory agents and/or targeting agents.

Treatment

The compositions described herein can be administered to treat subjects, such as animals in need of such treatment, or who may develop a need for such treatment. For example, the compositions can reduce the incidence and severity of IgE-mediated disorders or diseases. Examples of IgE-mediated disorders or diseases that can be treated include allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction and allergic purpura.

Animals including humans, domesticated animals, zoo animals, and experimental animals can be administered the compositions.

Administration of the compositions described herein can reduce the incidence of antigen-specific mast cell or basophil degranulation by at least 10%, or at least 20%, or at least 25%, or at least 30%, or at least 35%, or at least 40%, or at least 45%, or at least 50%, or at least 55%, or at least 60%, or at least 65%, or at least 70%, or at least 80%, at least 90%, at least 92%, at least 95%, at least 97%, at least 98%, or at least 99%. In some cases, the compositions describe herein can reduce the symptoms and/or incidence of antigen-specific mast cell or basophil degranulation by 100%.

Dosages, Formulations and Routes of Administration

The compositions described herein can include at least an antigen, at least one Siglec ligand, and at least one carrier. The antigen can be any of the antigens described herein, including an antibody or antibody fragment that binds to an FcεRI-IgE complex or a fragment thereof. In some cases, a combination of antigens can be included in the compositions. In some cases, the compositions can include an antibody that binds to an FcεRI-IgE complex or a fragment thereof in addition to a complex of antigen, at least one Siglec ligand, and at least one carrier.

The compositions described herein can be used to modulate an immune response (e.g., enhance, suppress, inhibit, direct, or redirect). For example, the compositions can inhibit antigen-IgE mediated mast cell/basophil activation and degranulation. In some embodiments, the compositions can include at least one IgE antigen, and one or more types of Siglec-2, Siglec-3, Siglec-5, Siglec-6, Siglec-7, and/or Siglec-8 glycan ligands. The compositions can optionally include an immunomodulatory agent.

Compositions described herein can be administered so as to ameliorate one or more symptoms of disease or condition. In some embodiments, the compositions can be administered so as to achieve a reduction in at least one symptom associated with an IgE-mediated disorder or disease. Examples of IgE-mediated disorders or diseases include allergic rhinitis, allergic asthma, non-allergic asthma, atopic dermatitis, allergic gastroenteropathy, anaphylaxis, urticaria, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction and allergic purpura.

The compositions are particularly amenable to formulation into pharmaceutical compositions, for example, because they are composed of glycans that have substantially no toxicity. Moreover, compared to many biological molecules, the glycans are relatively small and stable. Hence, the Siglec ligands and antigens are readily formulated into highly effective, stable and substantially non-toxic compositions.

To achieve the desired effect(s), the antigens, Siglec ligands, or combination thereof may be administered in single or divided dosages. In general, the antigens and Siglec ligands are administered together, for example, by displaying the antigens and Siglec ligands on a carrier.

For example, the antigen and/or Siglec ligand can be present in the compositions in amounts of at least about 0.01 mg/kg to about 100 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results.

The amount administered will vary depending on various factors including, but not limited to, what types of antigens, Siglec ligands, and/or other therapeutic agents are administered, the route of administration, the progression or lack of progression of the disease, the weight, the physical condition, the health, the age of the patient, whether prevention or treatment is to be achieved, and if the antigen or ligand is chemically modified. Such factors can be readily determined by the clinician employing animal models or other test systems that are available in the art.

Siglec ligands, and antigens (for example directly or indirectly linked to a carrier), may be administered in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions may be essentially continuous over a pre-selected period of time or may be in a series of spaced doses. Both local and systemic administration is contemplated.

To prepare the composition, the Siglec ligands, antigens, or combinations thereof are synthesized or otherwise obtained, and purified as necessary or desired. These therapeutic agents can then be lyophilized or stabilized, for example, if storage is desirable. These agents can be combined with a carrier such as a liposome, nanoparticle, or other particle. The concentrations of the agents can be evaluated and adjusted to an appropriate amount, and these therapeutic agents can optionally be combined with other agents.

In general, dosage forms of the invention comprise an amount of at least one of the Siglec ligands and/or antigens effective to treat or prevent the clinical symptoms of a disease (e.g. an IgE-mediated disorder or disease). Any statistically significant attenuation of one or more symptoms of an IgE-mediated disorder or disease is considered to be a treatment thereof.

The absolute weight of a given Siglec ligand, antigen, antibody, or other therapeutic agent that is included in a unit dose can vary widely. For example, about 0.01 to about 2 g, or about 0.1 to about 500 mg, of at least one Siglec ligand, antigen, antibody, or therapeutic agent can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of a Siglec ligand, antigen, antibody, or other therapeutic agent can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

The compositions can include a carrier such as a pharmaceutically acceptable carrier. By "pharmaceutically acceptable" it is meant a pharmaceutical carrier, diluent, excipient, and/or salt that is compatible with the other ingredients of the formulation, and not deleterious to the recipient thereof. Note that the carriers associated with the Siglec ligands, antigens, therapeutic agents, or combinations thereof can be distinct from the "pharmaceutically acceptable carrier" or a "pharmaceutical carrier" described in this section. Thus, a "pharmaceutically acceptable carrier" or a "pharmaceutical carrier" is a non-active ingredient that is not deleterious to the recipient thereof and that can solubilize or disperse the active ingredients to facilitate formulation of a convenient dosage form.

One or more suitable unit dosage forms comprising the therapeutic agents of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid solutions, solid matrices, semi-solid pharmaceutical carriers, finely divided solid pharmaceutical carriers or combinations thereof, and then, if necessary, introducing or shaping the product into the desired delivery system.

Pharmaceutical formulations containing the therapeutic agents described herein can be prepared by procedures known in the art using well-known and readily available ingredients. The formulations can contain pharmaceutically acceptable carriers, vehicles and adjuvants. For example, the therapeutic agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives.

Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Lubricants such as talc, calcium and magnesium stearate, and solid polyethylene glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," poly glycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

The therapeutic agents may be formulated for parenteral administration (e.g., by injection, for example, bolus injection or continuous infusion) and may be presented in unit dose form in ampoules, pre-filled syringes, small volume infusion containers or in multi-dose containers. The administration can, for example, be subcutaneous, or intravenous.

As noted above, preservatives can be added to help maintain the shelve life of the dosage form. The active agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder limn, obtained by aseptic isolation of sterile solid or by lyophilization from solution, for constitution with a suitable vehicle, e.g., sterile, pyrogen-free water, before use.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste.

In some case, the compositions can be prepared for, and administered as, oral compositions. For example, tablets or caplets containing the therapeutic agents (e.g., antigens, siglec ligands, and optionally a carrier) of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the therapeutic agents of the invention are designed to resist disintegration in the stomach and dissolve in the more neutral to alkaline environment of the duodenum.

Orally administered therapeutic agents of the invention can also be formulated for sustained release. For example, the therapeutic agents can be coated, micro-encapsulated, or otherwise placed within a sustained delivery device. The total active ingredients in such formulations comprise from 0.1 to 99.9% by weight of the formulation.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

The compositions can also include antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the therapeutic agents are well suited to formulation as sustained release dosage forms and the like. The formulations can be so constituted that they release the active agent, for example, in a particular part of the vascular system or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated by available methods for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols.

The compositions can be delivered via patches or bandages for dermal administration. Alternatively, the therapeutic agents can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid pharmaceutical carrier.

The compositions may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

The active ingredients of the invention can also be administered to the respiratory tract. Thus, the present invention also provides aerosol pharmaceutical formulations and dosage forms for use in the methods of the invention.

For administration by inhalation or insufflation, the composition may be in the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*. Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid therapeutic agent that are not dissolved or suspended in a liquid are also useful in the practice of the present invention. Therapeutic agents of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder.

It will be appreciated that the unit content of active ingredient or ingredients contained in an individual aerosol dose of each dosage form need not in itself constitute an effective amount for treating the particular immune response, allergy, asthma, anaphylaxis or other disease or condition since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount, Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler, Typical of atomizers are the Mistometer (Wintrop) and the Medihaler (Riker).

Furthermore, the active ingredients may also be used in combination with other therapeutic agents, for example, pain relievers, anti-inflammatory agents, anti-cancer agents and the like, whether for the conditions described or some other condition.

Kits

The present invention further pertains to a packaged pharmaceutical composition such as a kit or other container for detecting, controlling, preventing or treating a disease. The kits of the invention can be designed for detecting, controlling, preventing or treating diseases such as those described herein (e.g., an allergy, anaphylaxis).

In one embodiment, the kit or container holds a Siglec ligand and an antigen for inhibiting activation and/or degranulation of mast cells or basophils, as well as instructions for preparing a composition that includes the Siglec ligand and the antigen. The kit can also include a carrier (e.g., components for a liposomal or particle-based carrier). The kit can also include an FcεRI-IgE complex or a fragment thereof that can be packaged separately or with the antigen and/or the Siglec ligand.

In another embodiment, the kit or container holds a therapeutically effective amount of a pharmaceutical composition for treating, preventing or controlling a disease and instructions for using the pharmaceutical composition for control of the disease. The pharmaceutical composition includes at least one types of Siglec ligand and at least one antigen, in a therapeutically effective amount such that the disease is controlled, prevented or treated. The ligand and antigen composition can be provided in combination with a carrier that can display the ligand and the antigen. Such a composition can be in liquid form, powder form or other form permitting ready administration to a patient.

The kits of the invention can also comprise containers with tools useful for administering the compositions of the invention. Such tools include syringes, swabs, catheters, antiseptic solutions and the like.

Definitions

Aryl groups are cyclic aromatic hydrocarbons that do not contain heteroatoms. An aryl group can have about five to about fourteen ring atoms in which at least one ring is aromatic. Examples include a phenyl ring, a bicyclic ring (e.g., biphenyl), or tricyclic ring. Bicyclic and tricyclic rings can be ortho-fused but, as used herein, the bicyclic and tricyclic rings need not be fused and can be separate rings linked together by a covalent bond or a short alkyl (e.g. $C_1$-$C_3$ alkyl). Examples of aromatic groups include groups such as benzene, phenyl, biphenyl, naphthalene, anthracene, or a combination thereof.

Thus aryl groups include, but are not limited, to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclic or heterocycle groups include aromatic and non-aromatic ring compounds containing three or more ring atoms, of which, one or more is a heteroatom such as, but not limited to, N, O, and S. The heteroatom can, for example, be a nitrogen atom. In some embodiments, heterocycle groups include 3 to about 20 ring atoms, whereas other such groups have 3 to about 15 ring atoms. A heterocycle group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocycle ring can also include one or more double bonds. A heteroaryl ring is an embodiment of a heterocycle group. The phrase "heterocycle group" includes fused ring species including those comprising fused aromatic and non-aromatic groups. For example, a dioxolanyl ring and a benzdioxolanyl ring system (methylenedioxyphenyl ring system) are both heterocycle groups within the meaning herein. The phrase also includes polycyclic ring systems containing a heteroatom such as, but not limited to, quinuclidyl. Heterocyclic groups can be unsubstituted, or can be substituted as discussed above. Heterocyclic groups include, but are not limited to, pyrrolidinyl, piperidinyl, piperidinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocycle groups can be mono-substituted or substituted more than once, such as, but not limited to, piperidinyl or quinolinyl groups, which are 2-, 3-, 4-, 5-, or 6-substituted, or disubstituted with groups such as those listed above.

In some embodiments, the heterocyclic ring is a non-aromatic ring with one or two heteroatoms. For example, the heterocyclic ring can be a non-aromatic ring with one heteroatom. The heteroatom can, for example, be oxygen, sulfur, or nitrogen.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Lower alkyl groups have about 1 to about 3 carbon atoms.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein. A lower alkoxy group has about 1 to about 3 carbon atoms.

An "amino" group is a substituent of the form —$NH_2$, —NHR, —$NR_2$, —$NR_3^-$, and protonated forms of each, wherein each R is independently selected from a hydrogen or a lower alkyl group.

"Halogen" or "halo" as the term is used herein includes fluoro, chloro, bromo, and iodo.

All chiral, diastereomeric, racemic forms of a structure are intended to be embraced by the claims, unless the specific stereochemistry r isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The following examples are for illustration of certain aspects of the invention and is not intended to be limiting thereof.

Example 1: Materials and Methods

This Example describes some of the materials and methods employed in developing the invention. FIG. 3 shows a schematic diagram of liposomes that display Siglec ligands (diamond symbols).

General Procedure for Substitution of the 9 Position of Sialic Acid

Sialoside derivatives containing 9-azido-9-deoxy-N-ace neuraminic acid (9-azido Neu5Ac), including but not limited to 9-azido Neu5Acα2-3-galactoseβ1-4-N-acetylglucosamine, 9-azido Neu5Acα2-3-(6'-O-sulfo)-galactoseβ1-4-N-acetylglucosamine, 9-azido Neu5Acα2-3-galactoseβ1-4-glucose, 9-azido Neu5Acα2-6-galactoseβ1-4-N-acetylglucosamine, 9-azido-9-deoxy-N-pentenoyl-neuraminic acidα2-6-galactoseβ1-4-N-acetylglucosamine, 9-azido Neu5Acα2-6-galactoseβ1-4-glucose (1 eq., 25-50 µmol) were dissolved in water (1-2 mL, pH 10) then 2 equivalents of trimethyl phosphine (1.0 M in THF solution) was added at room temperature. When the reaction showed complete reduction of the azide to the amine (analyzed by silica gel thin layer chromatography, eluent: ethyl acetate:methanol:acetic acid:water; 6:3:3:2, by volume), the mixture was concentrated, reconstituted in water and the product was purified by gel filtration chromatography (Bio-Gel P-2, 1×70 cm, equilibrated in water). The compounds were eluted with water, the appropriate fractions containing product were pooled, and the sample lyophilized to remove water, leaving a white amorphous product. The remaining white solid was dissolved in methanol (1-2 mL) containing isopropyl-ethyl-amine (10 eq.). Amine reactive reagents (2 eq) including substituted acyl chlorides or N-hydroxy succinimde activated esters to form amides, or sulfonyl chlorides to form sulfonamides were added then the reactions were mixed at room temperature. When the reaction showed complete formation of the corresponding 9-amido or 9-sulfamido product (analyzed by silica gel thin layer chromatography, eluent: ethyl acetate:methanol:acetic acid:water; 6:3:3:2, by volume), the mixture was concentrated, reconstituted in water and applied to a silica reversed phase SepPak-C18 column (10 g size) pre-equilibrated in water. The compounds were eluted with a 50 mL gradient of methanol:water (0-80%) and the appropriate fractions containing the product were pooled then concentrated by lyophilization.

The above 9-amido or 9-sulfamido substituted products were in some cases conjugated to PEG-DSPE.

General Procedure for Substitution of the 5 Position of Sialic Acid

Sialoside derivatives containing N-pentenoyl neuraminic acid (Neu5-pentenoyl), including but not limited to Neu5-pentenoylα2-6-galactoseβ1-4-N-acetylglucosamine, Neu5-pentenoylα2-6-galactoseβ1-4-glucose, 9-azido-9-deoxy-Neu5-pentenoylα2-6-galactoseβ1-4-N-acetylglucose, 9-azido-9-deoxy-Neu5-pentenoylα2-6-galactoseβ1-4-N-acetylglucosamine, Neu5-pentenoylα2-3-galactoseβ1-4-N-acetylglucosamine, Neu5-pentenoylα2-3-galactoseβ1-4-glucose, 9-azido-9-deoxy-Neu5-pentenoylα2-3-galactoseβ1-4-N-acetylglucose, 9-azido-9-deoxy-Neu5-pentenoylα2,3-galactoseβ1-4-N-acetylglucosamine (1 eq., 25-50 µmol) were dissolved in a mixture of water-methanol (9:1) with pH adjusted to 3 with 1 M HCl (aq.). Iodine (3 eq.) was added then the reaction was mixed at room temperature. The solution turned from a clear colorless liquid to a cloudy dark red-brown solution. When the reaction showed complete removal of the pentenoyl group to reveal the free 5-amino group (analyzed by silica gel thin layer chromatography, eluent: ethyl acetate:methanol:acetic acid:water; 6:3:3:2, by volume) a solution of sodium thiosulfate (0.1 M aq.) was added until the solution turned from the dark red-brown color to a clear colorless solution. The solution was concentrated, reconstituted in water and the product purified by gel filtration chromatography (Bio-Gel P-2, 1×70 cm, equilibrated in water). The compounds were eluted with water then appropriate fractions containing product were pooled and the sample lyophilized to remove water leaving a white amorphous product. The remaining white solid was dissolved in methanol (1-2 mL) containing diisopropyl-ethylamine (10 eq.). Amine reactive reagents (2 eq) including substituted acyl chlorides or N-hydroxy succinimde activated esters to form amides were added then the reactions were mixed at room temperature. When the reaction showed complete formation of the corresponding 9-amido product (analyzed by silica gel thin layer chromatography, eluent: ethyl acetate:methanol:acetic acid:water; 6:3:3:2, by volume), the mixture was concentrated, reconstituted in water and applied to a silica reversed phase SepPak-C18 column (10 g size) pre-equilibrated in water. The compounds were eluted with a 50 mL gradient of methanol:water (0-80%) and the appropriate fractions containing the product were pooled then concentrated by lyophilization.

The above 5-amido substituted products were in some cases conjugated to PEG-DSPE.

Preparation of Liposomes

Liposomes bearing Siglec ligands such as CD22, CD33, Siglec-5, Siglec-6, Siglec-7, or Siglec-8 ligands can be prepared as described herein and other sources such as WO2012/018377 and WO2007/056525, which are specifically incorporated by reference herein in their entireties.

Distearoyl phosphatidylcholine (DSPC), cholesterol (chol), Distearoyl phosphatidylethanolamine-PEG-Alexa Fluor 647 (DSPE-PEG-AF647), and polyethyleneglycoldistearoyl phosphoethanolamine (PEG-DSPE) derivatives were purchased from Avanti Polar Lipids and NOF Corporation.

Liposomes were composed of a 60:35:5 molar ratio of distearoyl phosphatidylcholine (DSPC) (Avanti Polar Lipids), cholesterol (Sigma-Aldrich), and pegylated lipids. The total molar fraction of pegylated lipids was kept at 5%; made up of the appropriate combination PEG2000-distearoyl phosphoethanolamine where PEG2000 indicates either a polyethylene glycol (PEG-DSPE) (Avanti Polar Lipids) alone or a mixture with siglec-ligand conjugated to PEG2000-DSPE and/or antigen conjugated to-PEG2000-DSPE.

9-substituted-NeuAc-PEG-DSPE was prepared by coupling 9-derivatized-NeuAcα2-6Galβ1-4GlcNAc sialosides with an ethylamine linker to N-hydroxysuccinimide (NHS)-activated pegylated lipids (NOF Corporation). Nontargeted naked liposomes were composed of DSPC:Chol:PEG-DSPE in a 60:35:5 molar ratio.

For preparation of liposomes, lipids dissolved in chloroform and dimethyl sulfoxide were mixed and lyophilized for 16 hours. The lipid flakes were hydrated in the cell culture-grade phosphate-buffered saline (PBS) to achieve a final liposome concentration of 1 to 5 mM (total phospholipids) before extrusion through polycarbonate membrane filters (Millipore) with controlled pore sizes of 0.8, 0.2, and 0.1 μm. To prepare fluorescently labeled liposomes, 0.1 mole % of DSPE-PEG-AF647 was added into the lipid mixture.

Western Blotting

Cells ($3 \times 10^6$/condition) were incubated (37° C., 1 hour) in medium (StemPro-34 culture media (Thermo Fisher) containing the StemPro-34 nutrient supplement as indicated by the manufacturer (Thermo Fisher), glutamine (2 mM), penicillin (100 units/nil), streptomycin (100 μg/ml) prior to stimulating the cells with antigen or liposomes displaying various antigens and/or ligands. Liposomes (2 μM lipid final concentration) or antigen at various concentrations were added to cells.

At 3, 10, or 30 minutes after the cells were incubated with the liposomes (37° C.), the cells were centrifuged (13,000 g, 8 seconds), washed with 4° C. PBS, centrifuged again, and lysed (4° C., 30 minutes) in 200 μl of lysis buffer (20 mM Tris, 150 NaCl, 1 mM EDTA, 1% Triton-X 100, 10 nM NaF, 2 mM sodium orthovanadate, protease inhibitor cocktail [Roche], pH 7.5), Cell debris was removed by centrifugation (13,000 g, 10 minutes, 4° C.). Cleared supernatant was denatured with LDS-PAGE loading buffer (Life, technologies) and 250 mM DTT (95° C., 10 minutes).

Samples were run on 4%-12% gradient SDS-PAGE gels (Invitrogen) and transferred to nitrocellulose. Membranes were blocked (RT, 1 hour) in 5% nonfat milk powder dissolved in PBS-T and probed with primary antibody (overnight, 4° C.) in PBS-f containing 1% BSA. The next day, membranes were washed (4×5 minutes), blocked (30 minutes, RT), and probed (1 hour, RT) with secondary HRP-conjugated antibodies (1:2000 dilution; Cell Signaling Inc.). Following 4 washes, blots were incubated (2 minutes, RT) with developing solution (GE Healthcare) and exposed to film.

Calcium Flux

Calcium flux was employed as a measure of antigen-induced signaling of mast cell activation/degranulation. Calcium flux was measured using Indo-1 (Invitrogen), a calcium binding dye by suspending $15 \times 10^6$ LAD2 cells/ad in RPMI (Gibco), 1% FCS, 10 mM HEPES, 1 mM MgCl2, 1 mM EGTA and 1.5 uM Indo-1. Cells were incubated in a 37° C. water incubator for 30 minutes. Following incubation (37° C., 30 minutes), a 5-fold volume of the same buffer (without Indo-1) was added and the cells were centrifuged (270 g, 7 minutes). Cells were washed and resuspended at a concentration of $2 \times 10^6$ cells/nil in HBSS containing 1% FCS, 1 mM $MgCl_2$, and 1 mM $CaCl_2$. Cells were stored on ice, and an aliquot (0.5 ml; $1 \times 10^6$ cells) was warmed (37° C., 5 minutes) prior to initiating calcium flux measurements. Cells were stimulated with liposomes (ranging from 0.2 to 5 μM), and Indo-1 fluorescence (violet vs. blue) was monitored by flow cytometry (500-1000 events/s) for 3 minutes at 37° C. Stimulation took place 10 seconds after starting acquisition so that background could be established. Data were analyzed using FlowJo using the kinetics functions.

β-hexosaminidase Assay

Degranulation of the LAD2 mast cells, human CD33 expressing bone marrow derived mast cells (BMMCs), and Siglec-8 expressing bone marrow derived mast cells (BMMCs) was measured by release of beta-hexosaminidase. LAD2 mast cells and hCD33/Siglec-8 expressing bone marrow derived mast cells (10,000 cells or 30,000 cells, respectively) were loaded with anti-TNT IgE (0.5 ug/mL and 2 ug/mL respectively, Biolegend, Clone MER-38) overnight in 96 well plate. 16 hours later, after the cells were washed with Tyrode's buffer (HBSS containing 5 mM HEPES, 1 mM $CaCl_2$, 1 mM $MgSO_4$ and 0.1% BSA), the cells were incubated with liposomes that display only the TNP antigen, or with liposomes displaying both the TNP antigen and the CD33 ligand in Tyrode's buffer, Anti-CD33 antibody was added to a subset of wells containing LAD2 cells to test whether anti-CD33 antibody blocked CD33 ligand-mediated binding to the cells. The plates were spun at 300×g, at 4° C. for 5 min to stop the reaction and to ensure the cells are sedimented to the base of the wells. Fifty microliters of cell supernatant was added to 100 μl of a citric acid buffer (pH 4.5) containing 4 mM p-nitrophenyl N-acetyl-β-D-glucosamide (PNAG), and the mixture was incubated for 90 minutes at 37° C. Fifty μl 0.4 M Glycine buffer (400 mM; pH 10.7) was added, and the absorbance at 405 nM was read.

To calculate the total β-hexosaminidase activity, 150 μl of 0.1% Triton X-100 solution was added to the 50 μl of supernatant and cells remaining in the original incubation plate. The cells were carefully resuspended and 50 μl of lysate was added to 100 μl of the PNAG solution. The mixtures were incubated for 90 min at 37° C. Fifty μl 0.4 M glycine buffer (400 mM; pH 10.7) was added, and the absorbance at 405 nM was read. The percentage of β-hexosaminidase activity in the supernatant relative to the total β-hexosaminidase activity is a measure of LAD2 mast cell degranulation.

Example 2: Siglec Expression on Human Mast Cells

Mast cells were identified using flow cytometry as high forward side scatter ($FSC^{high}$) and high side scatter ($SSC^{high}$) cells. Mast cells obtained from human donors were further characterized by the following expression pattern: $CD45^+CD19^-CD3^-CD56^-CD11b^{low}$ c-kit$^{high}$ FcεRI$^+$, as illustrated in FIG. 2A-1. Overlays of antibody signal against hCD33 (rightmost peak) and isotype control (left diffuse peak) for mast cells are shown in FIG. 2A-2.

FIG. 2B graphically illustrates Siglec expression profiles of human skin mast cells from ten independent donors. As illustrated, hCD22, hCD33 (Siglec-3), Siglec-5, Siglec-6, Siglec-7 and Siglec-8 are constitutively expressed at significant levels in human mast cells. FIG. 2C further graphically illustrates Siglec-3 and Siglec-8 expression levels on human skin mast cells from ten independent donors.

Example 3: Synthetic Ligands for Human CD33 and Siglec-8

FIG. 3 shows a schematic diagram of a liposome (left) presenting ligands (diamond symbols) on its surface. Also shown in FIG. 3 are structures of synthetic ligands (top right, CD33L) developed for human Siglec-3 (also called CD33) as well as synthetic ligands for human Siglec-8 (bottom right, Sig8L, CN146).

Example 4: STAL Co-Displaying Antigen and hCD33-Ligand Suppresses Antigen Induced Mast Cell Activation/Degranulation This Example illustrates suppression of anti-antigen-IgE mediated LAD2 degranulation by liposomes that co-present antigen and ligand to CD33 (CD33L).

Methods

Antigens employed included Ara h 2 (Ah2), which is one of the dominant protein antigens involved in peanut allergy, ovalbumin, which is a protein involved in egg allergy, and a small molecule hapten 2,4,6-trinitrophenyl (TNP).

Mast cells (LAD2 cells) were pre-sensitized with IgE reactive to hapten TNP, ovalbumin, or to the peanut Ah2 antigen. Cells are then incubated with liposomes that display only antigen, or with liposomes displaying both antigen and CD33 Such antigen and Siglec ligand displaying liposomes are referred to as SIGLEC-engaging tolerance-inducing antigenic liposomes (STALs). Depending on the antigen and the corresponding Siglec-ligand, these tolerizing particles are referred to in abbreviated form as antigen-STAT, (Siglec-ligand). For example, liposomes co-displaying hapten TNP and human CD33 ligand are referred to as TNP-STAL (hCD33L). Liposomes co-displaying ovalbumin (OVA) and hCD33-ligand are referred to as OVA-STAL (hCD33L). Liposomes co-displaying Ara h 2 and hCD33-ligand are referred to as Ah2-STAL (hCD33L).

Results

Figure 4F:
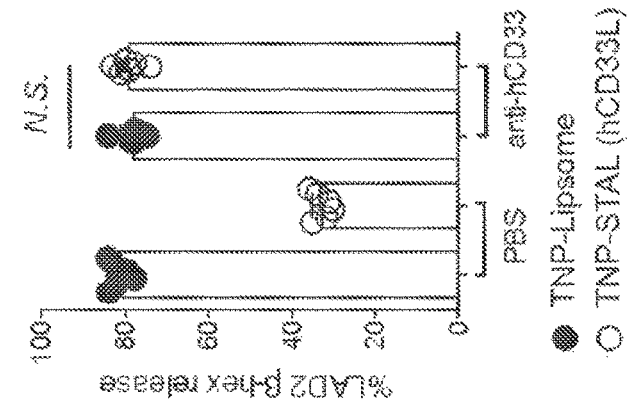
FIG. 4A illustrates that liposomes displaying both the TNP antigen and the CD33 ligand (TNP-STAL/hCD33L; where STALs are SIGLEC-engaging tolerance-inducing antigenic liposomes) suppress TNP-induced calcium flux in LAD2 cells pre-sensitized with anti-TNP-IgE compared to liposomes that display only the antigen (TNP-lip).
FIG. 4B graphically illustrates that LAD2 cells primed with anti-TNP-IgE fail to degranulate when exposed to liposomes displaying both the TNP antigen and the CD33 ligand (TNP-STAL/hCD33L, open symbols) as detected by β-hexosaminidase release, in comparison to LAD2 cells that undergo strong degranulation to liposomes that display only the antigen (TNP only, closed symbols).
FIG. 4C graphically illustrates that liposomes that display both the major peanut allergen Ara h 2 and the CD33 ligand (Ah2-STAL/hCD33L, open symbols) fail to induce degranulation of LAD2 cells that have been pre-sensitized with antisera obtained from patients with peanut allergies. However presence of the CD33L on the liposomes and hCD33 expression on the mast cells. Moreover, prior treatment of liposomes co-displaying TNP and hCD33L completely desensitizes hCD33 transgenic mice from a subsequent challenge with antigen.
Figures 2, 4E:
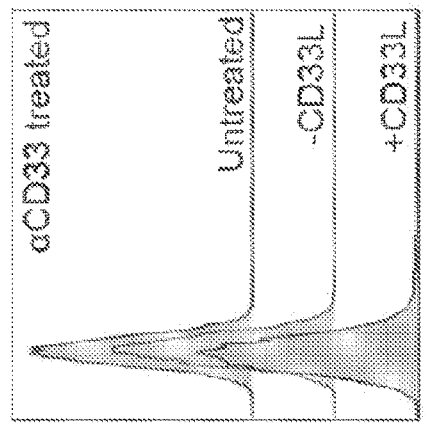
Figures 1, 4E:
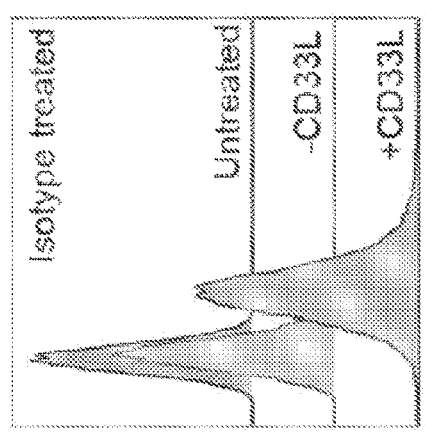
FIG. 1 schematically illustrates that antigen-induced degranulation of mast cells (left) is suppressed by co-presentation of the antigen (star-shaped symbol) with exemplary mast cell Siglec ligands (e.g., CD33 or Siglec-8 ligands shown as diamond-shaped symbols) on a carrier such containing both the antigen and a ligand to CD33 (CD33L).

As illustrated in FIG. 4A, the TNP-STAL (hCD33L) do not stimulate TNP-induced calcium flux in LAD2 cells that had been pre-sensitized with anti-TNP-IgE. On the other hand, liposomes displaying only TNP (TNP-lip) do stimulate TNP-induced calcium flux in LAD2 cells pre-sensitized with anti-TNP-IgE. FIG. 4B graphically illustrates that the presence of the hCD33L on TNP-STALs (hCD33L) suppressed anti-TNP-IgE mediated LAD2 degranulation as determined by β-hexosaminidase release. Likewise, FIG. 4C shows that the CD33L on Ah2-STAL (hCD33L) suppressed Ah2-mediated degranulation of LAD2 cells that had been pre-sensitized with antisera of patient allergy patients. Furthermore, FIG. 4D illustrates that hCD33L on OVA-STAL (hCD33L) suppresses Ovalbumin induced LAD2 degranulation of LAD2 cells that had been sensitized with anti-OVA human IgE. FIG. 4E graphically illustrates binding of fluorescent liposomes to LAD2 cells as detected by flow cytometry. A CD33-blocking antibody (Clone WM53) blocked CD33L mediated liposome binding to LAD2 cells as illustrated by FIGS. 4E-1 and 4E-2. Pre-treatment of LAD2 cells with antibodies against CD33 (αCD33, clone WM53) abrogated CD33L-mediated inhibition of LAD2 cell degranulation as illustrated by FIGS. 4E-2 and 4F (difference determined unpaired t test).

Figure 5A:
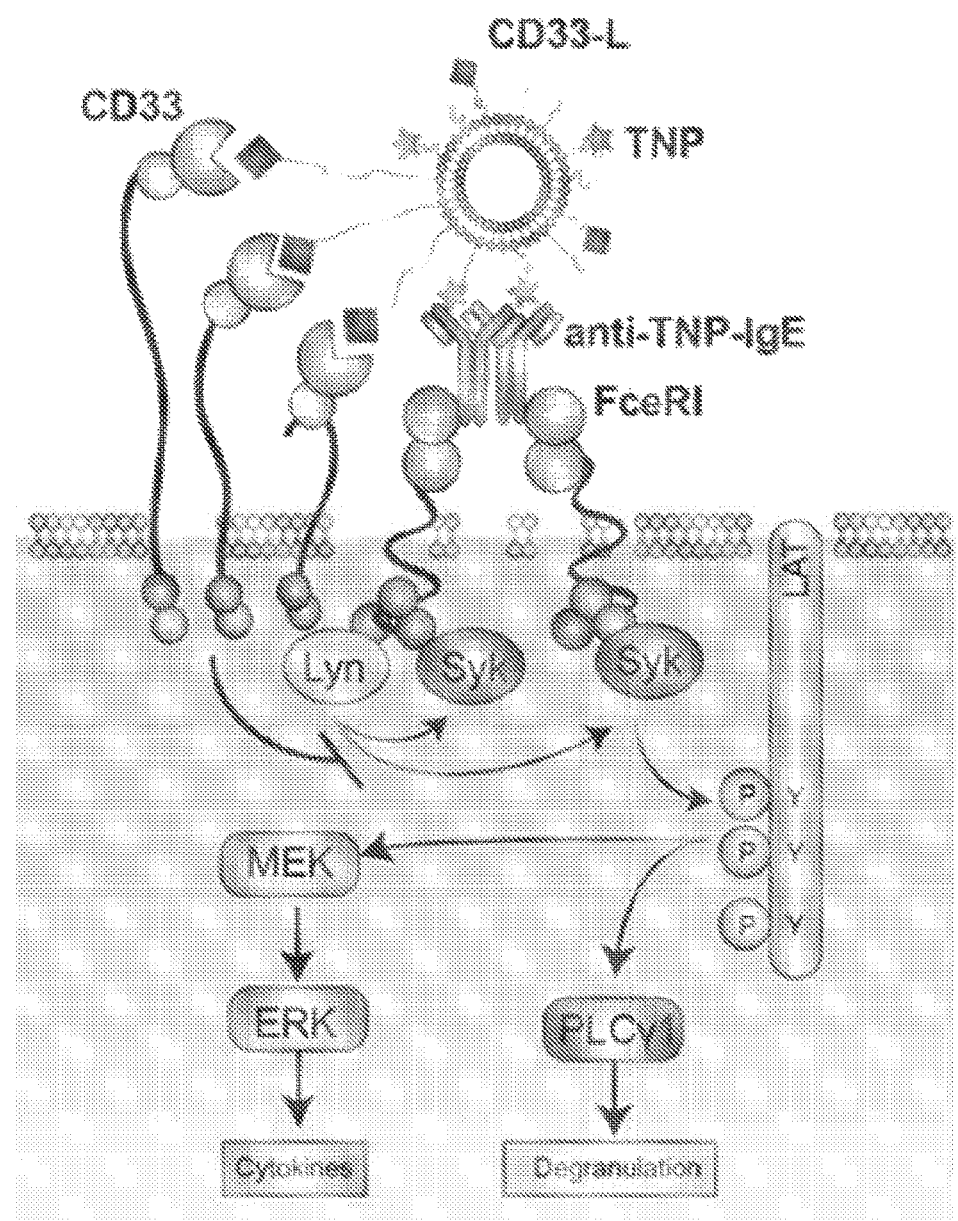

Example 5: Co-Presentation of Antigen and CD33 Ligand Disrupts FcεRI Signaling in LAD2 Cells LAD2 human mast cells, which were sensitized with anti-TNP IgE, were cultured with no liposomes, or with liposomes containing only antigen (2,4,6-trinitrophenyl, TNP), or with liposomes presenting both the TNP antigen and hCD33L. FIG. 5A shows a schematic diagram of a structure of a liposome that can be employed, displaying an antigen (TNP; star symbol) and a CD33 ligand (diamond symbols) on the liposomal surface.

Western blots were prepared of proteins isolated from the LAD2 cells following such treatments, and the blots were stained with antibodies that recognize signaling molecules Syk and Erk 1/2, and with antibodies for phosphorylated signaling molecules (P-Syk, P-PLCg1, P-MEK and P-Erk).

Figure 5B:
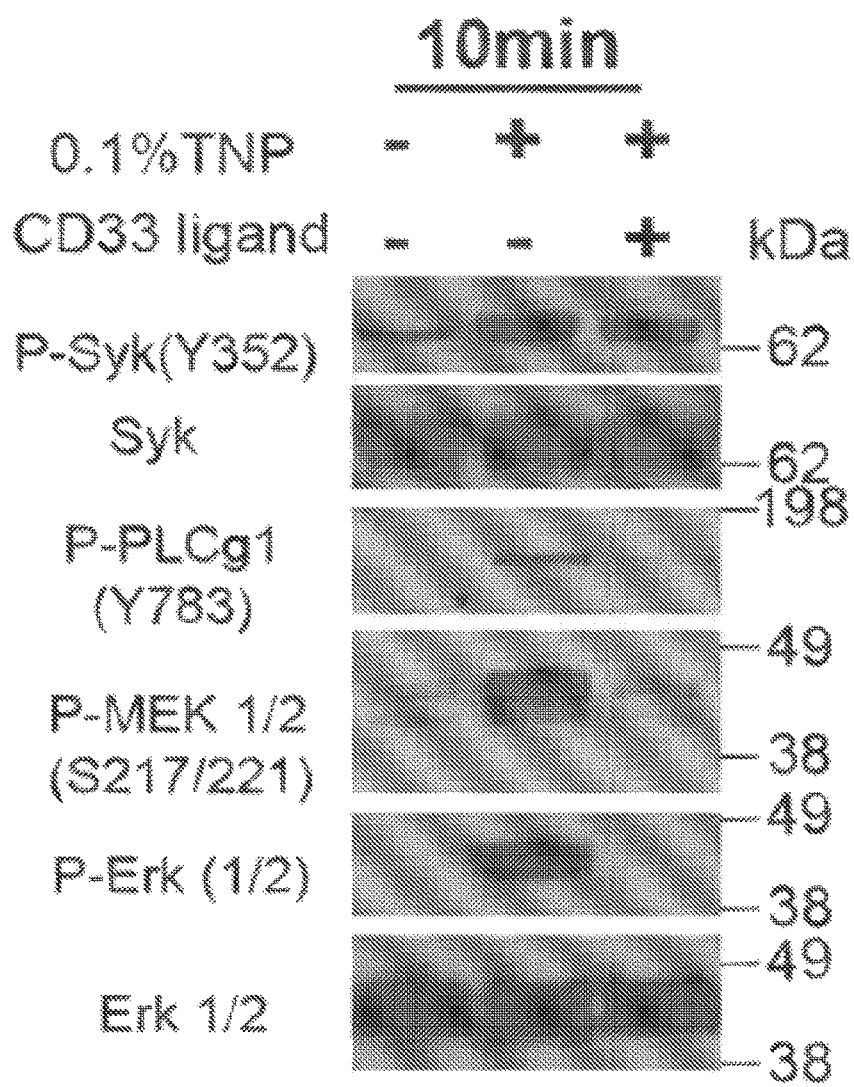

As illustrated by the image of such a western blot (FIG. 5B), the presence of the CD33 ligand dramatically suppresses the phosphorylation of these signaling molecules.

Incubation of mast cells with both the TNP antigen and the CD33 ligand resulted in enforced ligation of CD33 to FcεRI, which disrupts FcεRI signaling cascade critical for degranulation (PLCγ1) and inflammatory cytokine production (MEK and ERK) in LAD2 cells (see schematic diagram in FIG. 5A).

Example 6: Liposomes Displaying Antigen and Siglec-3 (CD33) Ligands Desensitize Mast Cells to Subsequent Antigen Challenge This Example illustrates that mast cells incubated with liposomes displaying both the TNP antigen and the CD33 ligand are desensitized against subsequent antigen challenge.

Methods

LAD2 mast cells were incubated with PBS, liposomes displaying both the TNP antigen and the Siglec-3 (CD33) ligand (TNP-STALs/hCD33L), or liposomes displaying only the TNP antigen (TNP-liposomes). Degranulation of the cells was measured by release of beta-hexosaminidase as described in previous Examples.

Aliquots of these cells were then washed and challenged with TNP-BSA, or recharged with anti-TNP IgE, overnight and then challenged with TNP-BSA. Differences determined by unpaired t test.

Results

Figure 6A:
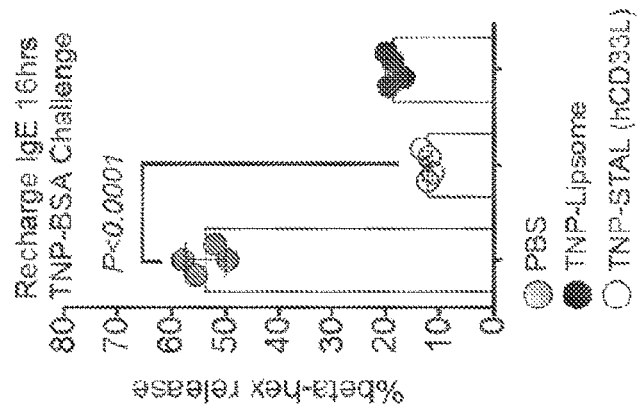

FIG. 6A graphically illustrates that LAD2 mast cells treated with liposomes displaying both the TNP antigen and the CD33 ligand (TNP-STALs) exhibited significantly less degranulation than LAD2 mast cells treated with liposomes displaying only antigen. The LAD2 mast cells treated with liposomes displaying both the TNP antigen and the CD33 ligand (TNP-STAL/hCD33L) exhibited no more degranulation than LAD2 mast cells treated with only PBS.

Figure 6B:
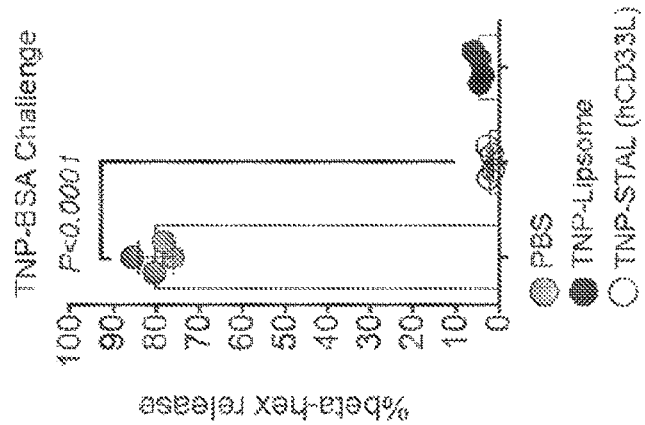

FIG. 6B graphically illustrates beta-hexosaminidase release of the same cells after washing and treatment with liposomes displaying both the TNP antigen and the CD33 ligand (TNP-STALs as described for FIG. 6A), followed by challenge with TNP coupled to the carrier protein BSA (TNP-BSA). As shown, after challenge with TNP-BSA, LAD2 mast cells incubated with only PBS exhibited significant degranulation, but LAD2 mast cells incubated with liposomes displaying both the TNP antigen and the CD33 ligand (TNP-STAL/hCD33L) or with the liposomes displaying only the TNP antigen (TNP-liposomes) exhibited little or no beta-hexosaminidase release. Hence, PBS treated cells responded to TNP-BSA with release of beta-hexosaminidase but prior exposure to liposomes displaying both the TNP antigen and the CD33 ligand (TNP-STALs) desensitized the mast cells and inhibited beta-hexosaminidase release.

Figure 6C:
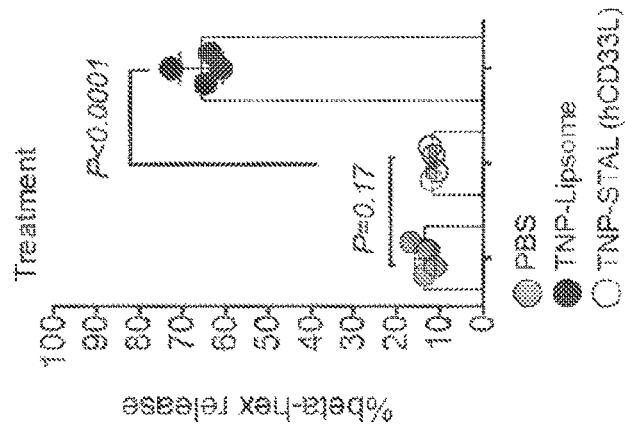

Aliquots of cells treated with liposomes displaying both the TNP antigen and the CD33 ligand (TNP-STALs as described for FIG. 6A) were washed, recharged with anti-TNP IgE overnight, and then challenged with TNP-BSA. As shown in FIG. 6C, after challenge with TNP-BSA, LAD2 mast cells treated with only PBS exhibited significant degranulation, but LAD2 mast cells incubated with liposomes displaying both the TNP antigen and the CD33 ligand (TNP-STAL/hCD33L) or with the liposomes displaying only the TNP antigen (TNP-liposomes) exhibited little or no beta-hexosaminidase release.). Hence, pre-treatment with liposomes displaying both the TNP antigen and the CD33 ligand (TNP-STALs) desensitizes the mast cells and inhibits degranulation when the cells are later challenged with antigen, even if the TNP-STALs have been removed by washing the mast cells.

Example 7: Characterization of Transgenic Mice that Conditionally Express Human CD33 on Mast Cells This Example illustrates experiments carried out with human CD33 transgenic mice, as well as flow cytometry analysis of mast cells harvested from these mice.
Methods
A cDNA encoding human CD33 (hCD33) was subcloned into the CTV vector and used to transfect C57BL/6 embryonic stem (ES) cells. This vector contains homology sites to allow insertion of the vector into the ROSA-26 ($R_{26}$) locus through homologous recombination. Another feature of this vector is that is contains a $STOP^{flx/flx}$ sequence upstream of the hCD33 that enables the gene to be expressed in a Cre recombinase-dependent manner. Clones of ES cells that had successfully integrated specifically into the $R_{26}$ locus were selected by PCR analysis. Positively selected clones were injected into a blastocyst derived from a C57BL/6J mice, and implanted into C57BL/6J-albino mice. Black pups were selected and further bred to C57BL/6J-albino female mice again. Pups having germline line transmission of hCD33, as determined by PCR analysis from tail snips, were further bred to expand this transgenic mouse line. To conditionally express human CD33 on murine mast cells, the Rosa26-hCD33 mice were bred to mice bearing MCPT5-Cre, which drives Cre recombinase selectively in mast cells. The resulting pups expressing both MCPT5-Cre and Rosa25-hCD33 were selected by PCR and were used for experiments as hCD33-Tg mice.

Figures 1, 2, 7B:
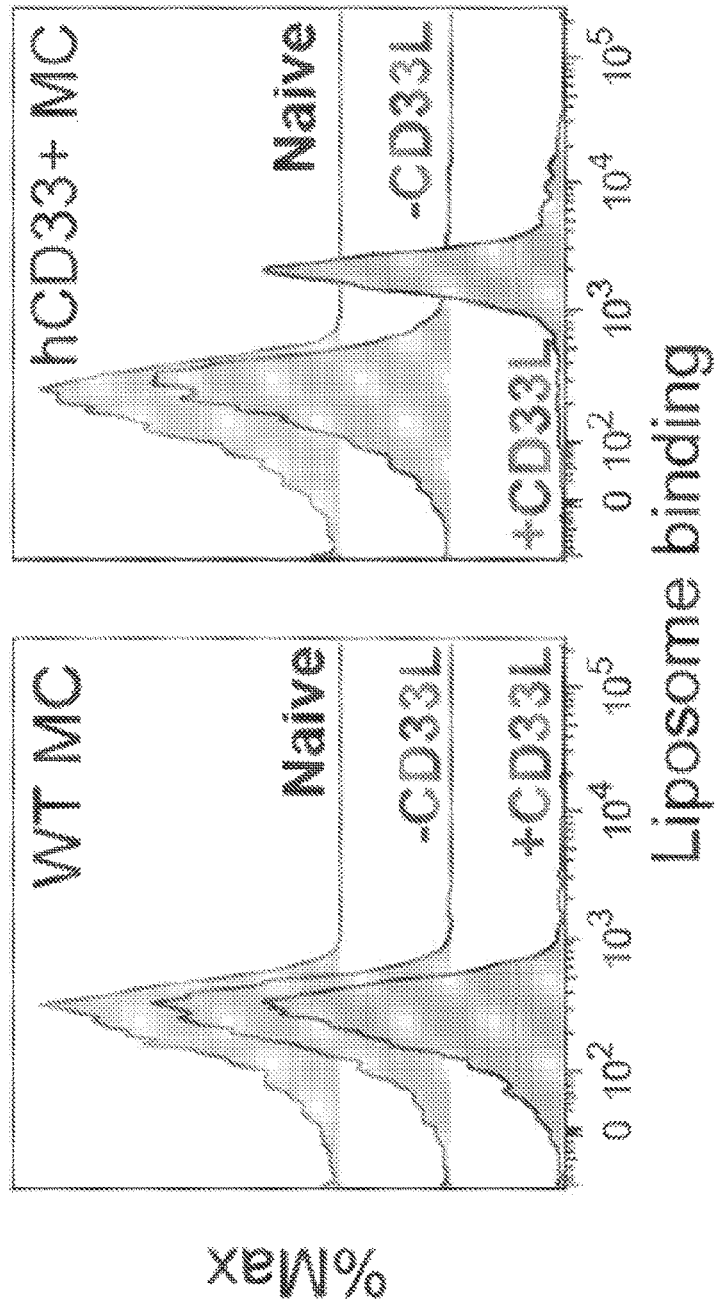

Liposome binding was evaluated by separately testing peritoneal fluid harvested from WT mice and peritoneal fluid harvested from hCD33-Tg, mice by incubation with fluorescent liposomes bearing no ligand or fluorescent liposomes bearing hCD33L at a final lipid concentration of 20 uM at 37° C. for 1 hour. Cells were then washed and stained using antibody against mouse CD45, mouse c-Kit, and human CD33. Cells were analyzed by flow cytometry.
Results
FIG. 7A illustrates that murine peritoneal mast cells exhibit expression of CD45 and cKit (i.e., the cells are CD45+cKit+ cells). Mast cells from WT mice do not express human CD33. Only mast cells from the hCD33-Tg mice express human CD33, as detected by anti-human CD33 antibody (Clone WM53) (compare FIGS. 7A-1 and 7A-2). FIG. 7B-1 illustrates that mast cells front WT mice do not bind to any fluorescent liposomes whether the liposomes display the human CD33 ligand or not. As illustrated, cells exhibit flow cytometry patterns like the untreated control (naïve) mast cells even if the liposomes display human CD33 ligand (+CD33L). In contrast, transgenic human CD33+ peritoneal mast cells bind to fluorescent liposomes bearing human CD33 ligand (FIG. 7B-2).

Example 8: Suppression of TNP-Induced Degranulation with Ligands of hCD33

This Example illustrates that liposomes co-displaying TNP and human CD33 ligand do not stimulate TNP-induced degranulation and pro-inflammatory cytokine production in bone marrow derived mast cells (BMMC) from the human CD33 transgenic (Tg) mice.
Methods
Bone marrow was isolated from hCD33 Tg mice, and the bone marrow cells were cultured for several weeks in WEHI-3 conditioned medium as a source of IL-3. The media also contained 1% antibiotic/antimycotic, $5 \times 10^{-5}$ M β-mercaptoethanol, 2 mM L-glutamine; 10% fetal bovine serum (heat-inactivated). The cells were transferred to new flasks containing fresh culture medium every 3-4 days.

Degranulation of bone marrow derived mast cells was measured by release of beta-hexosaminidase as described in previous Examples. To evaluate cytokine production, bone marrow was isolated from hCD33-Tg sensitized in culture with anti-TNP IgE (MEB-38) at 1 μg/mL. Sixteen hours after sensitization, the BMMCs were washed with culture media. Cells were then incubated with liposomes displaying TNP antigen alone, liposomes co-displaying TNP-antigen with CD33L (TNP-STAL/hCD33L) ligand, or liposomes displaying hCD33L only at a final lipid concentration at 45 uM. Eight hours later, the supernatant was harvested and the concentration of mouse IL13, IL6 and TNF-alpha was determined using an ELISA kit (Biolegend).
Results
FIG. 8A illustrates that liposomes bearing TNP only (TNP-Lip) strongly induced degranulation of human CD33+ bone marrow derived mast cells (BMMCs) as quantified by beta-hexosaminidase release. Liposomes co-displaying TNP and human CD33 ligand (TNP-STALs/hCD33L) strongly inhibited the release of beta-hexosaminidase. FIG. 8B-8D illustrate that liposomes bearing TNP alone (TNP-Lip) strongly induced production of pro-inflammatory cytokines including TNFα, IL-6 and IL-13. Liposomes co-displaying TNP and hCD33 ligand (TNP-STAL/hCD33L) profoundly inhibit production of TNFα, IL6, and IL-13. Liposomes bearing hCD33L only do not induce production of TNFα, IL6, or IL-13. Hence, while display of an antigen on a carrier induced mast cell degranulation and production of pro-inflammatory cytokines, when the carrier also displayed a CD33 ligand with the antigen, essentially no mast cell degranulation and no production of pro-inflammatory cytokines is observed.

Example 9: Suppression of TNP-Induced Anaphylaxis in hCD33 Transgenic Mice Using Ligands of hCD33

This Example illustrates that liposomes co-displaying TNP and human CD33 ligand (TNP-STAL/hCD33L) strongly inhibit TNP-induced systemic anaphylaxis in the hCD33-Transgenic mice but not in WT mice using a passive systemic anaphylaxis model to detect such anaphylaxis. This example also demonstrates that these TNP-STAL (hCD33L) desensitize hCD33-Tg mice from a subsequent antigen challenge.

Methods

WT or hCD33-Tg mice were intravenously sensitized on day 0 with 10 ug of murine anti-TNP-IgE (Biolegend, Clone MEB-38) on day 0. On day 1, mice were intravenously treated with 150 ug of liposomes displaying TNP only (TNP lip) or liposomes co-displaying TNP and human CD33L (TNP-STAL/hCD33L). Rectal temperatures were monitored for 1 hour as a measure of systemic anaphylaxis. FIG. 9A for a schematic diagram of the method for inducing systemic anaphylaxis.

Figure 9C:
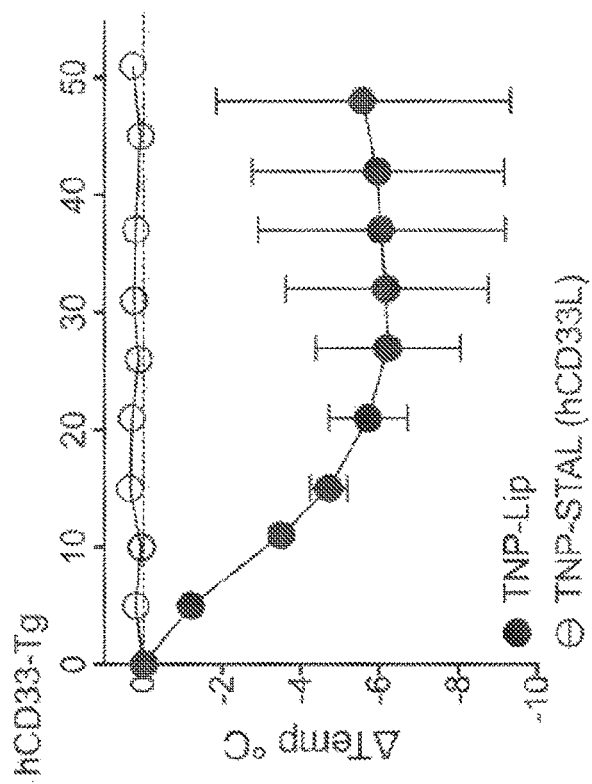
FIG. 9C shows results of sensitizing hCD33-transgenic mice with anti-TNP-mouse IgE followed by treatment with TNP-liposomes or TNP-STAL (hCD33L; open circles). Human CD33 transgenic mice developed severe anaphylaxis when given just the TNP-liposomes (black circles) in the same similar as wild type mice. In contrast, anaphylaxis was not observed in hCD33-transgenic mice treated with liposomes co-displaying TNP and hCD33L (TNP-STAL/hCD33L, open circles).
Figure 9B:
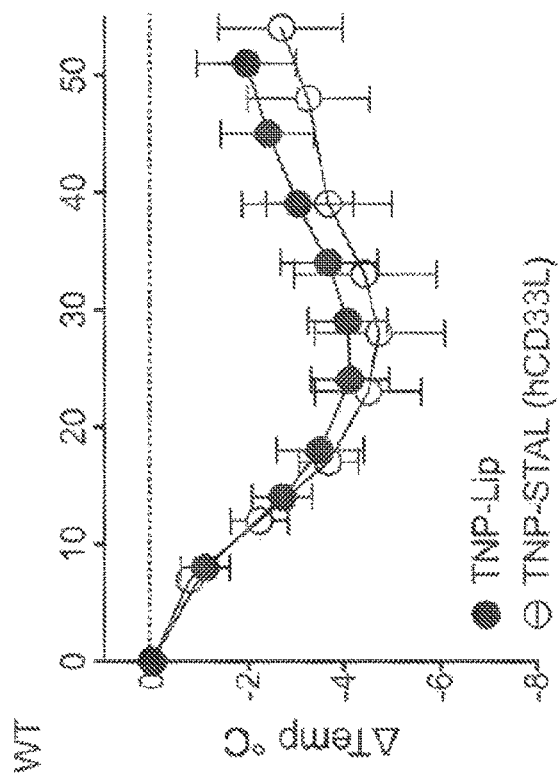
FIG. 9B shows results of sensitizing wild type mice with anti-TNP-IgE followed by administration of liposomes displaying TNP-Only (TNP-Lip, black symbols) or liposomes co-displaying TNP and hCD33L (TNP-STAL/hCD33L; open symbols). Wild type mice are mice that do not express human CD33 (or any other Siglecs). Both TNP-liposome and TNP-STAL (hCD33L) strongly induced systemic anaphylaxis as quantified by drop of rectal temperature.

For desensitization experiments, hCD33-Tg were intravenously sensitized with 10 ug of murine anti-TNP-IgE (Biolegend, Clone MEB-38) on day 0. On day 1, mice were intravenously treated with PBS or 450 ug of liposomes co-displaying TNP and human CD33 ligand (TNP-STAL/hCD33L). Rectal temperatures were monitored for 40 minutes. Six hours after treatment, all mice were challenged with 45 ug of liposomes displaying TNP only. Rectal temperatures were monitored for another 60 minutes, See Results Anaphylaxis. FIG. 9B illustrates that administration of 150 ug of both TNP-liposomes and TNP-STALs (hCD33L) to WT mice, which do not express human CD33, induced significant reduction in body temperature. FIG. 9C illustrates that hCD33-Tg mice develop severe anaphylaxis when given 150 ug of liposomes displaying TNP-Only (TNP-lip). However, liposomes co-displaying TNP and hCD33L (TNP-STAL/hCD33L) completely protected the hCD33-Tg mice from any drop of body temperature (FIG. 9C).

Desensitization. FIG. 9D illustrates that, when the hCD33-Tg mice were treated with 450 mm of TNP-STAL (hCD33L) intravenously, no drop of rectal temperature was detected compared to PBS control. Six hours later, when all mice were challenged with 45 ug of liposomes displaying TNP-only, mice previously received PBS now developed severe anaphylaxis (FIG. 9E). In contrast, the mice that were treated with TNP-STAL (hCD33L) are protected from the effects of antigenic challenge (FIG. 9E).

Example 10: Suppression of Anti-TNP-IgE Mediated Cell Degranulation with Ligands of Siglec-8

This Example illustrates binding by the CN146 Siglec-8 ligand to cells that express Siglec-8, and inhibition of cellular degranulation after exposure of those cells to the CN146 Siglec-8 ligand. Specifically, when the Siglec-8-expressing cells are pre-sensitized to anti-TNP IgE antigen, and when these cells are incubated with liposomal nanoparticles containing both the TNP antigen and the CN146 Siglec-8 ligand, degranulation of the cells is suppressed.

Methods

Rat basophilic leukemia (RBL) cells were transfected with an expression cassette encoding human Siglec-8 to generate transgenic RBL cell lines. Stable expression of Siglec-8 expression was confirmed in selected transgenic RBL cell lines. RBL cells that expressed Siglec-8 were incubated with the Siglec-8 ligand CN146 (structure shown in FIG. 3).

Binding of the CN146 ligand displayed on fluorescent liposomal nanoparticles to Siglec-8 expressing RBLs was detected by flow cytometry. Degranulation of the cells was measured by release of beta-hexosaminidase as described in previous Examples. Differences were determined by unpaired t tests.

Results

Figure 10B:
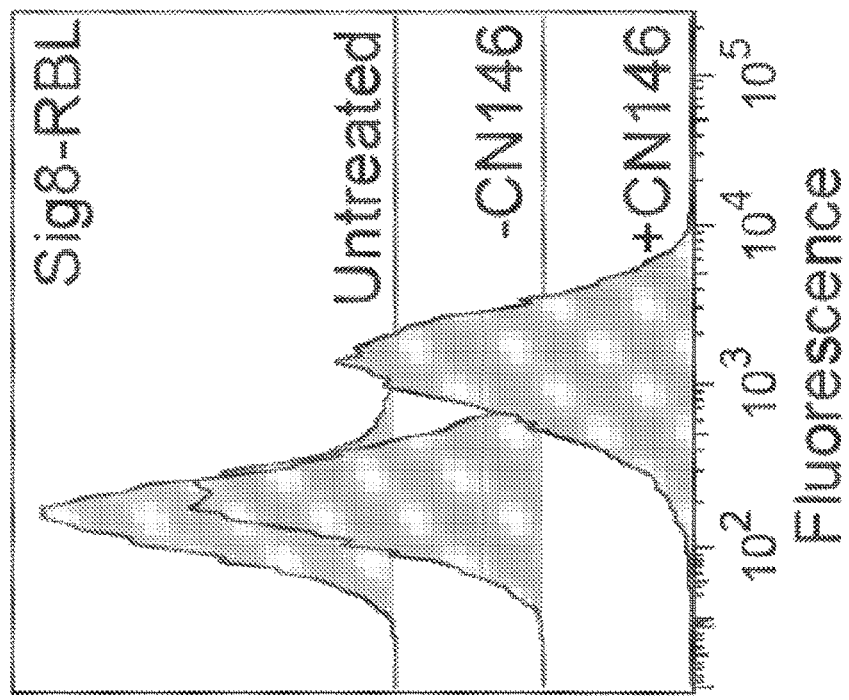
FIG. 10A-10D illustrate that liposomes displaying both antigen and Siglec-8 (CN146) ligands inhibit degranulation of rat basophilic leukemia cells (RBL cells).
Figure 10A:
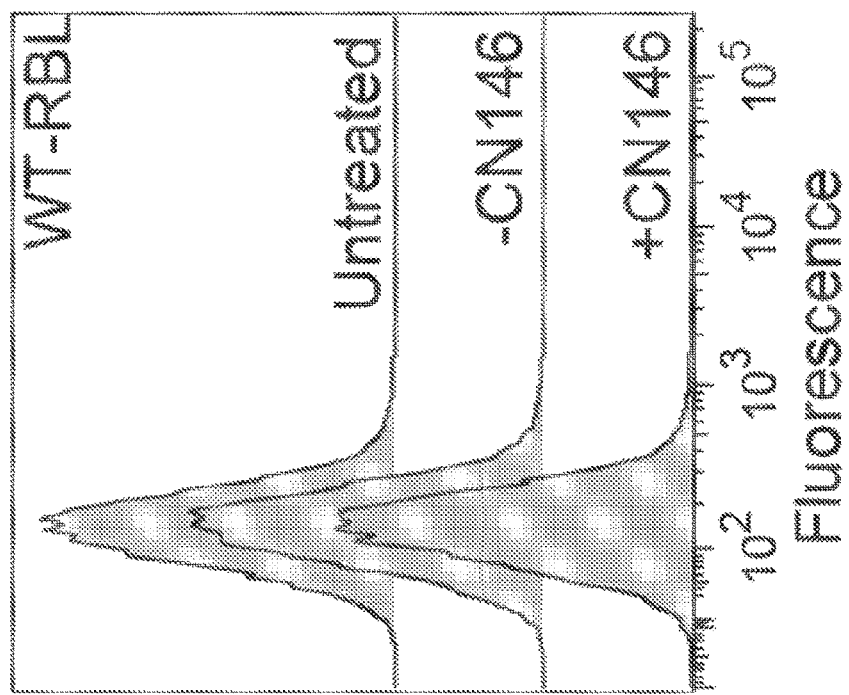
Figure 10C:
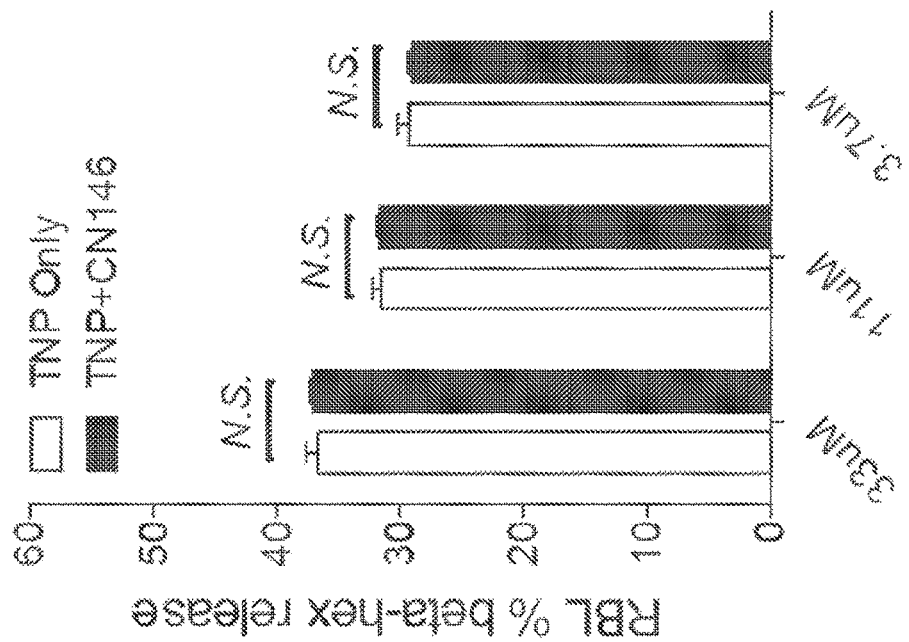
Figure 10D:
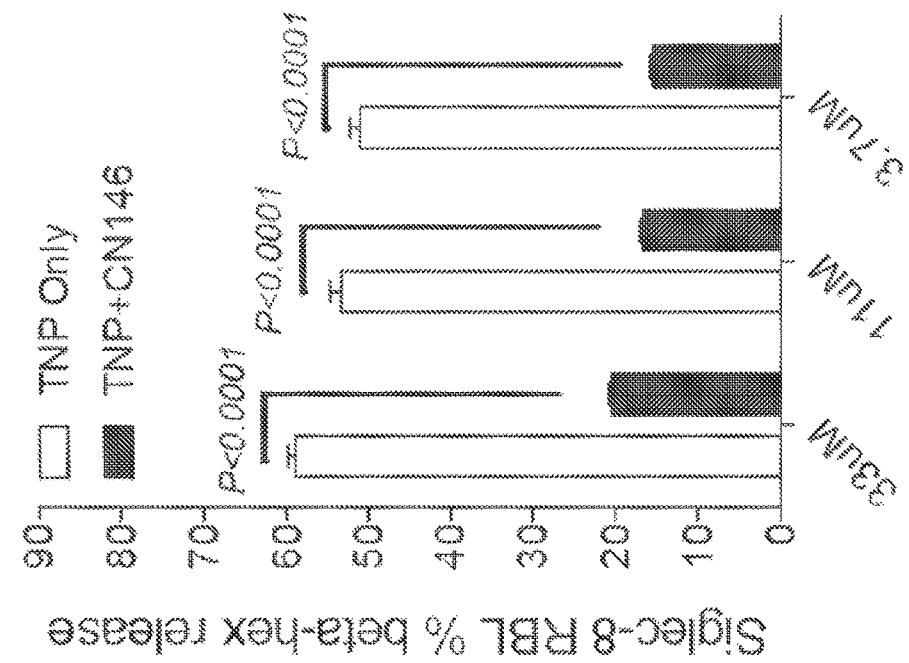

As illustrated in FIG. 10B, fluorescent liposomes displaying the Siglec-8 ligand (CN146) bind to Siglec-8 transfected rat basophilic leukemia (RBL) cells. However, fluorescent liposomes displaying the Siglec-8 ligand (CN146) do not bind to non-transfected RBL cells (FIG. 10A). In addition, liposomes displaying the TNP antigen and the Siglec-8 ligand (CN146) do not induce degranulation of αTNP-IgE pre-sensitized RBL cells expressing Siglec-8 as illustrated by FIG. 10C. Non-transfected RBL cells, which do not express Siglec-8, did not exhibit reduced degranulation after incubation with the antigen and the Siglec-8 ligand (CN146) as illustrated in FIG. 10D.

Example 11: Characterization of Transgenic Mice that Conditionally Express Human Siglec-8 on Mast Cells This Example illustrates expression of human Siglec-8 on murine peritoneal mast cells from Siglec-8 Tg mice but not those from WT mice. Fluorescent liposomes bearing Siglec-8 ligand binds to Siglec-8+ peritoneal mast cells but not WI mast cells.

Methods

Siglec-8 transgenic mice (Sig8$^+$) were obtained from. Zhou Ziru (Yale University), which were generated by microinjection of a human Siglec-8 transgene into one or both pronuclei of zygote-stage embryos. Analogous to the ROSA26-hCD33 transgenic mice, the cDNA encoding human Siglec-8 was inserted to the Rosa26-locus through homologous recombination. Clones that had the Siglec-8 transgene successfully integrated into the ROSA26 locus were selected by PCR analysis and surgically transferred into pseudo-pregnant recipient females. To conditionally express Siglec-8 on mast cells, the ROSA26-Siglec-8 mice were crossed to mice bearing MCPT5-Cre. The resulting mice are Siglec-8 transgenic mice, which express the Siglec-8 transgene only in the mast cell lineage. These transgenic mice that express Siglec-8 are referred to as Siglec-8-Tg mice.

Liposome binding was evaluated by separately incubating peritoneal fluid harvested from WT mice or Siglec-8-Tg mice with fluorescent liposomes bearing no ligand or with fluorescent liposomes bearing Siglec-8 ligand at a final lipid concentration of 20 uM at 37° C. for 1 hour. Cells were then washed and stained using antibody against mouse CD45, mouse c-Kit, and Siglec-8. Cells were analyzed by flow cytometry.

Results

FIG. 11A illustrates that murine peritoneal mast cells (which express CD45 and cKit and are therefore CD45+cKit+ mast cells) from WT mice do not express human Siglec-8. Mast cells, and only mast cells, from the Siglec-8-Tg mice express human Siglec-8 as detected by anti-human Siglec-8 antibody on the CD45+cKit+ population (FIG. 11B). FIG. 11C illustrates that mast cells from WT mice do not bind to fluorescent liposomes whether or not Siglec-8 ligand is displayed by the liposomes. In other words, mast cells from WT mice exhibit flow cytometry patterns like untreated control cells. In contrast, FIG. 11D shows that Siglec-8+ peritoneal mast cells bind to fluorescent liposomes bearing human Siglec-8 ligand (+Sig8L), but not liposomes with no ligand (-Sig8L).

Example 12: Suppression of TNP-Induced Degranulation with Ligands of Siglec-8 In Vitro This Example illustrates that the liposomes co-displaying TNP and Siglec-8 ligand do not stimulate TNP-induced degranulation and pro-inflammatory cytokine production in bone marrow derived mast cells (BMMC) from the Siglec-8 Tg mice.

Methods

Bone marrow was isolated from Siglec-8 Tg mice, and the bone marrow cells were cultured for several weeks in WEHI-3 conditioned medium as a source of IL-3. The media also contained 1% antibiotic/antimycotic; $5 \times 10^{-5}$ M β-mercaptoethanol; 2 mM L-glutamine; 10% fetal bovine serum (heat-inactivated). The cells were transferred to new flasks containing fresh culture medium every 3-4 days.

To evaluate cytokine production, bone marrow was isolated from Siglec-8 knock-in mice and the Sig8 BMMCs were sensitized in culture by incubation with anti-TNP IgE (MEB-38) at 1 μg/mL. Sixteen hours after sensitization, the BMMCs were washed with culture media. Cells were then incubated with liposomes displaying TNP antigen alone or liposomes co-displaying TNP-antigen with Siglec-8 ligand (TNP-STAL/Sig8L) at a final lipid concentration at 5 uM. Eight hours later, the supernatant was harvested and the concentration of mouse IL-13 or TNF-alpha was determined using an ELISA kit (Biolegend).

Results

Figure 12C:
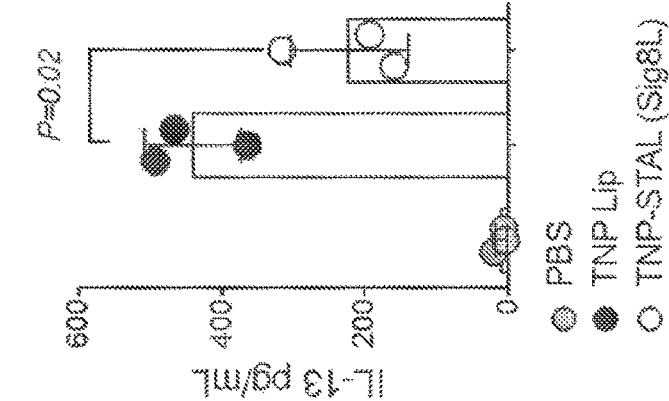
FIGS. 12A-12C illustrate the in vitro degranulation and cytokine inhibitory effects of liposomes displaying the TNP antigen and a Siglec-8 ligand.
Figure 12B:
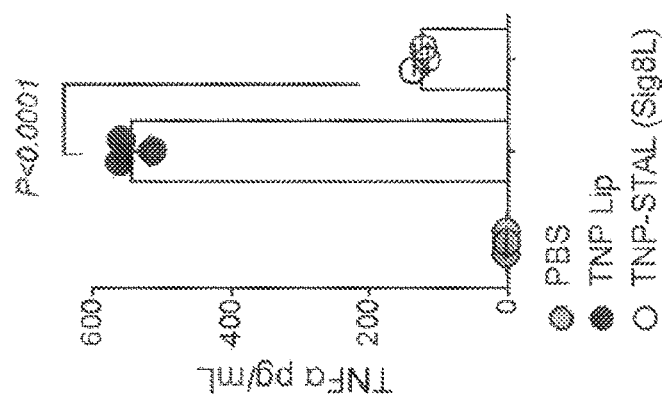
Figure 12A:
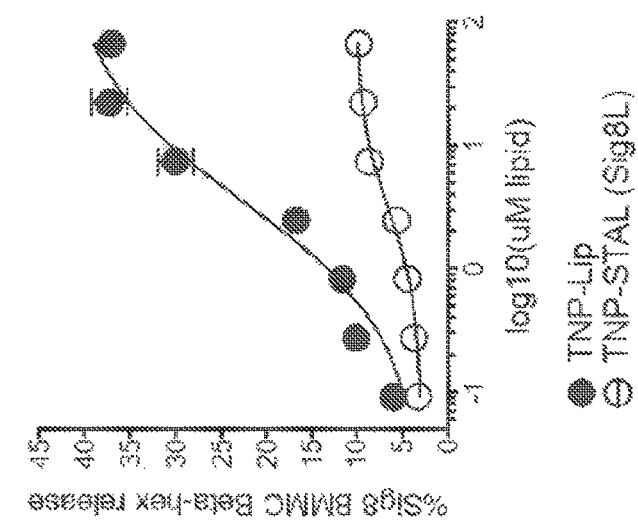

FIG. 12A illustrates that liposomes bearing TNP only (TNP-lip, black circles) strongly induced degranulation of Siglec-8+ bone marrow derived mast cells (BMMCs) as quantified by beta-hexosaminidase release. Liposomes co-displaying TNP and Siglec-8 ligand (TNP-STALs/Sig8L; open circles) do not cause release of beta-hexosaminidase. FIG. 12B and FIG. 12C illustrate that liposomes bearing TNP alone (TNP-lip, black circles) strongly induced production of pro-inflammatory cytokine including TNFα and IL-13. Liposomes co-displaying TNP and Siglec-8 ligand (TNP-STAL/Sig8L; open circles) fail to stimulate production of TNFα and IL-13, compared to liposomes displaying TNP alone that do stimulate robust production of these cytokines.

Example 13: Suppression of TNP-Induced Local Vascular Leakage Using Ligand of Siglec-8 in a Passive Cutaneous Anaphylaxis Model This Example describes experiments demonstrating that when transgenic mice expressing a human Siglec-8 transgene were challenged with the TNP antigen, they develop blue ears due to vascular leakage of pre-administered Evan's blue dye. Such vascular leakage is a hallmark of IgE-mast cell activation. Notably, this local vascular leakages does not occur when liposomes are administered that display both the TNP antigen and Siglec-8 ligands, indicating that the presence of Siglec-8 ligands on the liposomes that also display antigen can inhibit mast cell degranulation.

Methods

Wild type (WT) or Siglec-8 transgenic (Siglec-8 Tg) mice were used in these studies. On day 0, PBS was intradermally administered to one ear of each mouse, as injection control, while the other ear was given 125 ng of murine anti-TNP-IgE. The next day, the nice were intravenously injected with either 150 ug of liposomes displaying TNP-only or with 150 ug liposomes co-displaying TNP and Siglec-8 ligand (TNP-STAL/Sig8L) in 1% Evan's blue dye. Sixty minutes later, after the mice were euthanized, the ears were cut, weight, and diced into small pieces. The ear pieces were incubated in 500 uL of dimethylformamide (DMF) overnight and the Evan's blue released into the ear was quantified at absorbance at 650 mm. Unpaired student t test was used.

Results

FIG. 13B-13C illustrates that in WT mice the ear that was sensitized with anti-TNP IgE turned blue within 60 minutes after administration of TNP-liposomes. The ear that was given mock injection remains grey—the normal skin color (FIG. 13B). WT mice do not express Siglec-8, and therefore INP-STAL(Sig8L) also turned the sensitized ear blue. Accordingly, TNP-liposomes and TNP-STAL(Sig8L) induced equivalent vascular leakage in WT mice as quantified by FIG. 13C.

Figure 13D:
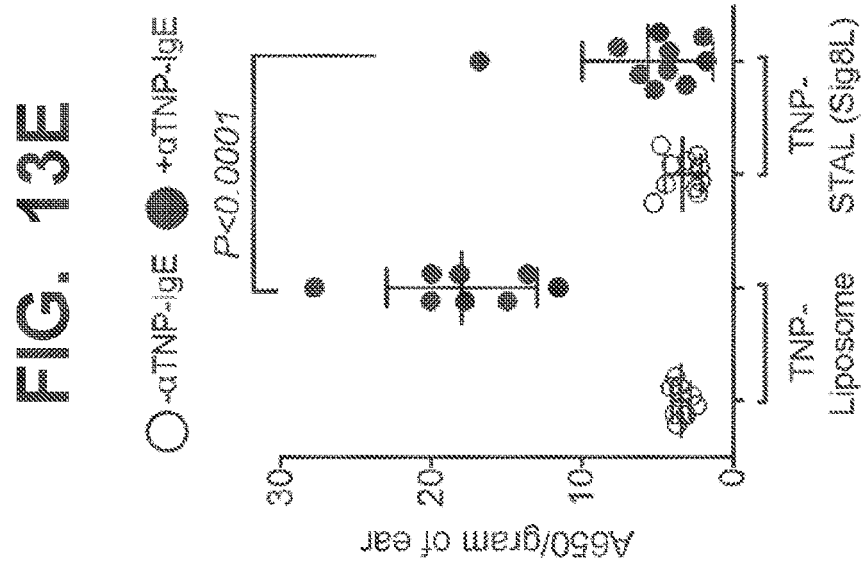
Figure 13E:
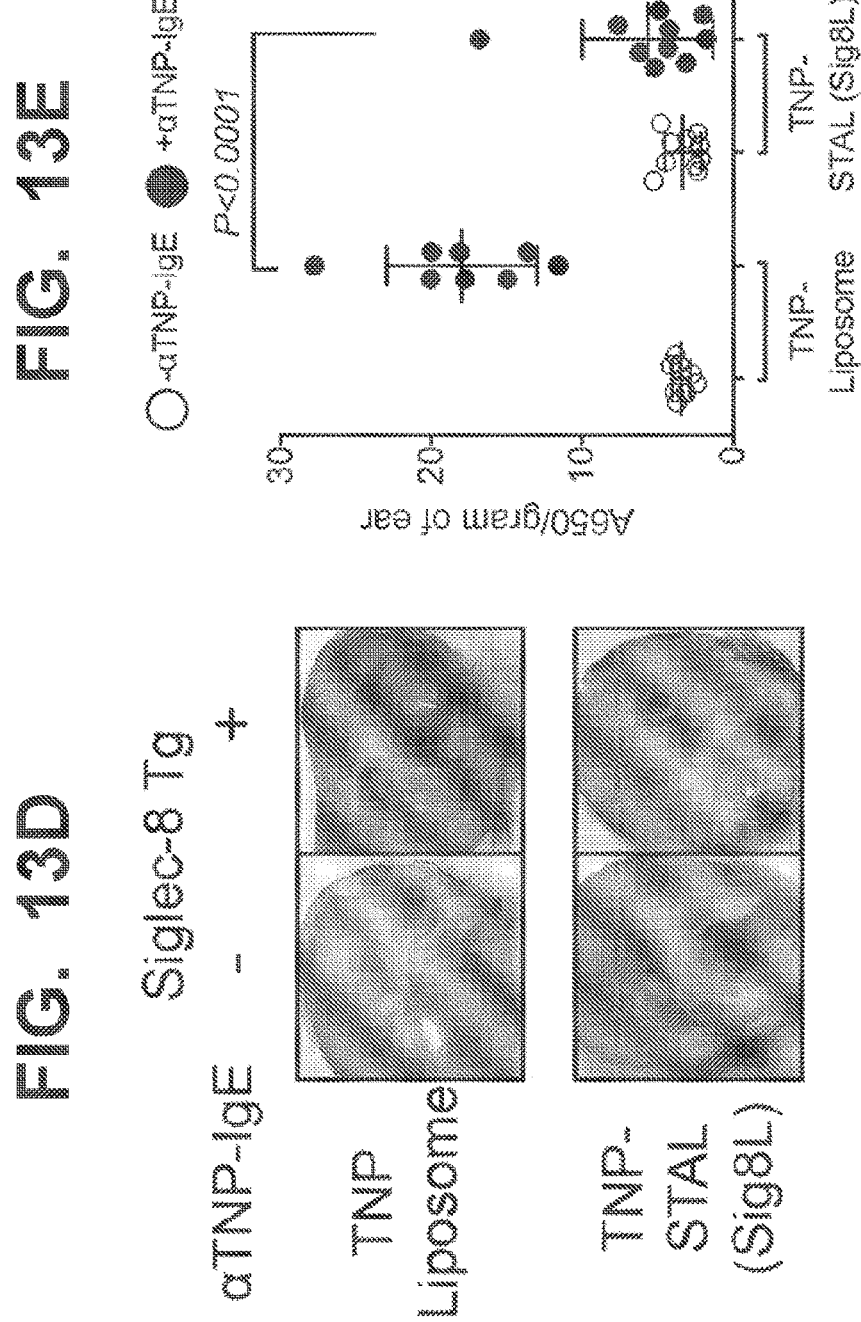

FIG. 13D-13E illustrate that sensitized ears of Siglec-8 expressing mice developed vascular leakage when challenged with liposomes displaying TNP-only (TNP-liposome). By contrast, sensitized ears of Siglec-8 Tg mice do not turn blue when the mice were treated with liposomes co-displaying TNP and Siglec-8 (TNP-STAL/Sig8L) (FIG. 13D). FIG. 13E quantitatively confirms that administration of with liposomes co-displaying TNP and Siglec-8 (TNP-STAL/Sig8L) inhibits vascular leakage.

Example 14: Suppression of TNP-Induced Anaphylaxis in Siglec-8 Transgenic Mice Using Ligands of Siglec-8

This Example illustrates that liposomes co-displaying TNP and human Siglec-8 ligand (TNP-STAL/Sig8L) fail to stimulate TNP-induced systemic anaphylaxis in the Siglec-8 transgenic mice. However, WT mice did undergo TNP-induced systemic anaphylaxis when administered liposomes co-displaying TNP and human Siglec-8 ligand (TNP-STAL/Sig8L). This example also demonstrates that these TNP-STAL (Sig8L) desensitize Siglec-8-Tg mice from a subsequent antigen challenge.

Methods

The passive systemic anaphylaxis model illustrated in FIG. 9A was used to detect anaphylaxis.

WT or Siglec-8-Tg mice were intravenously sensitized with 10 ug of murine anti-TNP-IgE, (Biolegend, Clone MEB-38) on day 0. On day 1, mice were intravenously treated with 150 ug of liposome displaying TNP only (TNP lip) or liposomes co-displaying TNP and Siglec-8 ligand (TNP-STAL/Sig8L). Rectal temperatures were monitored for 1 hour as read out for systemic anaphylaxis.

For desensitization experiment, Siglec-8-Tg were intravenously sensitized with 10 ug of murine anti-TNP-IgE (Biolegend, Clone MEB-38) on day 0. On day 1, mice were intravenously treated with PBS (grey circles) or 225 ug of liposomes co-displaying TNP and human Siglec-8 ligand (TNP-STAL/Sig8L; open circles) at time zero and at 2.5 hour. Rectal temperatures were monitored for 40 minutes. Five hours after the initial treatment, all mice were challenged with 45 ug of liposomes displaying TNP only. Rectal temperatures were monitored for another 1 hour.

Results

Figure 14A:
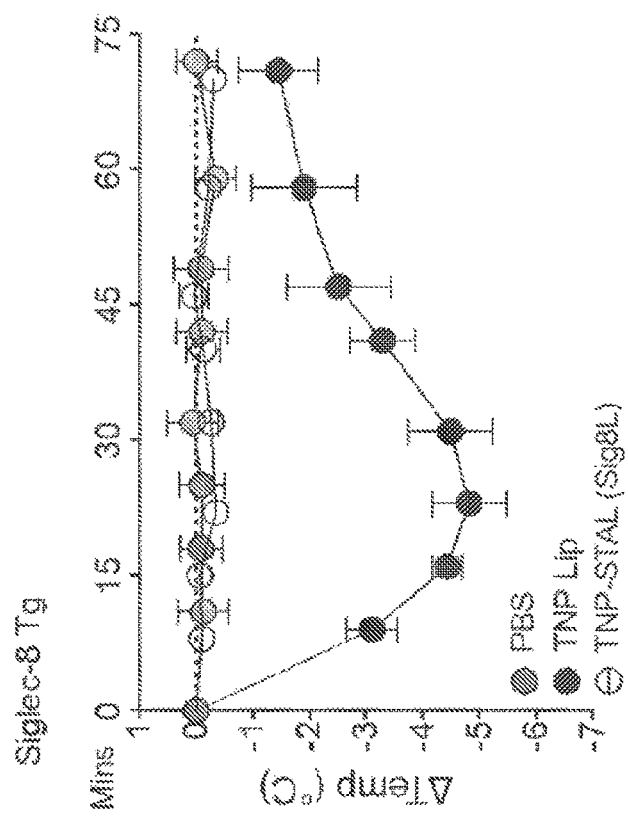
FIG. 14A-14E graphically illustrate that TNP-STAL prevents anaphylaxis from subsequent antigen challenge, as detected by rectal temperature. WT mice were sensitized with anti-TNP-IgE, and challenged with liposomes displaying the TNP antigen only or liposomes co-displaying TNP antigen and Siglec-8 ligand (TNP-STAL/Sig8L).

Anaphylaxis: FIG. 14A illustrates that WT mice treated with liposomes displaying both the TNP-antigen and Siglec-8 ligand (TNP-STAL/Sig8L, open circles) develop anaphylaxis in a manner similar to WT mice treated with liposomes displaying TNP-antigen alone (black circles).

Figure 14B:
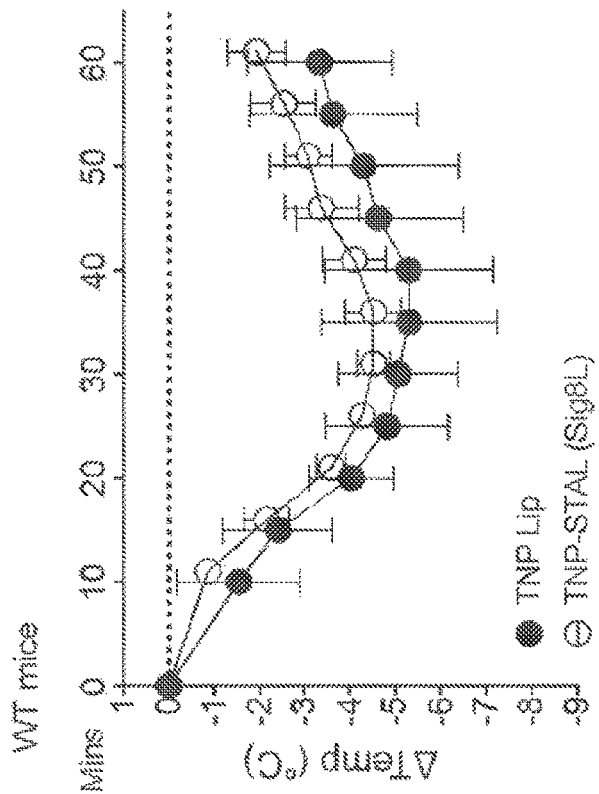

By contrast, in FIG. 14B, while Siglec-8 transgenic mice developed severe anaphylaxis when treated with liposomes displaying TNP alone (black circles), Siglec-8 transgenic mice are protected from anaphylaxis when given liposomes co-displaying TNP antigen and Siglec-8 ligand (TNP-STAL/Sig8L; open circles).

Figure 14C:
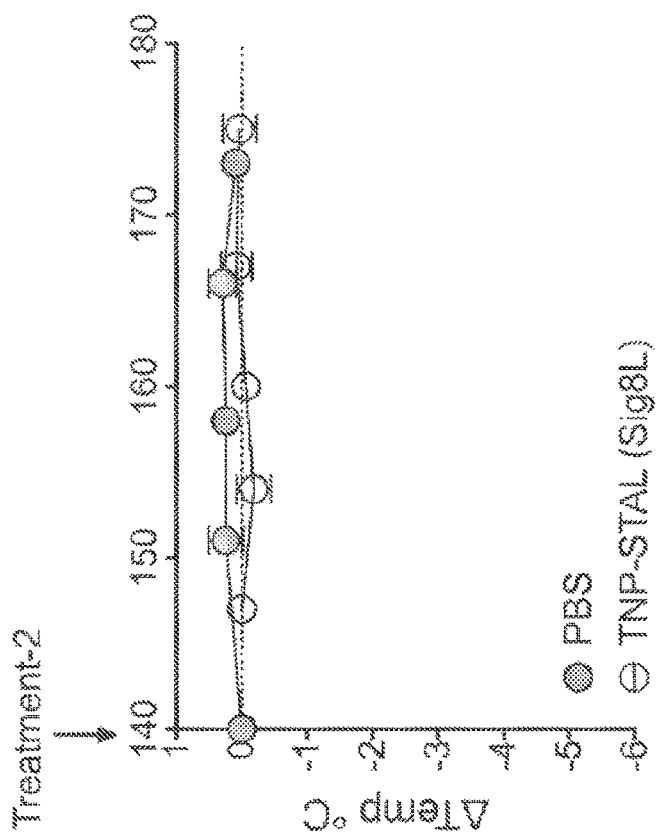
Figure 14D:
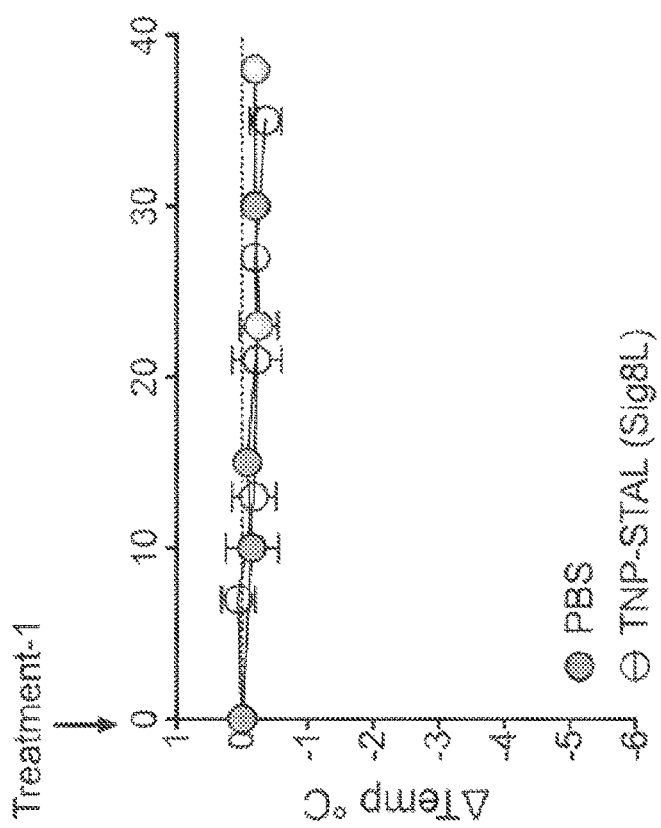
Figure 14E:
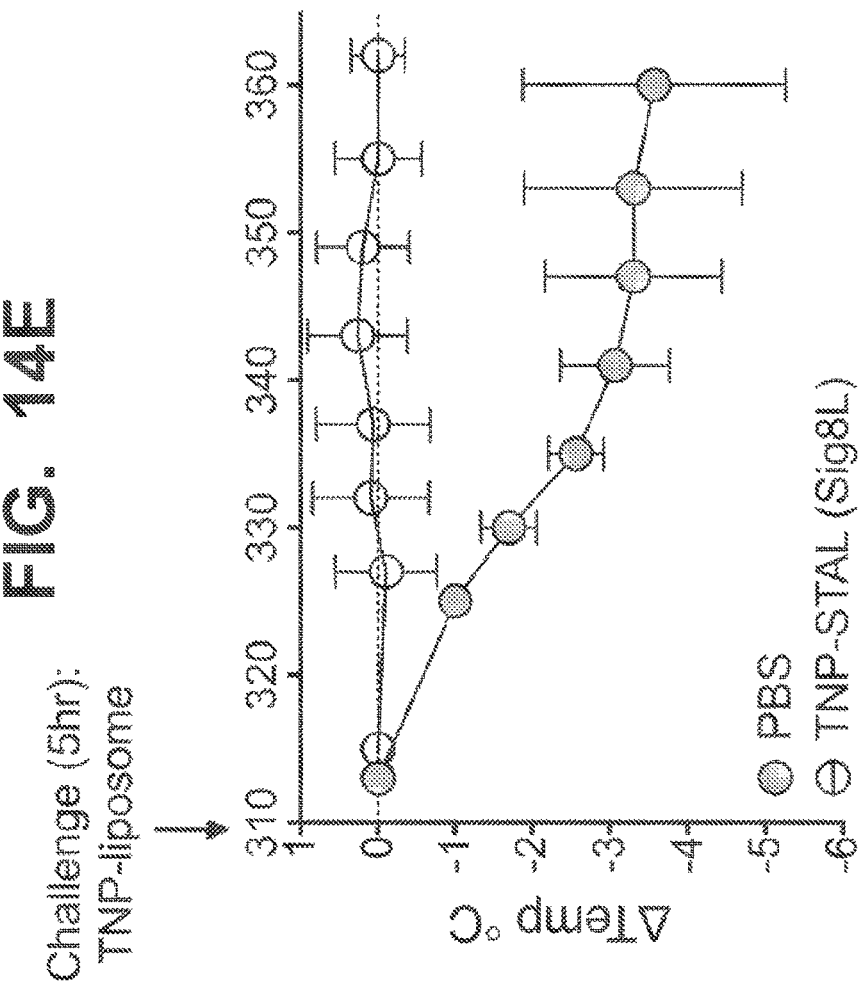

Desensitization. FIG. 14C-14E illustrate results of a desensitization experiment. Siglec-8 mice did not develop anaphylaxis when treated with 225 ug of TNP-STAL(Sig8L) at time 0 (FIG. 14C) and time 2.5 hour (FIG. 141)) compared to PBS control. At 5 hours, when all mice were challenged with 45 ug of TNP-liposomes, mice previously received PBS developed severe anaphylaxis (FIG. 14E).

In contrast, mice received TNP-STAL(Sig8L) are resistant from developing anaphylaxis (FIG. 14E).

Example 15: High Affinity CD33 (Siglec-3) Ligands

This Example describes screens for Siglec ligands with affinity for CD33.

Methods

CD33 siglec ligands referred to as compounds 3-21 were synthesized using the following procedure (Scheme 1).

The conditions and reagents employed for synthesis of compounds 3-21 were:

(i) *N. meningitidis* CMP-NeuAc synthetase (CTP), and *P. damsella* α2-6 sialyltransferase. The yield of compound C was 98%, and the yield of compound D was 90%.

(ii) For X as Cl, the reagents were MeOH, $CH_2Cl_2$, $NEt_3$. For X as N-hydroxysuccinimide the reagents were DMF, $H_2O$, $NaHCO_3$.

(iii) For R as NHCbz the reagents were Pd/C, $H_2$, $H_2O$. The yields were 77-92% over the two steps.

(iv) For R as $N_3$ the reagents were $PMe_3$, THF, $H_2O$. The yields 70-75% over the two steps.

The CD33 siglec ligand referred to as compound 22 was synthesized using the following procedure (Scheme 2).

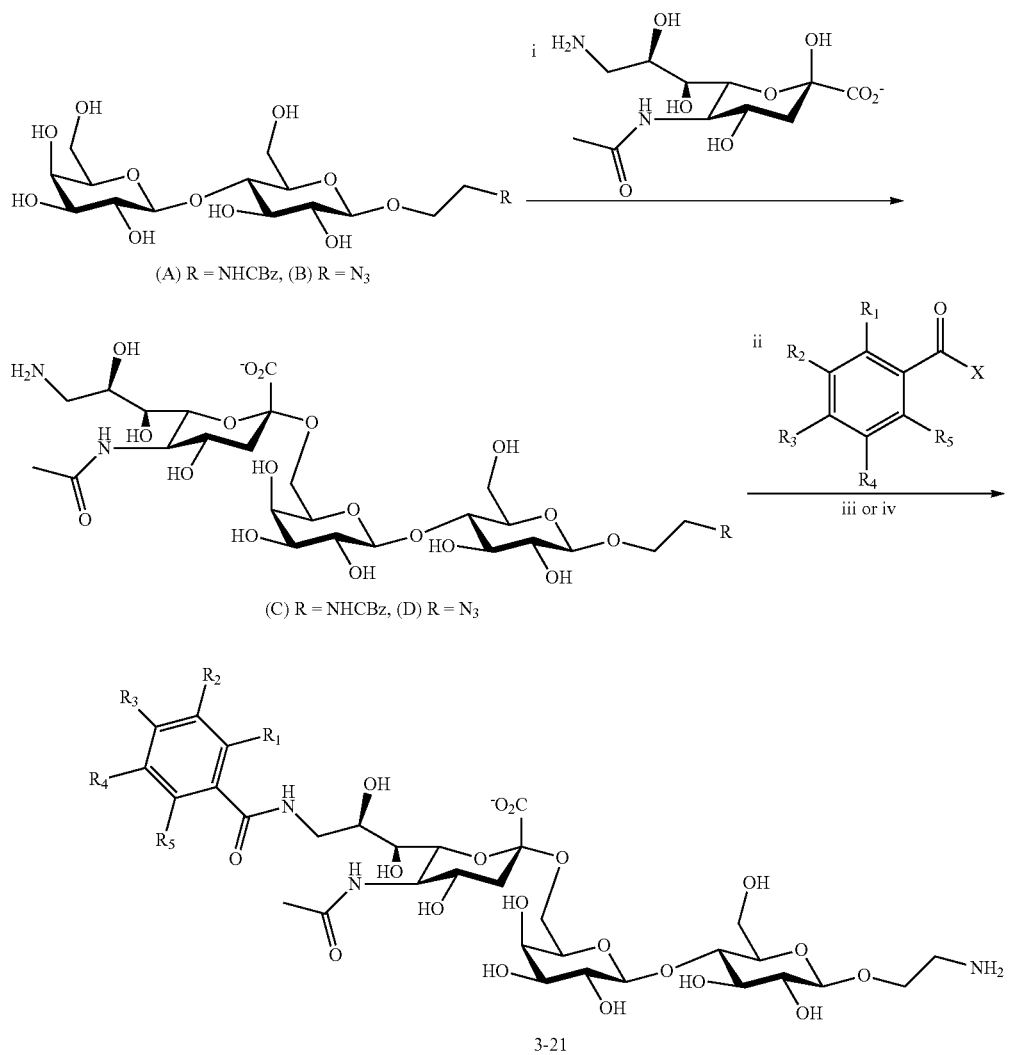

3-21

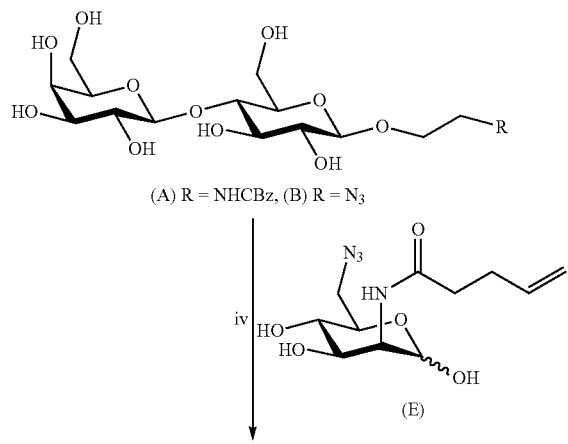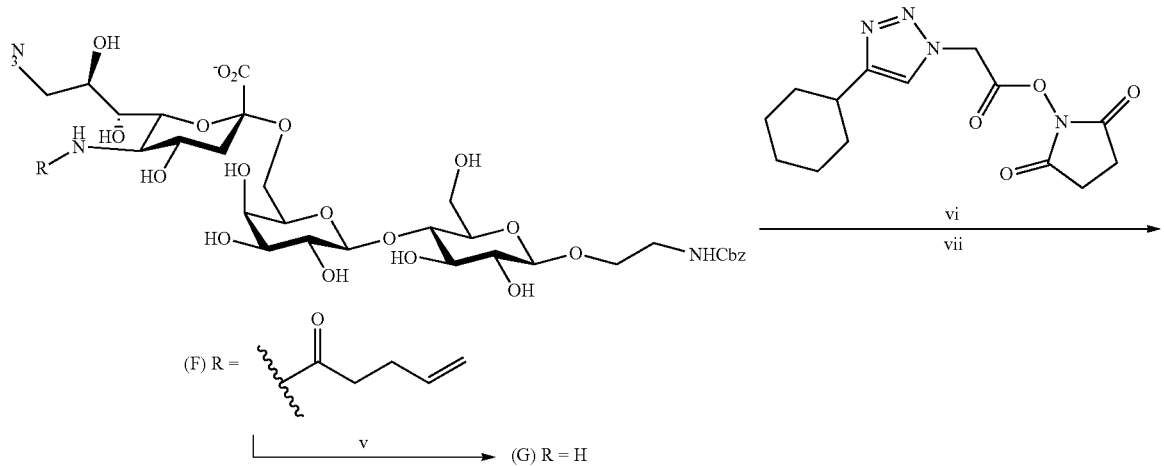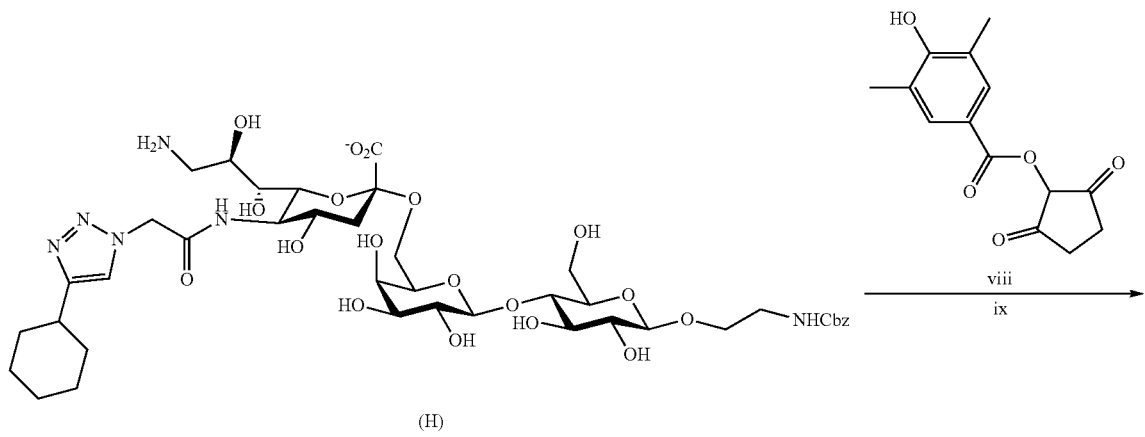

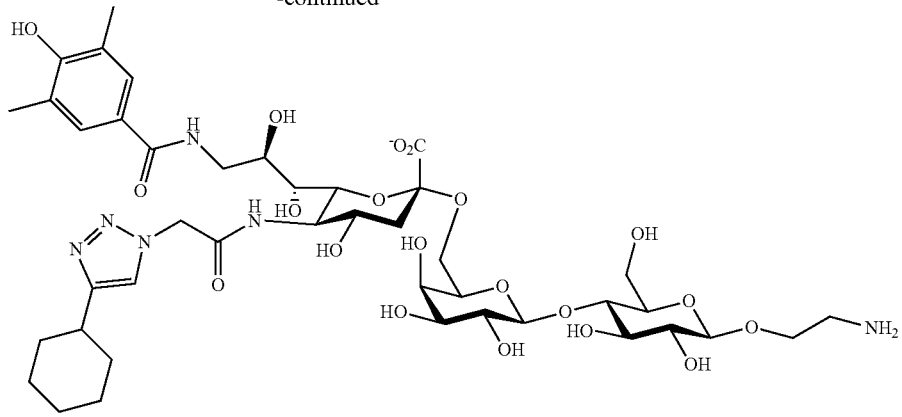

22

For step iv the reagents to synthesize (A) were: pyruvate. C. perfringens NeuAc aldolase (CTP), N. meningitidis CMP-NeuAc synthetase, P. Damsella α2-6 sialyltransferase; and the yield was 96%. For step v the reagents were H$_2$O, MeOH, I$_2$, pH 1.0; and the yield was 75%. For step vi the reagents were DMF, NEt$_3$; and the yield was 86%. For step vii the reagents were PMe$_3$, THF, H$_2$O; and the yield was 97%, For step viii the reagents were DMF, H$_2$O, NaHCO$_3$; and the yield was 73%. For step ix the reagents were Pd/C, H$_2$, H$_2$O; and the yield was 90%.

Compounds were spot-printed in five replicates at 100 μM or 3 μM printing concentration in 150 mM phosphate buffer, 0.005% Tween-20, pH 8.2, using techniques described by Rillahan et al. (Angew. Chem., Int. Ed Engl., 51: 11014-11018 (2012)); Blixt et al. J. Am. Chem. Soc. 130: 6680-6681 (2008)); and Blixt et al. (Proc. Natl. Acad. Sci. U.S.A., 2004, 101: 17033-17038 (2004)). Siglec-Fc chimeras were produced in-house using stable expression in CHO cells (hCD33 and sialoadhesin (Sigler-1, mSn) or transient transfection into COS-cells as described by Blixt et al. (J. Biol. Chem., 278: 31007-31019 (2003)). For binding studies shown in FIG. 15, hCD33-Fc was pre-complexed (10 μg/ml Fe-chimera) with an R-PE labelled anti-human IgG (5 μg/ml, Jackson Immunoresearch) and serially diluted onto the array. Analysis with hCD22-Fc and mSn-Fc was performed similarly.

For the results shown in FIG. 15B-15E, the same procedures were used for hCD33 and mSn; however, a more sensitive approach was used to better distinguish between high affinity hCD22 ligands. In this process, hCD22-Fc was applied to the array at various concentrations, the arrays were washed by dipping three times into a reservoir of PBS-Tween, followed by detection with the above R-PE labelled secondary antibody (10 μg/ml), Final washes in both procedures included dipping three times into reservoirs of PBS-Tween, PBS, and water, followed by centrifugation to dry. Slides were then scanned on a Perkin-Elmer ProScanArray Express and the images processed using IMAGENE. Data shown are the mean±S.D. of the five printed spots.

Results

C9-substituted benzamide sialic acid analogs were screened as potential high-affinity CD33 ligands using iterative rounds of focused library synthesis coupled with glycan array screening to simultaneously address affinity and selectivity for this siglec. It was reasoned that an optimal C9 substituent combined with the 4-cyclohexyl-1,2,3-triazole at the C5 position could work synergistically to achieve high affinity and selectivity for hCD33.

Figure 15A:
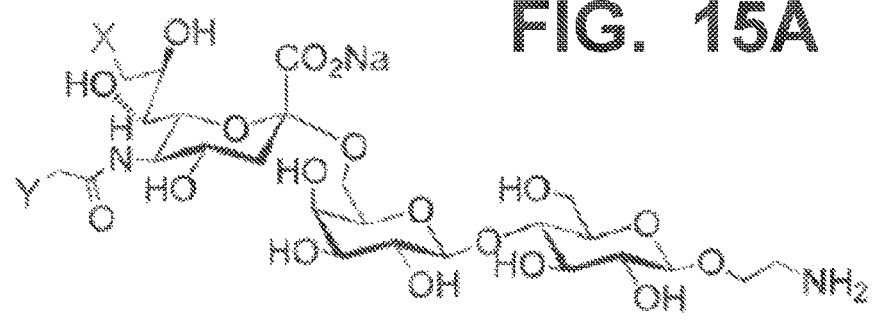
FIG. 15A-15E illustrate structures of Siglec-3 (CD33) ligands and binding of these ligands to Siglec-3, Siglec-2 (CD22), and mouse Siglec-1 (sialoadhesin).
Figure 15B:
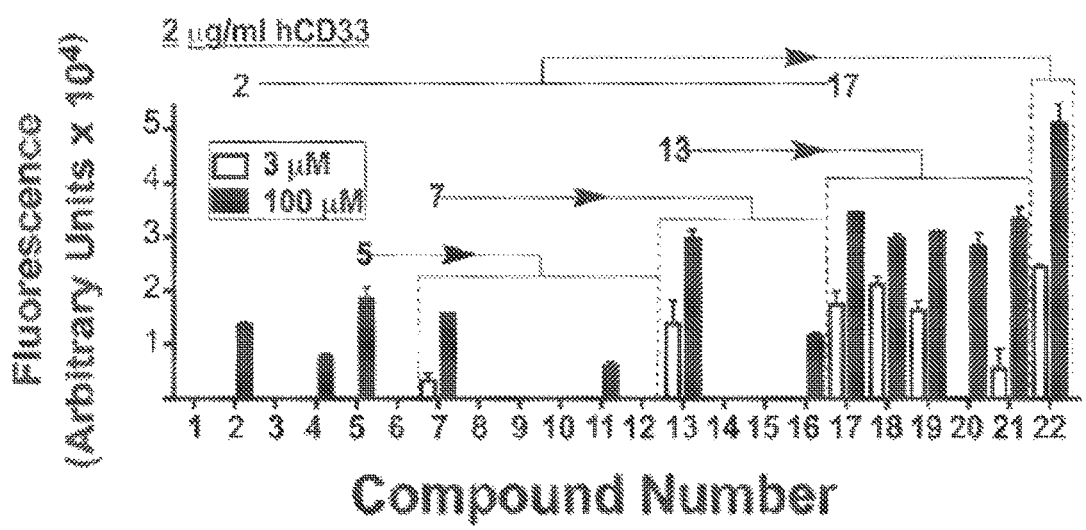

As a first step towards this goal, an initial series of 9-benzamide substituents were synthesized and analyzed by glycan array (FIG. 15A, compounds 3-6). It was noted that replacing the biphenyl substituent used in other Siglec ligands with a single benzamido group (3) completely abolished binding to hCD33 (FIG. 15B). Interestingly, however, addition of an acetylene moiety to the meta-(5) but not para-(6) position of the benzamide ring re-established this affinity gain and improved selectivity. Notably, click chemistry-derived products of compound 5 with a variety of azides completely abolished binding to hCD33 and suggested a potential steric clash of large moieties at this position (data not shown). Other substituents were tested at the meta position of the benzamide ring, particularly small ones, to ascertain whether those substituents could yield further improvements in binding compared to compound 5.

Figure 15C:
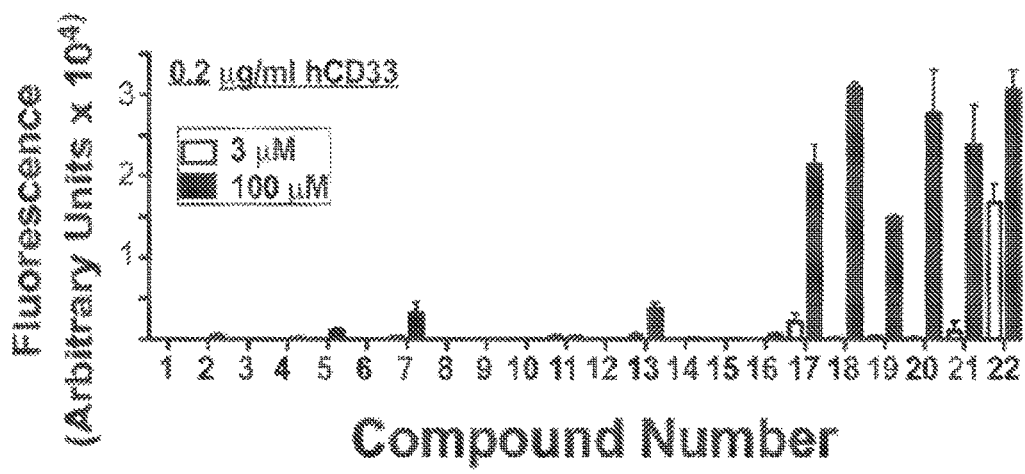
Figure 15D:
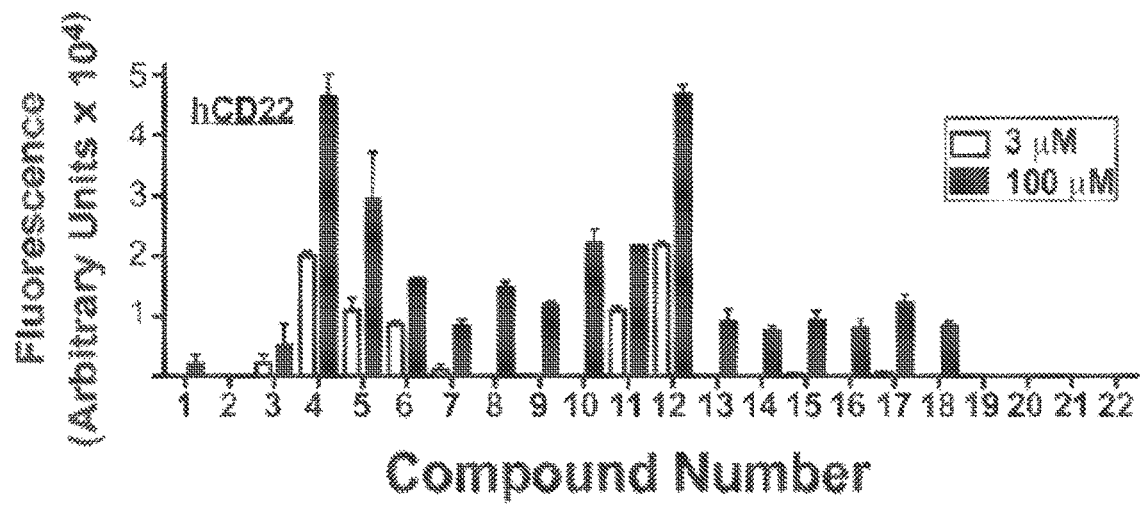
Figure 15E:
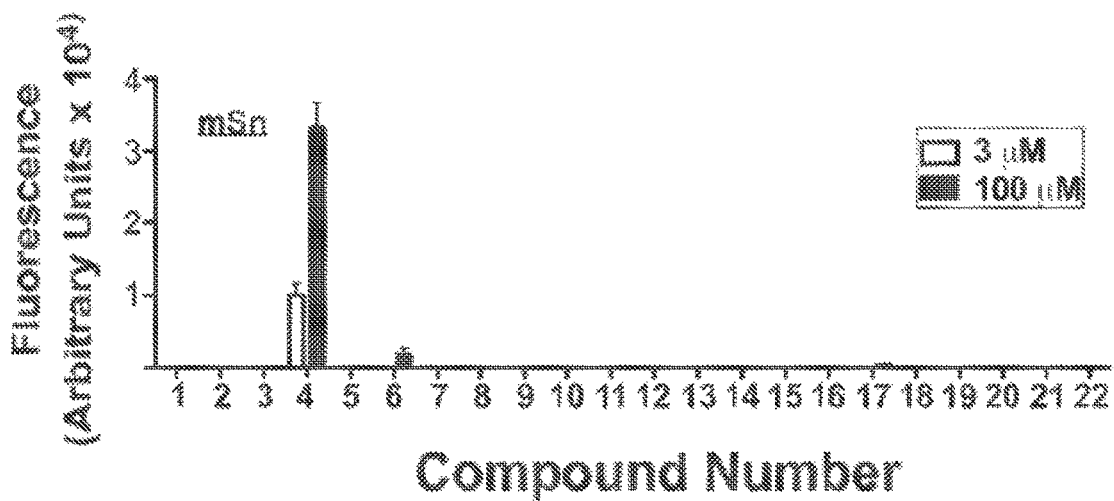

Accordingly, a small library of C9-analogues with meta-substituted benzamide rings was generated in the α2-6 linked scaffold (FIG. 15A, compounds 7-12). This was accomplished through a simple synthetic strategy involving enzymatic transfer of a 9-amino sialic acid to an azide or Cbz-protected lactosyl-b-O-ethylamine scaffold (Scheme 1, compounds A and B), followed by N-acylation of the C9 position of sialic acid, and deprotection of the linker to the free amine required for microcontact printing. The inventors routinely confirmed that all compounds are comparably printed using the α2-6-linkage specific plant lectin SNA, which is not affected by the presence of 9-substituents. On a 5-10 mg scale, this procedure reproducibly offered compounds in excellent yield and purity. Utilizing this approach, analogs with both small (7-11) and large (12) substituents at the meta position of the benzamide ring were created. Upon glycan array analysis, compound 7, with a 3-methylbenzamido substituent, yielded the most promising increase in affinity and selectivity over compound 5 (FIG. 15B-15C).

With a goal to improve upon compound 7, another library containing C9-appended, 3-methylbenzamide substituents, was designed with additional perturbations to the benzamide ring (FIG. 15A, compounds 13-16). From this library, compound 13, containing a 3,5-dimethylbenzamide substituent, gave a further improvement in affinity and selectivity for hCD33 (FIG. 15B-15C), while the 2,3-dimethyl isomer 14 abolished binding. Since the methyl group of the 3-methylbenzamide appeared to influence binding to hCD33 (compare 3 and 7), the further increase in avidity for the 3,5-dimethylsubstituent may be an entropic effect due to the symmetry of the resulting ring.

It was notable that all substitutions at the 2- and 5-position of the benzamide ring abrogated binding to hCD33 (see results for compounds 14 and 15, FIG. 15A-15C), while modifications at the 4-positon were sometimes tolerated (see results for compounds 4 and 16, FIG. 15A-15C), To extend these observations, the inventors constructed a panel of C9-substituted 3,5-dimethylbenzamide analogs with various alterations at the 4-position (FIG. 15A, compounds 17-21). While all of these analogues improved affinity and retained or improved selectivity, compound 17 appeared to be the most promising ligand generated as shown by the fact that it is the only compound of this series detected at a printing concentration of 3 μM and a low hCD33 concentration (0.2 mg/ml, FIG. 15B, lower panel). This conclusion was further supported by experiments where fluorescently labelled CHO cells expressing high levels of hCD33 cells (CHO-hCD33) were overlaid onto the array. In this case only compounds 17 and 18 of this series could support binding of these cells, confirming that they exhibited highest avidity for CD33.

Having optimized substituents at the 3, 4, and 5 positions on the C9-benzamide ring the inventors then analyzed whether addition of the previously identified C5 substituent, 4-cyclohexyl-1,2,3-triazole (compound 2), would provide further avidity.

To accomplish the synthesis of a 9,5-disubstituted sialoside the inventors employed a strategy involving chemo-enzymatic synthesis of a sialoside orthogonally protected at the two positions (Scheme 2), in addition to the aglycone. For this strategy a three enzyme one-pot reaction was employed that converts a 6-azido-N-pentenoyl-mannosamine (F in Scheme 2) into a 9-azido-5-N-pentenoyl sialic acid by condensation with pyruvate, which is then activated to the corresponding CMP-sialic acid followed by sialyltransferase-mediated α2-6 sialylation of the lactoside (compound A in Scheme 2) to yield the trisaccharide precursor (compound F in Scheme 2). Subsequent deprotection of the pentenoyl group afforded (see compound G) to which the 4-cyclohexyl-1,2,3-triazole was installed using NHS chemistry. Reduction of the azide group at C9, followed by amine acylation, and hydrogenation of the Cbz group on the aglycone generated compound 22 in good overall yield. This approach represents a flexible strategy to synthesize 9,5-disubstitued sialosides, as exemplified by the synthesis of compound 22 described herein.

Microarray analysis showed that compound 22 exhibited superior properties compared to the monosubstituted compounds, for hCD33. In particular, compound 22 exhibited higher avidity than both parent compounds, 17 and 2 (FIG. 15B, lower panel), and showed increased selectivity for hCD33 over hCD22 and mSn (FIG. 15C). This increase in avidity was further supported by the fact that HL-60 cells, an AML cell line expressing intermediate levels of hCD33, bound to compound 22.

Glycan microarrays may provide only qualitative measures of avidity and selectivity. Therefore, the relative affinities of these compounds were analyzed using solution-phase inhibition assays where $IC_{50}$ values were determined using a flow cytometry assay. The flow cytometry assay evaluated whether the compounds were able to prevent the binding of fluorescently labelled hCD33 to ligand-coated beads, and these values were used to determine the relative inhibitory potency (rIP) for each compound compared to the native sialoside (rIP=1).

The results of these assays were in remarkable agreement with the qualitative estimation of avidity gains obtained from the microarray studies. Table 3 shows the $IC_{50}$ and rIP values for selected compounds.

TABLE 3

| Compound | $IC_{50}$ value (μM) | rIP value |
|---|---|---|
| | $IC_{50}$ and rIP values | |
| 1 | 3780 ± 811 | 1 |
| 2 | 977 ± 289 | 3.9 |
| 7 | 174 ± 52 | 22 |
| 13 | 82 ± 18 | 46 |
| 17 | 33 ± 10 | 113 |
| 22 | 11 ± 3 | 351 |

The native sialoside (compound 1) showed a relatively low affinity for hCD33 (IC50=3.78 mM).47 Relative to the native sialoside, the optimal 5-substituted analogue (compound 2) gave only a 4-fold increase in affinity (IC50=997 mM, rIP=3.9), and the 9-substituted, 3-methylbenzamide analogue (compound 7) yielded a 20-fold increase (IC50=174 mM, rIP=22). Each additional perturbation to the benzamide ring (compounds 13 and 17) added affinity gains of 2-3 fold.

By combining C5 and C9 substituents a roughly additive increase in affinity was obtained, as exemplified by compound 22, which had an $IC_{50}$ of 11 μM. These results highlight the utility of microarrays for rapid qualitative analysis of avidity gains, which led to the identification of compound 22 having a 350-fold increased affinity over the natural sialoside.

Example 16: Screen for High Affinity Siglec-8 Ligands

Using methods similar to those described in the foregoing Examples, a series of 69 different compounds were screened for binding to Siglec-8. Several ligands were identified as having good affinity for Siglec-8.

Methods

Sixty-nine C-9 sulfonamides were synthesized using the method illustrated below.

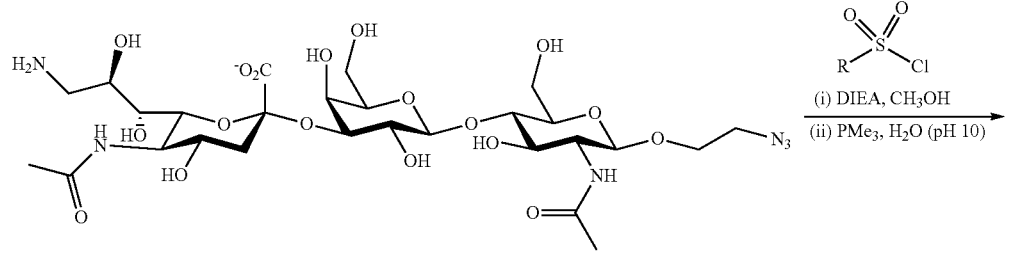

-continued

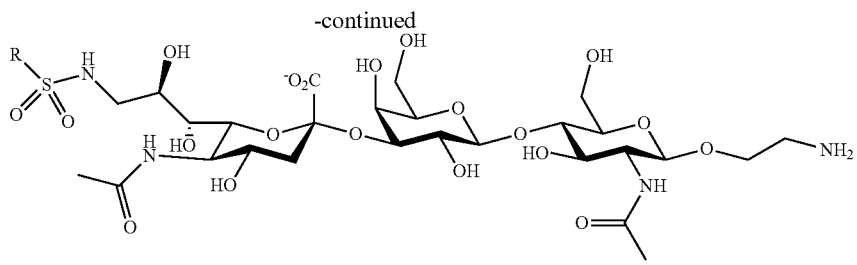

1-69

The sixty-nine C-9 sulfonamides were synthesized in parallel by reacting 9-NH$_2$ Neu5Acα2-3LacNAc-ethylazide with a panel of sixty-nine sulfonyl chlorides in methanol with diisopropylethylamine. The sixty-nine C-9 sulfonamide Neu5Acα2-3LacNAc-ethylazide analogs were then reacted with trimethyl phosphine (2 eq) to reduce the ethyl azide linker to an ethyl amine. Stock solutions for each member of the analog library were prepared by dilution in H$_2$O (1 mM sialoside concentration).

Compounds were spot-printed in four replicates at 100, 20, 4, 0.8, 0.16 printing concentration in 300 mM phosphate buffer, 0.005% Tween-20, pH 8.2, using techniques described by Rillahan et al. (*Angew. Chem., Int. Ed. Engl.*, 51: 11014-11018 (2012)); Blixt et al. (*J. Am. Chem. Soc.* 130: 6680-6681 (2008)); and Blixt et al. (*Proc. Natl. Acad. Sci. U.S.A.*, 2004, 101: 17033-17038 (2004)). Siglec-Fc chimeras were produced in-house using stable expression in CHO cells (Siglec-8 Fc).

Figure 16A:
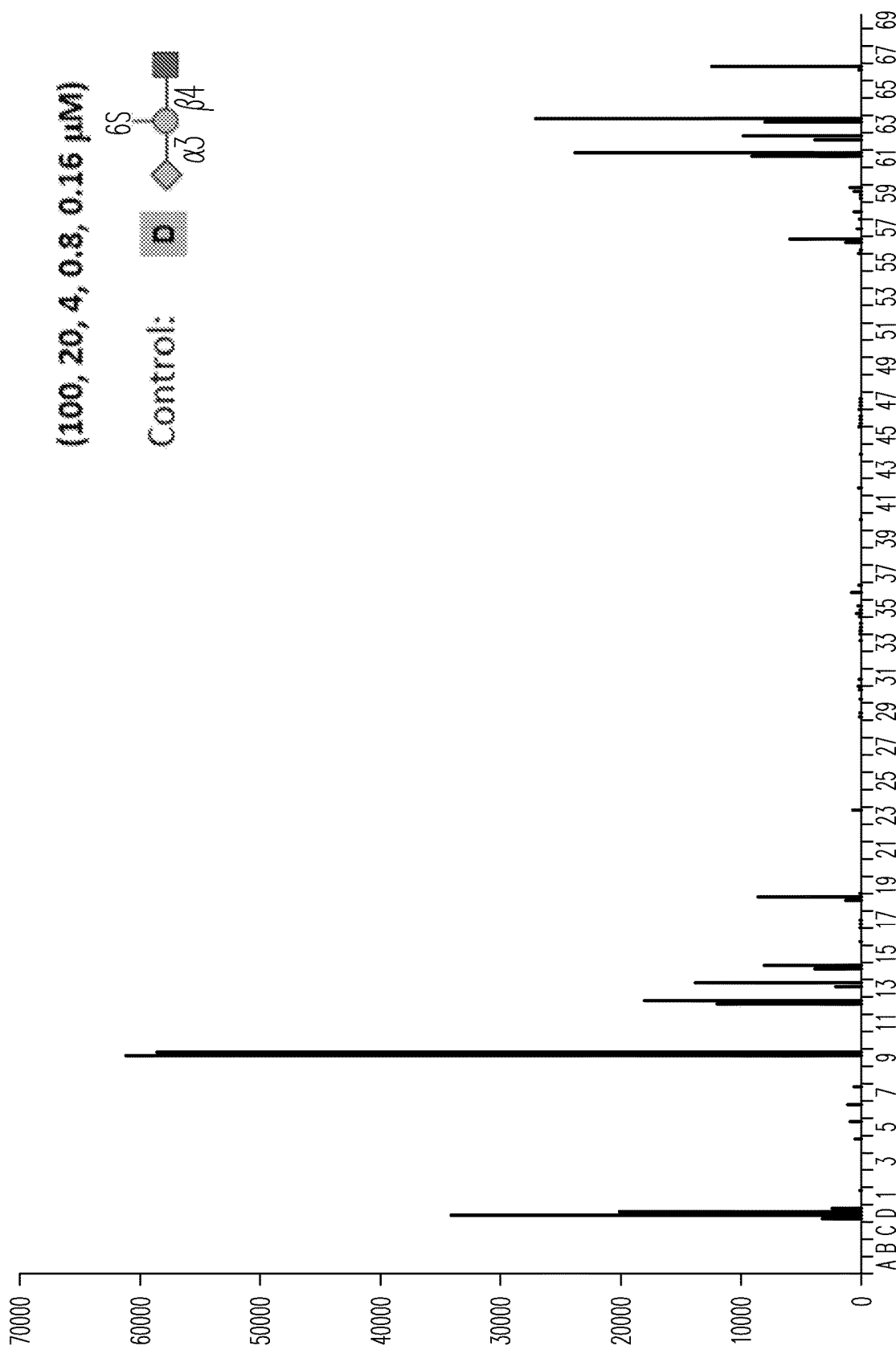
FIG. 16A-16B illustrate some structures of Siglec-8 ligands and their binding affinities for Siglec-8.

For binding studies shown in FIG. 16A, Siglec-8-Fc was pre-complexed (10 ug/ml Fc-chimera) with an R-PE labelled anti-human IgG (5 μg/ml, Jackson Immunoresearch) and serially diluted onto the array. Following incubation, the glass slide was washed by dipping three times into reservoirs of PBS-Tween, PBS, and water, followed by centrifugation to dry. Slides were then scanned on a Perkin-Elmer ProScanArray Express and the images processed using IMAGENE. Data shown are the mean±S.D. of the four printed spots.

Results

Figure 16B:
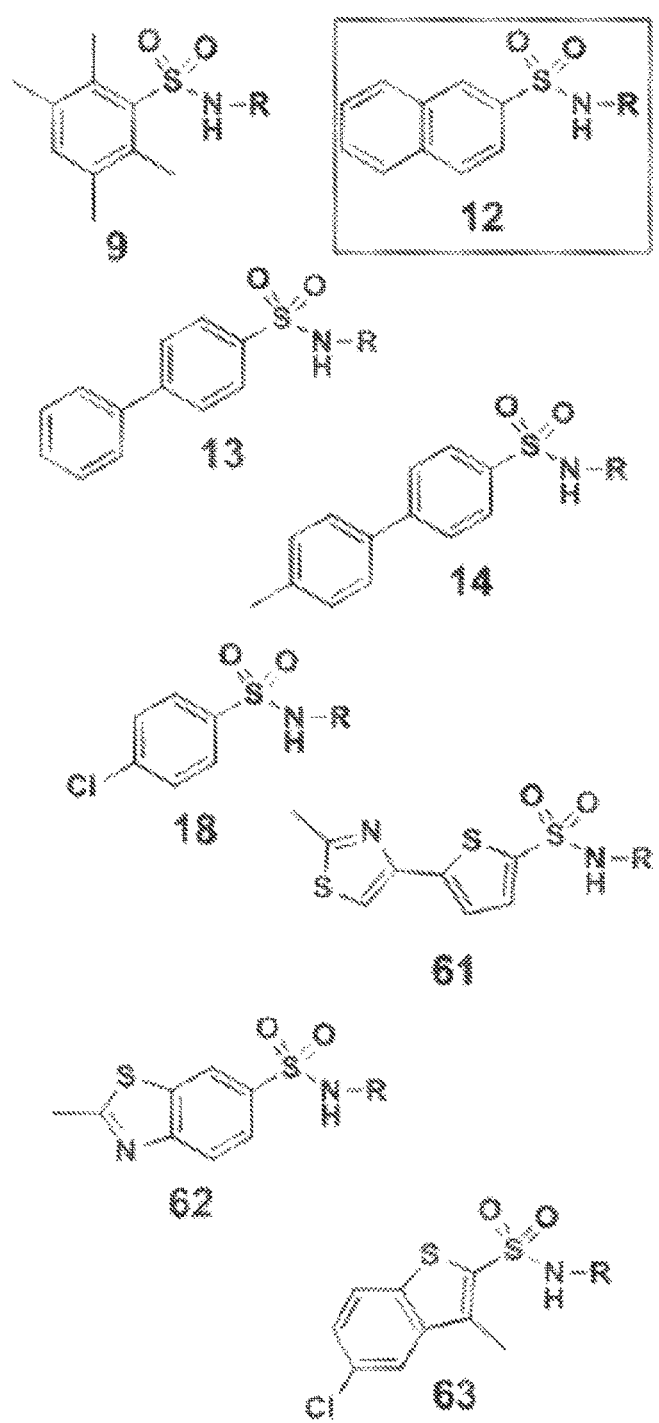

FIG. 16A graphically illustrates binding affinities of potential Siglec-8 ligands 1-69 in an assay containing Siglec-8 (10 μg/ml) pre-complexed with anti-human IG-RPE (5 μg/ml). The binding of controls A-D is also shown. As illustrated, Siglec-8 ligands 9, 12, 13, 14, 18, 61, 62, and 63 bound Siglec-8 with affinity. FIG. 16B shows structures of Siglec-8 ligands 9, 12, 13, 14, 18, 61, 62, and 63, where R was R=C9-Neu5Acα2-3LacNAc-ethylamine.

Example 17: Suppression of TNP-Induced Degranulation with Ligand of hCD22

This Example illustrates that liposomes co-displaying TNP and human CD22 ligand do not stimulate TNP-induced degranulation using human mast cell line LAD2.

Methods

Human mast cell line (LAD2 cells) were pre-sensitized with IgE reactive to hapten TNP. Cells are then incubated with liposomes that displaying only TNP or with liposomes displaying both TNP and human CD22 ligand (F-MPB). Degranulation of LAD2 cells are quantified by measuring beta-hexosaminidase released.

Results

Figure 17:
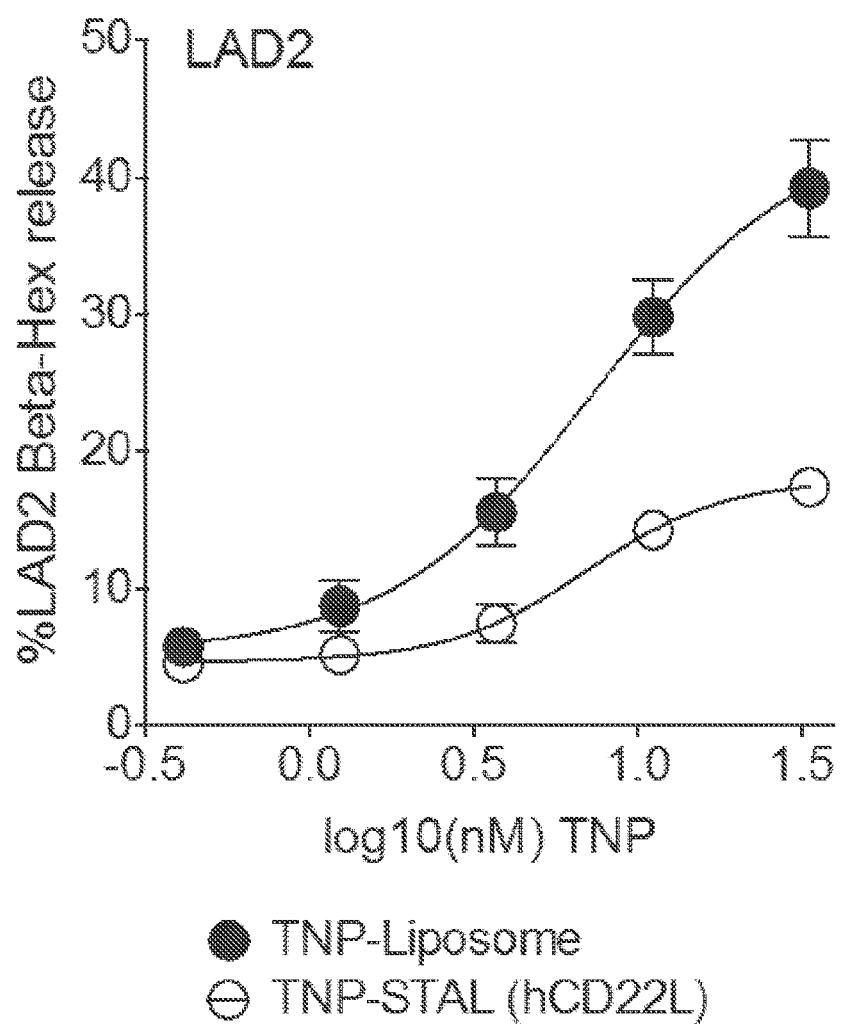
FIG. 17 illustrates that liposomes co-displaying hCD22L with trinitrophenol (TNP) antigen (INP-STAL/hCD22L, open symbols) significantly reduce degranulation of LAD2 cell sensitized with anti-TNP-IgE when compared to liposomes displaying TNP antigen alone (TNP-liposomes, black symbols) as measured in percent beta-hexosaminidase release.)

As illustrated in FIG. 17, liposomes displaying TNP-alone (Black symbol) induces beta-hexosaminidase release of LAD2 cells. Liposomes co-displaying TNP and hCD22 ligand (TNP-STAL/hCD22L, open symbol) induces significantly less beta-hexosaminidase comparing to black symbols.

REFERENCES

1. Macauley, M. S.; Crocker, P. R.; Paulson, J. C., *Nat Rev Immunol* 2014, 14 (10), 653-66.
2. Crocker, P. R.; Paulson, J. C.; Varki, A., *Nat Rev Immunol* 2007, 7 (4), 255-66.
3. Rillahan, C. D.; Schwartz, E.; Rademacher, C.; McBride, R.; Rangarajan, J.; Fokin, V. V.; Paulson, J. C., *ACS Chem Biol* 2013, 8 (7), 1417-22.
4. Rillahan, C. D.; Schwartz, E.; McBride, R., Fokin, V. V.; Paulson, J. C., *Angew Chem Int Ed Engl* 2012, 51 (44), 11014-8.
5. Rillahan, C. D.; Macauley, M. S.; Schwartz, E.; He, Y.; McBride, R.; Arlian, B. M.; Rangarajan, J.; Fokin, V. V.; Paulson, J. C., *Chem Sci* 2014, 5 (6), 2398-2406.
6. Nycholat, C. M.; Rademacher, C.; Kawasaki, N.; Paulson, J. C., *J Am Chem Soc* 2012, 134 (38), 1.5696-9.
7. Bull, C.; Heise, T.; Adema, G. J.; Boltje, T. J., *Trends Biochem Sci* 2016, 41 (6), 519-31.
8. Bull, C.; Heise, T.; van Hitters, N.; Pijnenborg, J. F.; Bloemendal, V. R.; Gerrits, L.; Kers-Rebel, E. D.; Ritschel, T.; den Brok, M. H.; Adema, G. J.; Boltje, T. J., *Angew Chem Int Ed Engl.* 2017, 56 (12), 3309-3313.
9. Yu, W.; Freeland, D. M.; Nadeau, K. C., *Nat Rev Immunol* 2016, 16 (12), 751-765.
10. Sicherer, S. H.; Sampson, H. A., *J Allergy Clin Immunol* 201.4, 133 (2), 291-307; quiz 308.

All patents and publications referenced or mentioned herein are indicative of the levels of skill of those skilled in the all to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A composition comprising an antigen and Siglec ligand that binds to Sialic acid-binding Ig-like lectin-3 (Siglec-3) or Siglec-8.

The composition of statement 1, where the Siglec ligand comprises a compound of Formula I.

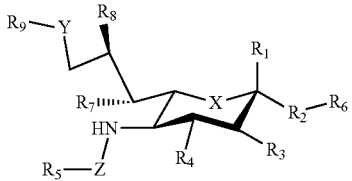

I where:
- X can be a methylene ($CH_2$) or a heteroatom;
- $R_1$ can be hydrogen, carboxylase, aldehyde (CHO), phosphate or sulfate;
- $R_2$ can be a hydrogen, a bond, a heteroatom, an alkyl, a hydroxy, a heterocycle, a second sugar, or a carrier;
- $R_3$, $R_4$, $R_7$ and $R_8$ can each independently be hydrogen, amino, or hydroxyl;
- $R_5$ can be a hydrogen, alkyl, aryl, alkylaryl, heteroaryl, or alkylheteroaryl, wherein the alkyl, aryl, alkylaryl, heteroaryl, or alkylheteroaryl can be substituted with one or more substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteraarylalkyl, amidoheteroaryl, alkoxyamidoheteroaryl, or alkylhalide group;
- $R_6$ can be a hydrogen, a heteroatom, a hydroxy, an alkyl, an alkylamine, an aryl, a heteroaryl, a second sugar, or a carrier;
- Y can be a heteroatom, carboxyl, carboxylate, methylene, amide, —$CH_2$-amide, sulfonyl, —$CH_2$-sulfonyl, sulfonamide, —$CH_2$-sulfonamide, urea, $CH_2$-urea, thiourea, or —$CH_2$-thiourea;
- Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, —$CH_2$-thiourea;
- $R_9$ can be hydrogen, hydroxyl, alkyl, alkoxy, alkylamino, amide, carbonyl, sulfonyl, urea, thiourea, aryl, arylalkoxy, alkoxyaryl, heteroaryl, or heterocycle,
  where the $R_9$ alkyl, alkoxy, alkylamino, aryl, arylalkoxy, alkoxyaryl, heteroaryl, or heterocycle group can be substituted with one or more selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group.

2. The composition of statement 1 or 2, where the Siglec ligand comprises a compound of Formula I as a first sugar, a second and/or a third sugar moiety.

3. The composition of statements 1, 2 or 3, where the Siglec ligand comprises a compound comprising a first sugar and a second sugar, where the first sugar is a compound of Formula I and the second sugar is a compound of Formula II:

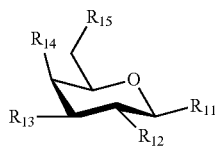

II where:
- $R_{11}$ is a heteroatom, hydroxy, a covalent bond, third sugar, or carrier;
- $R_{12}$ is a hydrogen, or a hydroxyl;
- $R_{13}$ is a hydrogen, a hydroxyl, a heteroatom, or the first sugar;
- $R_{14}$ is a hydrogen, or a hydroxyl; and
- $R_{15}$ is a hydrogen, a hydroxyl, a heteroatom, a sulfate, or the first sugar.

4. The composition of statement 1-3 or 4, where the Siglec ligand comprises a compound comprising a first sugar and a third sugar, where the first sugar is a compound of Formula I and the third sugar is a compound of Formula III:

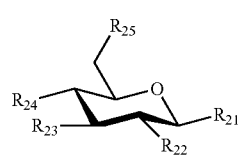

III where:
- $R_{21}$ is a heteroatom, an alkoxy, ether, alkylamine, O-linked alkylamine, carrier, crosslinker, pegylated-lipid, lipid, or polyacrylamide, where the heteroatom, alkoxy, ether, alkylamine, or O-linked alkylamine can be linked to, or substituted with, a crosslinker, or a carrier;
- $R_{22}$ is hydrogen, heteroatom, hydroxyl, N-acetylamine, amide, sulfonamide, urea, or thiourea, where the heteroatom, hydroxyl, N-acetylamine, amide, sulfonamide, urea, or thiourea can be substituted with an alkyl, aryl or heteroaryl; and where the alkyl, aryl, or heteroaryl can be substituted with one to five hydroxy, amino, azido, cyano, nitro, halo, alkyl, $CF_3$, alkoxy, carboxylate, ether, lower alkenyl, lower alkynyl, phenyl, heteroaryl or alkylhalide group;
- $R_{23}$ is a hydrogen, a hydroxyl, an acetylamine, or a fucose moiety;
- $R_{24}$ is a heteroatom, a covalent bond, or the second sugar; and
- $R_{25}$ is a hydrogen, hydroxyl, sulfate, carboxy late, or phosphate.

5. The composition of statement 1-4 or 5, where the Siglec ligands comprise a first sugar comprising a compound of Formula I, where the $R_2$ or the $R_6$ group is a second sugar.

6. The composition of statement 1-5 or 6, where the Siglec ligands comprise a first sugar comprising a compound of Formula 1, where the $R_2$ or the $R_6$ group is a second sugar, and the first and second sugar are linked by a 2-3 or 2-6 glycosidic linkage.

7. The composition of statement 1-6 or 7, where the Siglec ligands comprise a first sugar comprising a compound of Formula 1, a second sugar comprising a compound of Formula II, and a third sugar comprising a compound of Formula III.

8. The composition of statement 1-7 or 8, where the Siglec ligands comprise a first sugar comprising a compound of Formula I, a second sugar comprising a compound of Formula II, and a third sugar comprising a compound of Formula III, and where the second and third sugars are linked by a 1-4 linkage.

9. The composition of statement 1-8 or 9, where the Siglec ligands comprise Siglec-3 ligands comprising Formula I:

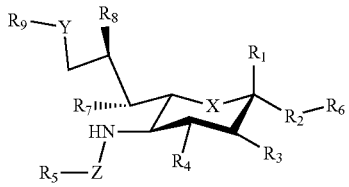

where:
- X can be an oxygen heteroatom;
- $R_1$ can be a carboxy late;
- $R_2$ can be a hydrogen, a bond, a heteroatom, a hydroxy, a second sugar, or a carrier;
- $R_3$ can be a hydrogen, or a hydroxyl;
- $R_4$ can be a hydroxyl;
- $R_5$ can be a lower alkyl, or heteroaryl such as the following:

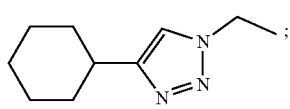

- $R_6$ can be a hydrogen, a heteroatom, a hydroxy, an alkyl, an alkylamine, a second sugar, or a carrier;
- $R_8$ can be a hydroxyl;
- Y can be —$CH_2$-amide;
- Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, or —$CH_2$-thiourea; and
- $R_9$ can be aryl, heteroaryl, or heterocycle, where the aryl, heteroaryl, or heterocycle can be substituted with one to five hydroxy, amino, cyano, nitro, halo, alkyl, $CF_3$, alkoxy, carboxylate, ether, lower alkenyl, lower alkynyl, phenyl, or alkylhalide groups.

10. The composition of statement 1-9 or 10, where the Siglec ligands comprise Siglec-3 ligands where the $R_9$ group is a phenyl with a lower alkyl group at one or both mesa position.

11. The composition of statement 1-10 or 11, where the Siglec ligands comprise Siglec-3 ligands where the $R_9$ group is a phenyl with a hydroxy, amino, alkoxy, nitro, or halide group at the phenyl para position.

12. The composition of statement 4-11 or 12, where the $R_{15}$ is a first sugar (a substituted derivative of N-acetyl-neuraminic acid sialic acid).

13. The composition of statement 1-12 or 13, where the Siglec ligands comprise Siglec-3 ligands comprise one or more of the following:

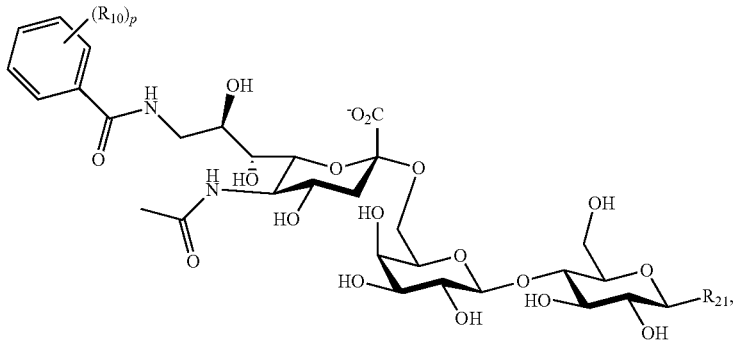

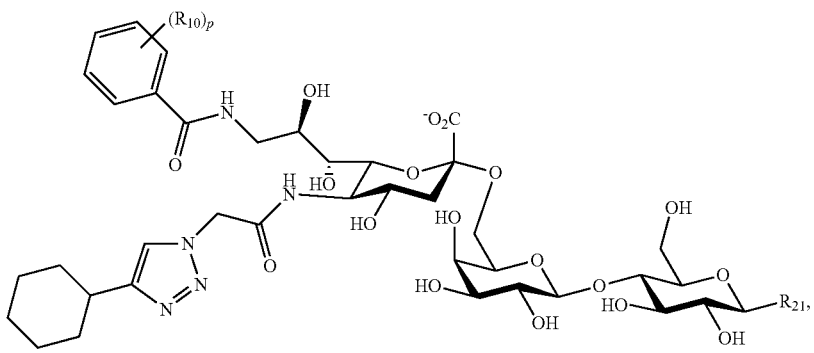

or a combination thereof;
where:
R$_{21}$ is a heteroatom, an alkoxy, an ether, an alkylamine, a carrier, a crosslinker, or an O-linked alkylamine, where the heteroatom, alkoxy, ether, alkylamine, or O-linked alkylamine can be linked to, or substituted with, a crosslinker, or a carrier;
p is an integer of from 0-5; and
each R$_{10}$ is separately selected from hydroxy, amino, cyano, nitro, halo, alkyl, CF$_3$, alkoxy, carboxylate, ether, lower alkenyl, lower alkynyl, phenyl, or alkylhalide.

14. The composition of statement 1-13 or 14, where the Siglec ligands comprise Siglec-8 ligands comprising Formula I:

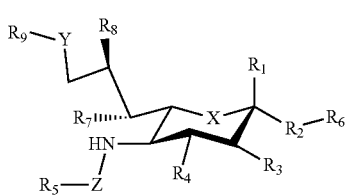

where:
X can be an oxygen heteroatom;
R$_1$ can be a carboxy late;
R$_2$ can be a hydrogen, a bond, a heteroatom, an alkyl, a hydroxy, a second sugar, or a carrier;
R$_3$ can be a hydrogen;
R$_4$ can a hydroxyl;
R$_5$ can be alkyl, aryl, alkylaryl, heteroaryl, or alkylheteroaryl, wherein the alkyl, aryl, alkylaryl, heteroaryl, or alkylheteroaryl can be substituted with one to two substituents selected from alkyl, phenyl, or cycloalkyl group(s);
R$_6$, can be a hydrogen, heteroatom, hydroxy, alkyl, alkylamine, a second sugar, or a carrier;
R$_7$ and R$_8$ can each independently be a hydrogen, or a hydroxyl;
Y can be sulfonamide, —CH$_2$-sulfonamide, amide, urea, or thiourea;
Z can be a carbonyl, carboxylate, methylene, acyl, aryl, heteroaryl, sulfonyl, —CH$_2$-sulfonyl, sulfonamide, —CH$_2$-sulfonamide, urea, —CH$_2$-urea, thiourea, —CH$_2$-thiourea; and
R$_9$ can be aryl, heteroaryl, or heterocycle, where the aryl, heteroaryl, or heterocycle group can be substituted with one to five hydroxy, amino, cyano, nitro, halo, alkyl, CF$_3$, alkoxy, carboxylate, ether, lower alkenyl, lower alkynyl, phenyl, or alkylhalide groups.

15. The composition of statement 1-14 or 15, where the Siglec ligands comprise Siglec-8 ligands with a second sugar.

16. The composition of statement 1-15 or 16, where the Siglec ligands comprise Siglec-8 ligands with a second sugar linked to the 2 position the first sugar.

17. The composition of statement 1-16 or 17, where the Siglec ligands comprise Siglec-8 ligands with R$_{15}$ as sulfate on a second sugar.

18. The composition of statement 1-17 or 18, where the Siglec ligands comprise Siglec-8 ligands with a second sugar, where R$_{13}$ as the first sugar.

19. The composition of statement 1-18 or 19, where the Siglec ligands comprise Siglec-8 ligands comprising any of the following:

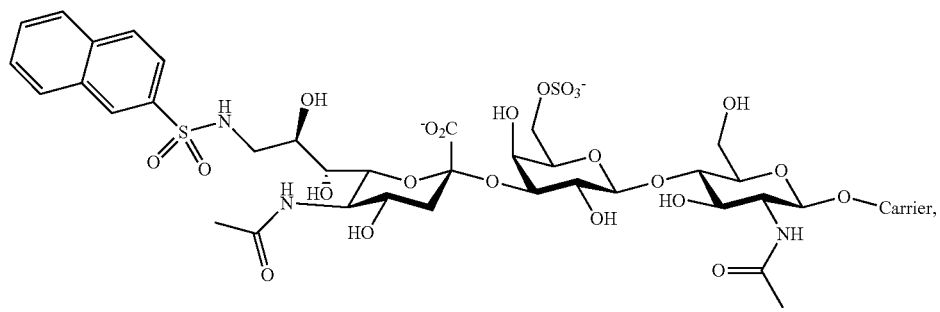

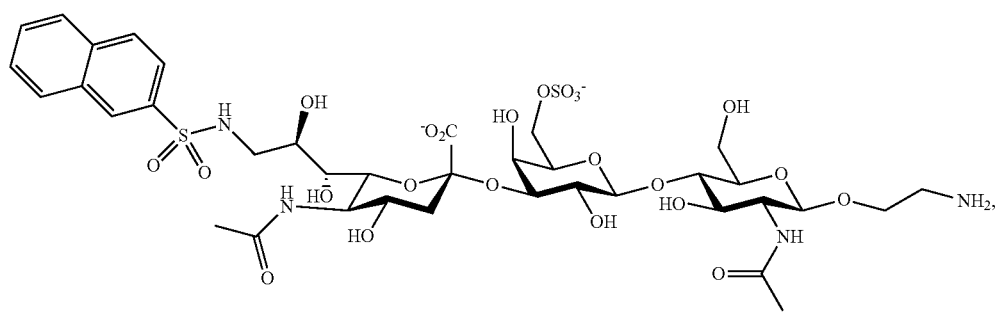

-continued

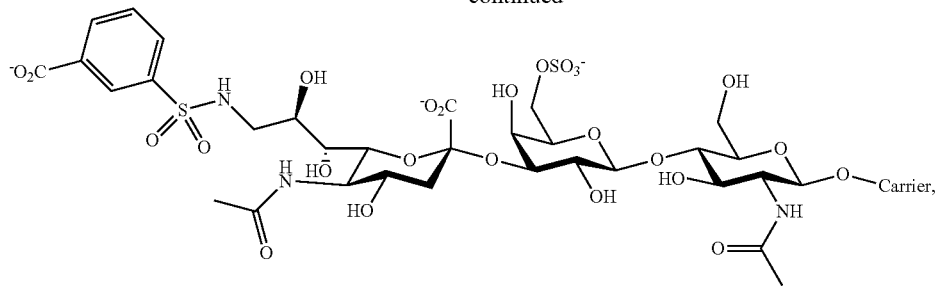

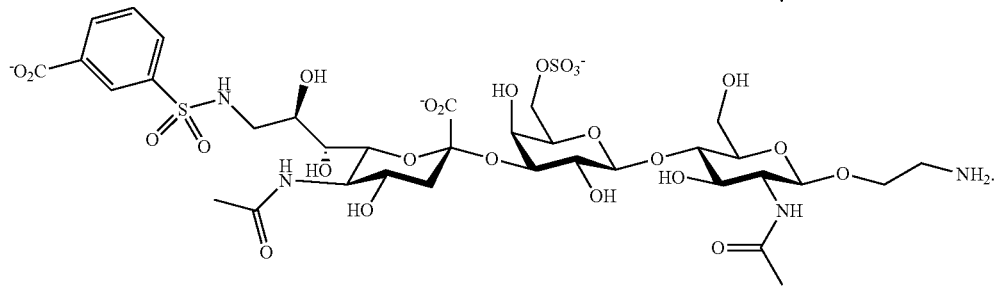

or a combination thereof.

20. The composition of statement 1-19 or 20, where Siglec-8 ligands do not have a sulfate on the optional second sugar.

21. The composition of statement 1-20 or 21, where the antigen is a hapten, antibiotic, food allergen, environmental allergen, antibody (including a therapeutic antibody), therapeutic, and combinations thereof.

22. The composition of statement 1-21 or 22, further comprising an antibody or antibody fragment that binds to an FcεRI-IgE complex.

23. The composition of statement 1-22 or 23, where the antigen is a hapten such as 2,4,6-trinitrophenol; an antibiotic such as a β-lactam antibiotic (including penicillins and cephalosporin), a monobactam (e.g., aztreonam), a carbapenem (e.g., imipenem, meropenem), a clavam (e.g., clavulanic acid), a carbacephem (e.g., loracarbef), a sulfonamide (e.g. sulfamethoxazole, sulfamerazine, sulfamethazine), an antibacterial trimethoprim; a neuromuscular blocking drug such as promethazine, neostigmine, or morphine; a food allergen such as egg (ovalbumin), cow (e.g, Bos d 11, Bos d 4, Bos d5, Bos d 6, Bos d 8, etc), peanut (e.g., Ara h 2, Ara h 1, Ara h 3, Ara h 6, etc), hazelnut (e.g., Cor a 9, Car a 11, Cor a 14, etc), walnut, casein, soy (e.g., GLy m 5, Gly m 6, etc), malt, or shellfish; an environmental allergen such as mouse (e.g., Mus m 1), rat (e.g., Rat n 1), cat (e.g., Fel d 1), dog (e.g., Can f 1), bee, wasp, house dust mite (e.g., Der p 1), short ragweed pollen (e.g., Amb a 1). Birch pollen (e.g. Bet v 1), aspergillus (e.g., Asp r 1), cockroach (e.g., Bla g 2), a tree (e.g., pine pollen, Latex, rubber, *Hevea brasiliensis*); a therapeutic agent (e.g., factor VIII, interferon, erythropoietin); an antibody (e.g., anti-human IgE, anti-human IgE receptor, human IgE, infliximab, adalimumab, trastuzumab, bevacizumab, rituximab, cetuximab, and fragments thereof), and combinations thereof.

24. The composition of statement 1-23 or 24, further comprising one or more carriers.

25. The composition of statement 1-24 or 25, further comprising one or more carriers with components that are covalently bonded to the Siglec ligand, the antigen, or a combination thereof.

26. The composition of statement 1-25 or 26, further comprising one or more carriers with components that are non-covalently associated with the Siglec ligand, the antigen, or a combination thereof.

27. The composition of statement 1-26 or 27, further comprising one or more carriers selected from microparticles, nanoparticles, picoparticles, or a combination thereof.

28. The composition of statements 1-27 or 28, further comprising carriers selected from particles, nanoparticles, liposomes, heads, proteins, polysaccharides, lipids, and combinations thereof.

29. The composition of statement 1-28 or 29, further comprising one or more carriers selected from lipid-based components, protein-based components, nucleic acid based components, carbohydrate-based components, or a combination thereof.

30. The composition of statement 1-29 or 30, further comprising one or more carriers with polymeric components.

31. The composition of statement 1-30 or 31, further comprising one or more carriers with non-polymer components.

32. The composition of statement 1-31 or 32, further comprising a liposomal carrier.

33. The composition of statement 1-32 or 33, further comprising a pharmaceutically acceptable carrier.

34. A method comprising administering the composition of statement 1-33 or 34 to a subject.

35. The method of statement 35, wherein the subject is an animal.

36. The method of statement 35 or 36, wherein the subject is a human, a domesticated animal, a zoo animal, or an experimental animal.

37. The method of statement 35, 36, or 37, where the antigen is a hapten, antibiotic, food allergen, environmental allergen, antibody (including a therapeutic antibody), therapeutic, and combinations thereof.

38. The method of statement 35-37 or 38, where the antigen is a hapten such as 2,4,6-trinitrophenol; an antibiotic such as a lactam antibiotic (including penicillins and cephalosporin), a monobactam (e.g., aztreonam), a carbapenem (e.g., imipenem, meropenem), a clavam (e.g., clavulanic acid), a carbacephem (e.g., loracarbel), a sulfonamide (e.g., sulfamethoxazole, sulfamerazine, sulfamethazine), an antibacterial trimethoprim; a neuromuscular blocking drug such as promethazine, neostigmine, or morphine; a food allergen such as egg (ovalbumin), cow (e.g., Bos d 11, Bos d 4, Bos d5. Bos d 6, Bos d 8, etc), peanut (e.g., Ara h 2, Ara h 1, Ara h 3, Ara h 6, etc), hazelnut (e.g., Cor a 9, Car a 11, Cor a 14, etc), walnut, casein, soy (e.g., GLy in 5, Gly m 6, etc), malt, or shellfish; an environmental allergen such as mouse Mus in 1), rat (e.g., Rat n 1), cat (e.g., Fel d 1), dog (e.g., Can f 1), bee, wasp, house dust mite (e.g., Der p 1), short ragweed pollen (e.g., Amb a 1), Birch pollen (e.g. Bet v 1), aspergillus (e.g., Asp r 1), cockroach (e.g., Bla g 2), a tree (e.g., pine pollen, Latex, rubber, *Hevea brasiliensis*); a therapeutic agent (e.g., factor VIII, interferon, erythropoietin); an antibody (e.g., anti-human IgE, anti-human IgE receptor, human IgE, infliximab, adalimuniab, trastuzumab, hevacizumab, rituximab, cetuximab, and fragments thereof), and combinations thereof.
39. The method of statement 35-38 or 39, wherein the subject suffers from an IgE-mediated disorder or disease.
40. The method of statement 35-39 or 40, wherein the subject suffers from an IgE-mediated disorder or disease selected from allergy, allergic rhinitis, allergic asthma, non-allergic asthma, anaphylaxis, atopic dermatitis, allergic gastroenteropathy, anaphylaxis, urticaria, food allergies, allergic bronchopulmonary aspergillosis, parasitic diseases, interstitial hyper-IgE syndrome, ataxia-telangiectasia, Wiskott-Aldrich syndrome, athymic lymphoplasia, IgE myeloma, graft-versus-host reaction, and allergic purpura.
41. The method of statement 35-40 or 41, which reduces mast cell degranulation by at least 10%, or at least 20%, or at least 25%, or at least 30%, or at least 35%, or at least 40%, or at least 45%, or at least 50%, or at least 55%, or at least 60%, or at least 65%, or at least 70%, or at least 80%, or by at least 90%, or by at least 95%,
42. The method of statement 35-41 or 42, which reduces basophil activation by at least 10%, or at least 20%, or at least 25%, or at least 30%, or at least 35%, or at least 40%, or at least 45%, or at least 50%, or at least 55%, or at least 60%, or at least 65%, or at least 70%, or at least 80%, or by at least 90%, or by at least 95%.
43. The method of statement 35-42 or 43, which reduces anaphylaxis in the subject by at least 25%, or at least 30%, or at least 35%, or at least 40%, or at least 45%, or at least 50%, or at least 55%, or at least 60%, or at least 65%, or at least 70%, or at least 80%, or by at least 90%, or by at least 95%, or by at least 98%.
44. The method of statement 35-43 or 44, which desensitizes the subject to the antigen.
45. The method of statement 35-44 or 45, which desensitizes the subject to subsequent exposure to the antigen.
46. The method of statement 35-45 or 46, which reduces anaphylaxis in the subject by at least 25%, or at least 30%, or at least 35%, or at least 40%, or at least 45%, or at least 50%, or at least 55%, or at least 60%, or at least 65%, or at least 70%, or at least 80%, or by at least 90%, or by at least 95%, or by at least 98% after subsequent encounter with the antigen.
47. A kit comprising at least one container comprising a composition comprising carrier that displays at least one Siglec ligand that binds to an inhibitory Siglec and at least one antigen, and instructions for administering the composition to a subject, using the composition, or testing the composition.
48. The kit of statement 47, further comprising a container comprising an antibody or fragment thereof that binds to a FcεRI-IgE complex.
49. The kit of statement 47 or 48, wherein the antigen is a hapten, an antibiotic, an antibacterial agent, a neuromuscular blocking drug, a food allergen, an environmental allergen, a therapeutic agent, an antibody, or a combination thereof.
50. The kit of statement 47, 48, or 49 further comprising a container comprising an antigen and instructions for administering the antigen after the composition is administered.
51. The kit of statement 50, wherein the antigen is an antibiotic, an antibacterial agent, a neuromuscular blocking drug, a food allergen, a therapeutic agent, an antibody, or a combination thereof.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a promoter" includes a plurality of such nucleic acids or promoters (for example, a solution of nucleic acids or a series of promoters), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method comprising administering to a subject suspected of having an IgE-mediated disorder or disease a composition comprising a carrier that displays (1) at least one antigen and (2) at least one mast cell inhibitory Siglec ligand that binds to an inhibitory Sialic acid-binding Ig-like lectin (Siglec) on a mast cell to inhibit degranulation of the mast cell and thereby treat an IgE-mediated disorder or disease in the subject, where the Siglec ligand comprises a compound of Formula I:

I where:
X can be a methylene ($CH_2$) or a heteroatom;
$R_1$ can be hydrogen, carboxylate, aldehyde (CHO), phosphate or sulfate;
$R_2$ can be a hydrogen, a bond, a heteroatom, an alkyl, a hydroxy, a heterocycle, a second sugar, or a carrier;
$R_3$, $R_4$, $R_7$ and $R_8$ can each independently be hydrogen, amino, or hydroxyl;
$R_5$ can be a hydrogen, alkyl, aryl, alkylaryl, heteroaryl, or alkylheteroaryl, wherein the alkyl, aryl; alkylaryl, heteroaryl, or alkylheteroaryl can be substituted with one or more substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group;
$R_6$ can be a hydrogen, a heteroatom, a hydroxy, an alkyl, an alkylamine, an aryl, a heteroaryl, a second sugar, or a carrier;
Y can be a heteroatom, carboxyl, carboxylate, methylene, amide, —$CH_2$-amide, sulfonyl, —$CH_2$-sulfonyl, sulfonamide, —$CH_2$-sulfonamide, urea, $CH_2$-urea, thiourea, or —$CH_2$-thiourea;
Z can be a carbonyl, carboxylate, methylene, acyl, aryl, heteroaryl, sulfonyl, —$CH_2$-sulfonyl, sulfonamide, —$CH_2$-sulfonamide, urea, —$CH_2$-urea, thiourea, —$CH_2$-thiourea;
$R_9$ can be a hydrogen, hydroxyl, alkyl, alkoxy, alkylamino, amide, carbonyl, sulfonyl, urea, thiourea, aryl, arylalkoxy, alkoxyaryl, heteroaryl, or heterocycle,
where the $R_9$ alkyl, alkoxy, alkylamino, aryl, arylalkoxy, alkoxyaryl, heteroaryl, or heterocycle group can be substituted with one or more substituents selected from hydroxy, amino, azido, cyano, nitro, halo, alkyl, $CF_3$, alkoxy, carboxylate, ether, lower alkenyl, lower alkynyl, phenyl, benzyl, phenoxy, heteroaryl, alkylheteroaryl, heteroarylalkyl, amidoheteroaryl, alkoxyamidoheteroaryl, or alkylhalide group.

2. The method of claim 1, where the subject is a human, a domesticated animal, a zoo animal, or an experimental animal.

3. The method of claim 1, wherein the subject ers from an IgE-mediated disorder or disease.

4. The method of claim 1, wherein the subject suffers from an IgE-mediated disorder or disease selected from allergy, allergic rhinitis, allergic asthma, non-allergic asthma, anaphylaxis, atopic dermatitis, allergic gastroenteropathy, anaphylaxis, urticaria, drug allergies, food allergies, allergic bronchopulmonary aspergillosis, parasitic diseases, interstitial cystitis, hyper-IgE syndrome, ataxia-telangiectasia, Wiskott-Aldrich syndrome, athymic lymphoplasia, IgE myeloma, graft-versus-host reaction, and allergic purpura.

5. The method of claim 1, which reduces mast cell degranulation by at least 25%.

6. The method of claim 1, which reduces anaphylaxis in the subject by at least 50%.

7. The method of claim 1, which reduces mast cell degranulation by at least 25% upon subsequent exposure of the subject to the antigen.

8. The method of claim 1, which reduces anaphylaxis in the subject by at least 50% upon subsequent exposure of the subject to the antigen.

9. The method of claim 1, further comprising administering the antigen selected from an antibiotic, an antibacterial agent, a neuromuscular blocking drug, a food allergen, a therapeutic agent, an antibody, or a combination thereof to the subject.

10. The method of claim 1, wherein the second sugar has Formula I:

II where:
$R_{11}$ is a heteroatom, hydroxy, a covalent bond, third sugar, or carrier;
$R_{12}$ is a hydrogen, or a hydroxyl;
$R_{13}$ is a hydrogen, a hydroxyl, a heteroatom, or the first sugar;
$R_{14}$ is a hydrogen, or a hydroxyl; and
$R_{15}$ is a hydrogen, a hydroxyl, a heteroatom, a sulfate, or the first sugar.

11. The method of claim 1, wherein at least one Siglec ligand further comprises a third sugar of Formula III:

III where:
$R_{21}$ is a heteroatom, an alkoxy, ether, alkylamine, O-linked alkylamine, carrier, crosslinker, pegylated-lipid, lipid, or polyacrylamide, where the heteroatom, alkoxy, ether, alkylamine, or O-linked alkylamine can be linked to, or substituted with, a crosslinker, or a carrier;
$R_{22}$ is hydrogen, heteroatom, hydroxyl, N-acetylamine, amide, sulfonamide, urea, or thiourea, where the heteroatom, hydroxyl, N-acetylamine, amide, sulfonamide, urea, or thiourea can be substituted with an alkyl, aryl or heteroaryl; and where the alkyl, aryl, or heteroaryl can be substituted with one to five hydroxy, amino, azido, cyano, nitro; halo; alkyl, CF3, alkoxy, carboxylate, ether, lower alkenyl, lower alkynyl, phenyl, heteroaryl or alkylhalide group;

$R_{23}$ is a hydrogen, a hydroxyl, an acetylamine, or a fucose moiety;

$R_{24}$ is a heteroatom, a covalent bond, or the second sugar; and $R_{25}$ is a hydrogen, hydroxyl, sulfate, carboxylate, or phosphate.

12. The method of claim 1, where the composition comprises an antibody that binds to a FcεRI-IgE complex or an antibody fragment that binds to a FcεRI-IgE complex.

13. The method of claim 1, where at least one Siglec ligand comprises a Siglec-3 ligand comprising Formula I:

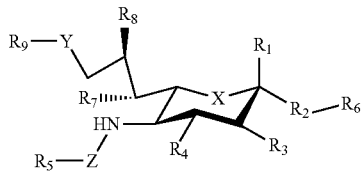

where:

X can be an oxygen heteroatom;

$R_1$ can be a carboxylate;

$R_2$ can be a hydrogen, a bond, a heteroatom, a hydroxy, a second sugar, or a carrier;

$R_3$ can be a hydrogen, or a hydroxyl;

$R_4$ can be a hydroxyl;

$R_5$ can be a lower alkyl, heteroaryl or

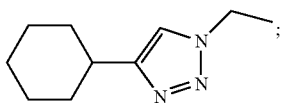

$R_6$ can be a hydrogen, a heteroatom, a hydroxy, an alkyl, an alkylamine, a second sugar, or a carrier;

$R_8$ can be a hydroxyl;

Y can be —CH$_2$-amide;

Z can be a carbonyl, carboxylate, methylene, acyl, aryl, heteroaryl, sulfonyl, —CH$_2$-sulfonyl, sulfonamide; —CH$_2$-sulfonamide, urea; —CH$_2$-urea, thiourea, or —CH$_2$-thiourea; and $R_9$ can be aryl, heteroaryl, or heterocycle, where the aryl, heteroaryl, or heterocycle can be substituted with one to five hydroxy, amino, cyano, nitro, halo, alkyl; CF$_3$, alkoxy, carboxylate, ether, lower alkenyl, lower alkynyl, phenyl, or alkylhalide groups.

14. The method of claim 1; here at least one Siglec ligand comprises a Siglec-8 ligand comprising Formula

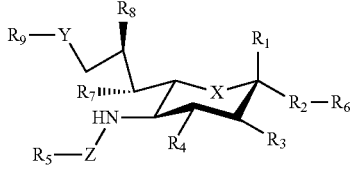

where:

X can be an oxygen heteroatom;

$R_1$ can be a carboxylate;

$R_2$ can be a hydrogen, a bond, a heteroatom, an alkyl, a hydroxy, a second sugar, or a carrier;

$R_3$ can be a hydrogen;

$R_4$ can a hydroxyl;

$R_5$ can be alkyl, aryl, alkylaryl, heteroaryl, or alkylheteroaryl, wherein the alkyl, aryl, alkylaryl, heteroaryl, or alkylheteroaryl can be substituted with one to two substituents selected from alkyl, phenyl, or cycloalkyl group(s);

$R_6$ can be a hydrogen, heteroatom, hydroxy, alkyl, alkylamine, a second sugar, or a carrier;

$R_7$ and $R_8$ can each independently be a hydrogen, or a hydroxyl;

Y can be sulfonamide, —CH$_2$-sulfonamide, amide, urea, or thiourea;

Z can be a carbonyl, carboxylate, methylene, acyl, aryl, heteroaryl, sulfonyl, —CH$_2$-sulfonyl, sulfonamide, —CH$_2$-sulfonamide, urea, —CH$_2$-urea, thiourea, —CH$_2$-thiourea, and $R_9$ can be aryl, heteroaryl, or heterocycle, where the aryl, heteroaryl, or heterocycle group can be substituted with one to five hydroxy, amino, cyano, nitro, halo, alkyl, CF$_3$, alkoxy, carboxylate, ether, lower alkenyl, lower alkynyl, phenyl, or alkylhalide groups.

* * * * *

UNITED STATES PATENT AND TRADEMARK OFFICE
CERTIFICATE OF CORRECTION

PATENT NO. : 10,994,006 B2
APPLICATION NO. : 16/315796
DATED : May 4, 2021
INVENTOR(S) : Paulson et al.

It is certified that error appears in the above-identified patent and that said Letters Patent is hereby corrected as shown below:

In the Specification

In Column 5, Line 50, delete "IOC" and insert --10C-- therefor

In Column 7, Line 32, delete "ug" and insert --µg-- therefor

In Column 7, Line 35, delete "ug" and insert --µg-- therefor

In Column 10, Lines 54-55, delete "heteroaryalkyl," and insert --heteroarylalkyl,-- therefor In Column 33, Line 62, delete "isopropyl" and insert --diisopropyl-- therefor In Column 35, Line 43, delete "nM" and insert --mM-- therefor In Column 35, Line 65, delete "MgCl2" and insert --MgCl$_2$-- therefor In Column 35, Line 66, delete "uM" and insert --µM-- therefor In Column 36, Line 21, delete "ug/mL" and insert --µg/mL-- therefor In Column 36, Line 22, delete "ug/mL" and insert --µg/mL-- therefor In Column 37, Line 35, delete "antigen-STAT," and insert --antigen-STAL-- therefor In Column 39, Line 56, delete "uM" and insert --µM-- therefor In Column 40, Line 35, delete "uM." and insert --µM.-- therefor In Column 41, Line 6, delete "ug" and insert --µg-- therefor Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,994,006 B2

In Column 41, Line 8, delete "ug" and insert --μg-- therefor

In Column 41, Line 15, delete "ug" and insert --μg-- therefor

In Column 41, Line 17, delete "ug" and insert --μg-- therefor

In Column 41, Line 22, delete "ug" and insert --μg-- therefor

In Column 41, Line 26, delete "ug" and insert --μg-- therefor

In Column 41, Line 30, delete "ug" and insert --μg-- therefor

In Column 41, Line 39, delete "ug" and insert --μg-- therefor

In Column 42, Line 50, delete "uM" and insert --μM-- therefor

In Column 43, Line 27, delete "uM." and insert --μM.-- therefor

In Column 43, Line 67, delete "ug" and insert --μg-- therefor

In Column 44, Line 1, delete "ug" and insert --μg-- therefor

In Column 44, Line 5, delete "uL" and insert --μL-- therefor

In Column 44, Line 46, delete "ug" and insert --μg-- therefor

In Column 44, Line 48, delete "ug" and insert --μg-- therefor

In Column 44, Line 53, delete "ug" and insert --μg-- therefor

In Column 44, Line 55, delete "ug" and insert --μg-- therefor

In Column 44, Line 60, delete "ug" and insert --μg-- therefor

In Column 45, Line 9, delete "ug" and insert --μg-- therefor

In Column 45, Line 12, delete "ug" and insert --μg-- therefor

In Column 52, Line 31, delete "(IC50" and insert --(IC$_{50}$-- therefor

In Column 52, Line 33, delete "(IC50" and insert --(IC$_{50}$-- therefor

In Column 52, Line 36, delete "(IC50" and insert --(IC$_{50}$-- therefor

In Column 53, Line 34, delete "ug/ml" and insert --μg/ml-- therefor

CERTIFICATE OF CORRECTION (continued)
U.S. Pat. No. 10,994,006 B2

In Column 63, Line 21, delete "hevacizumab," and insert --bevacizumab,-- therefor In the Claims In Column 65, Line 32, in Claim 1, delete "aryl;" and insert --aryl,-- therefor In Column 65, Line 66, in Claim 3, delete "ers" and insert --suffers-- therefor In Column 66, Line 27, in Claim 10, delete "I:" and insert --II:-- therefor In Column 67, Line 4, in Claim 11, delete "nitro; halo;" and insert --nitro, halo,-- therefor In Column 67, Line 4, in Claim 11, delete "CF3," and insert --$CF_3$,-- therefor In Column 68, Line 2, in Claim 13, delete "sulfonamide;" and insert --sulfonamide,-- therefor In Column 68, Line 3, in Claim 13, delete "urea;" and insert --urea,-- therefor In Column 68, Line 7, in Claim 13, delete "alkyl;" and insert --alkyl,-- therefor In Column 68, Line 10, in Claim 14, delete "claim 1; here" and insert --claim 1, where-- therefor In Column 68, Line 11, in Claim 14, delete "Formula" and insert --Formula I:-- therefor In Column 68, Line 28, in Claim 14, after "can", insert --be--